United States Patent
Rover et al.

(10) Patent No.: US 10,577,544 B2
(45) Date of Patent: Mar. 3, 2020

(54) LOW TEMPERATURE, LOW PRESSURE UPGRADING AND STABILIZATION OF BIO-OIL OR BIO-OIL FRACTIONS

(71) Applicant: Iowa State University Research Foundation, Inc., Ames, IA (US)

(72) Inventors: Marjorie Rover, Ames, IA (US); Robert C. Brown, Ames, IA (US); Patrick H. Hall, Ames, IA (US); Ryan G. Smith, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 0 days.

(21) Appl. No.: 14/687,590

(22) Filed: Apr. 15, 2015

(65) Prior Publication Data

US 2015/0291892 A1    Oct. 15, 2015

Related U.S. Application Data

(60) Provisional application No. 61/979,697, filed on Apr. 15, 2014.

(51) Int. Cl.
*C10G 45/10* (2006.01)
*C10G 1/00* (2006.01)
(Continued)

(52) U.S. Cl.
CPC .............. *C10G 45/10* (2013.01); *C07C 1/207* (2013.01); *C10G 1/002* (2013.01); *C10G 45/06* (2013.01);
(Continued)

(58) Field of Classification Search
CPC ............................ Y02E 50/14; C10L 2290/54
See application file for complete search history.

(56) References Cited

U.S. PATENT DOCUMENTS

| | | |
|---|---|---|
| 4,163,750 A | 8/1979 | Bird et al. |
| 7,910,758 B2 | 3/2011 | Hassan et al. |

(Continued)

FOREIGN PATENT DOCUMENTS

| | | | |
|---|---|---|---|
| WO | 2010033789 A2 | 3/2010 | |
| WO | WO-2010033789 A2 * | 3/2010 | ............ B01J 23/002 |

(Continued)

OTHER PUBLICATIONS

Roel J. M. Westerhof, Nobert J. M. Knipers, Sascha R A. Kersten, and Wim P.M. can Swaaij, "Controlling the Water Content of Biomass Fast Pyrolysis Oil", Ind Eng. Chem. Res. , 46, 9238-9247 (Year: 2007).*

(Continued)

*Primary Examiner* — Ellen M Mcavoy
*Assistant Examiner* — Ming Cheung Po
(74) *Attorney, Agent, or Firm* — Pepper Hamilton LLP

(57) ABSTRACT

The present application discloses low temperature, low pressure methods (LTLP) for upgrading and/or stabilizing bio-oil or a bio-oil fraction. One method comprises providing a bio-oil or bio-oil fraction and hydrogen, which are reacted in the presence of a catalyst at a temperature of less than 150° C. and a pressure of less than 100 bar (absolute) to produce a hydrogenated liquid oil at a carbon yield of over 75%. Another method comprises providing a bio-oil or bio-oil fraction, providing oxygen reducing reaction conditions, and reacting the bio-oil or bio-oil fraction under the oxygen reducing reaction conditions at LTLP to produce an upgraded bio-oil product containing fewer carbonyls than the bio-oil or bio-oil fraction. Yet another method comprises providing a bio-oil or bio-oil fraction and a solution comprising one or more fermentation organisms and a sugar source. The solution and bio-oil or bio-oil fraction are combined to obtain a fermentation mixture, which is incu- (Continued)

bated at 15° C. to 30° C. for 16 to 72 hours to produce an upgraded bio-oil fermentation product containing fewer carbonyls than the bio-oil or bio-oil fraction.

17 Claims, 38 Drawing Sheets

(51) Int. Cl.
```
C07C 1/207      (2006.01)
C10G 45/06      (2006.01)
C10G 45/08      (2006.01)
C12P 7/64       (2006.01)
```
(52) U.S. Cl.
CPC ............... *C10G 45/08* (2013.01); *C12P 7/64* (2013.01); *C07C 2523/42* (2013.01); *C07C 2523/44* (2013.01); *C07C 2523/46* (2013.01); *C07C 2523/882* (2013.01); *C07C 2523/883* (2013.01); *C07C 2527/11* (2013.01)

(56) References Cited

U.S. PATENT DOCUMENTS

| | | | |
|---|---|---|---|
| 8,476,480 B1 | 7/2013 | Brown et al. | |
| 2010/0076238 A1* | 3/2010 | Brandvold | C10G 45/58 585/324 |
| 2012/0285079 A1* | 11/2012 | Oasmaa | C10G 3/47 44/437 |

FOREIGN PATENT DOCUMENTS

| | | | | |
|---|---|---|---|---|
| WO | WO 2010033789 A3 * | 7/2010 | ............ | B01J 23/002 |
| WO | WO 2010102145 A1 * | 9/2010 | ............... | C01B 3/34 |
| WO | WO-2010102145 A1 * | 9/2010 | ............... | C01B 3/34 |

OTHER PUBLICATIONS

Venderbosch et al., "Stabilization of biomass-derived pyrolysis oils," J. Chem. Technol. Biotechnol. 85:674-686 (2009).
Wildschut et al., "Hydrotreatment of Fast Pyrolysis Oil Using Heterogeneous Nobel-Metal Catalysts," Ind. Eng. Chem. Res. 48: 10324-10334 (2009).
International Search Report and the Written Opinion of the International Search Authority for PCT/US2015/025945, dated Aug. 31, 2015.
Rover et al., "Stabilization of bio-oils using low temperature, low pressure hydrogenation," Fuel 153: 224-230 (2015).
Rover et al., "Why are we trying to upgrade bio-oil as if it was petroleum?," Oral Presentation at TCS2014: Symposium on Thermal and Catalytic Sciences for Biofuel and Biobased Products, Sep. 2-5, 2014, Denver, Colorado.
Rover et al., "Why are we trying to hydroprocess bio-oils as if they were petroleum?," Online Abstract on TCS Website, for TCS2014: Symposium on Thermal and Catalytic Sciences for Biofuel and Biobased Products, published May 8, 2014.
Brown, "Py Refinery for Sub-Sahara Africa and other Developing Regions of the World", Proposal to Stanford Global Climate and Energy Program, Stanford University, submitted Mar. 5, 2014.
Baker et al., "Catalytic Hydrotreating of Biomass-Derived Oils," Pacific Northwest Laboratory, Richland, WA, operated for the U.S. Department of Energy, pp. 257-263 (1988).
Ben et al., "Production of Renewable Gasoline from Aqueous Phase Hydrogenation of Lignin Pyrolysis Oil," Fuel 103:1148-53 (2013).
Busetto et al., "Application of the Shvo Catalyst in Homogeneous Hydrogenation of Bio-Oil Obtained from Pyrolysis of White Poplar: New Mild Upgrading Conditions," Fuel 90:1197-1207 (2011).
Chaiwat et al., "Upgrading of Bio-Oil Into Advanced Biofuels and Chemicals. Part II. Importance of Holdup of Heavy Species During the Hydrotreatment of Bio-Oil in a Continuous Packed-Bed Catalytic Reactor," Fuel 112:302-10 (2013).
Choi et al., "Detailed Characterization of Red Oak-Derived Pyrolysis Oil: Integrated Use of GC, HPLC, IC, GPC, and Karl-Fischer," Journal of Analytical and Applied Pyrolysis 110:147-54 (2014).
Diebold et al., "Additives to Lower and Stabilize the Viscosity of Pyrolysis Oils During Storage," Energy & Fuels 11:1081-91 (1997).
Diebold, J.P., "A Review of the Chemical and Physical Mechanisms of the Storage Stability of Fast Pyrolysis Bio-Oils," National Renewable Energy Laboratory, 59 pages (Jan. 2000).
Elliott et al., "Catalytic Hydroprocessing of Biomass Fast Pyrolysis Bio-Oil to Produce Hydrocarbon Products," Environmental Progress & Sustainable Energy 28(3):441-49 (2009).
Friedman et al., "Alkali Metals as Hydrogenation Catalysts for Aromatic Molecules," J. Org. Chem. 36(5):694-7 (1971).
Harada et al., "A Simple Method for Preparing Highly Active Palladium Catalysts Loaded on Various Carbon Supports for Liquid-Phase Oxidation and Hydrogenation Reactions," Journal of Molecular Catalysts A: Chemical 268:59-64 (2007).
Huang et al., "Homogeneous Catalytic Hydrogenation of Bio-Oil and Related Model Aldehydes with RuCl2(PPh3)3," Chem. Eng. Technol. 33(12):2082-8 (2010).
Iliopoulou et al., "Catalytic Upgrading of Biomass Pyrolysis Vapors Using Transition Metal-Modified ZSM-5-Zeolite," Applied Catalysis B: Environmental 127:281-90 (2012).
Ingram et al., "Pyrolysis of Wood and Bark in an Auger Reactor: Physical Properties and Chemical Analysis of the Produced Bio-Oils," Energy & Fuels 22:614-25 (2008).
Jones et al., "Production of Gasoline and Diesel from Biomass Via Fast Pyrolysis, Hydrotreating and Hydrocracking: A Design Case," Pacific Northwest National Laboratory prepared for the U.S. Department of Energy, 66 pages (Feb. 2009).
Mercader et al., "Pyrolysis Oil Upgrading by High Pressure Thermal Treatment," Fuel 89:2829-37 (2010).
Mohan et al., "Pyrolysis of Wood/Biomass for Bio-Oil: A Critical Review," Energy & Fuels 20:848-89 (2006).
Mortensen et al., "A Review of Catalytic Upgrading of Bio-Oil to Engine Fuels," Applied Catalysis A: General 407:1-19 (2011).
Mullen et al., "Characterization of Various Fast-Pyrolysis Bio-Oils by NMR Spectroscopy," Energy & Fuels 23:2707-18 (2009).
Numwong et al., "Partial Hydrogenation of Polyunsaturated Fatty Acid Methyl Esters Over Pd/Activated Carbon: Effect of Type of Reactor," Chemical Engineering Journal 210:173-81 (2012).
Oasmaa et al., "Characterization of Hydrotreated Fast Pyrolysis Liquids," Energy Fuels 24:5264-72 (2010).
OSHA Technical Manual (OTM), "Petroleum Refining Process," Section IV: Chapter 2, 30 pages (accessed Mar. 29, 2017).
Panpranot et al., "Effects of Pd Precursors on the Catalytic Activity and Deactivation of Silica-Supported Pd catalysts in Liquid Phase Hydrogenation," Applied Catalysts A: General 292:322-27 (2005).
Pollard et al., "Characterization of Bio-Oil Recovered as Stage Fractions with Unique Chemical and Physical Properties," Journal of Analytical and Applied Pyrolysis 93:129-38 (2012).
Rover et al., "The Effect of Pyrolysis Temperature on Recovery of Bio-Oil as Distinctive Stage Fractions," Journal of Analytical and Applied Pyrolysis 105:262-68 (2014).
Rover et al., "Production of Clean Pyrolytic Sugars for Fermentation," ChemSusChem 7:1662-68 (2014).
Venderbosch et al., "Fast Pyrolysis," Thermochemical Processing of Biomass: Conversion into Fuels, Chemicals and Power, First Edition, Edited by Robert C. Brown, John Wiley & Sons, Ltd., Chapter 5, pp. 124-156 (2011).
Wei et al., "Highly Efficient and Chemoselective Hydrogenation of Alpha, Beta-Unsaturated Carbonyls Over Pd/N-Doped Hierarchically Porous Carbon," Catal. Sci. Technol. 5:397-404 (2015).
Wildschut et al., "Hydrotreatment of Fast Pyrolysis Oil Using Heterogeneous Noble-Metal Catalysts," Ind. Eng. Chem. Res. 48:10324-34 (2009).
Wildschut et al., "Catalyst Studies on the Hydrotreatment of Fast Pyrolysis Oil," Applied Catalysis B: Environmental 99:298-306 (2010).
Heeres et al., "Novel Ni-Based Catalysts for the Hydrotreatment of Fast Pyrolysis Oil," in BioEnergy IV: Innovations in Biomass

(56) References Cited

OTHER PUBLICATIONS

Conversion for Heat, Power, Fuels and Chemicals, Engineering Conferences International ECI Digital Archives (2013).
Huber et al., "Synthesis of Transportation Fuels from Biomass: Chemistry, Catalysts, and Engineering," Chem. Rev. 106:4044-98 (2006).
Wildschut et al., "Catalytic Hydrotreatment of Fast Pyrolysis Oil: Model Studies on Reaction Pathways for the Carbohydrate Fraction," Environmental Progress & Sustainable Energy 28(3):450-60 (2009).
Mahfud et al., "Hydrogenation of Fast Pyrolysis Oil and Model Compounds in a Two-Phase Aqueous Organic System Using Homogeneous Ruthenium Catalysts," Journal of Molecular Catalysis A: Chemical 264:227-36 (2007).
Xu et al., "Two-Step Catalytic Hydrodeoxygenation of Fast Pyrolysis Oil to Hydrocarbon Liquid Fuels," Chemosphere 93:652-60 (2013).
Li et al., "Upgrading of Bio-Oil Into Advanced Biofuels and Chemicals. Part III. Changes in Aromatic Structure and Coke Forming Propensity During the Catalytic Hydrotreatment of a Fast Pyrolysis Bio-Oil with Pd/C Catalyst," Fuel 116:642-49 (2014).

\* cited by examiner

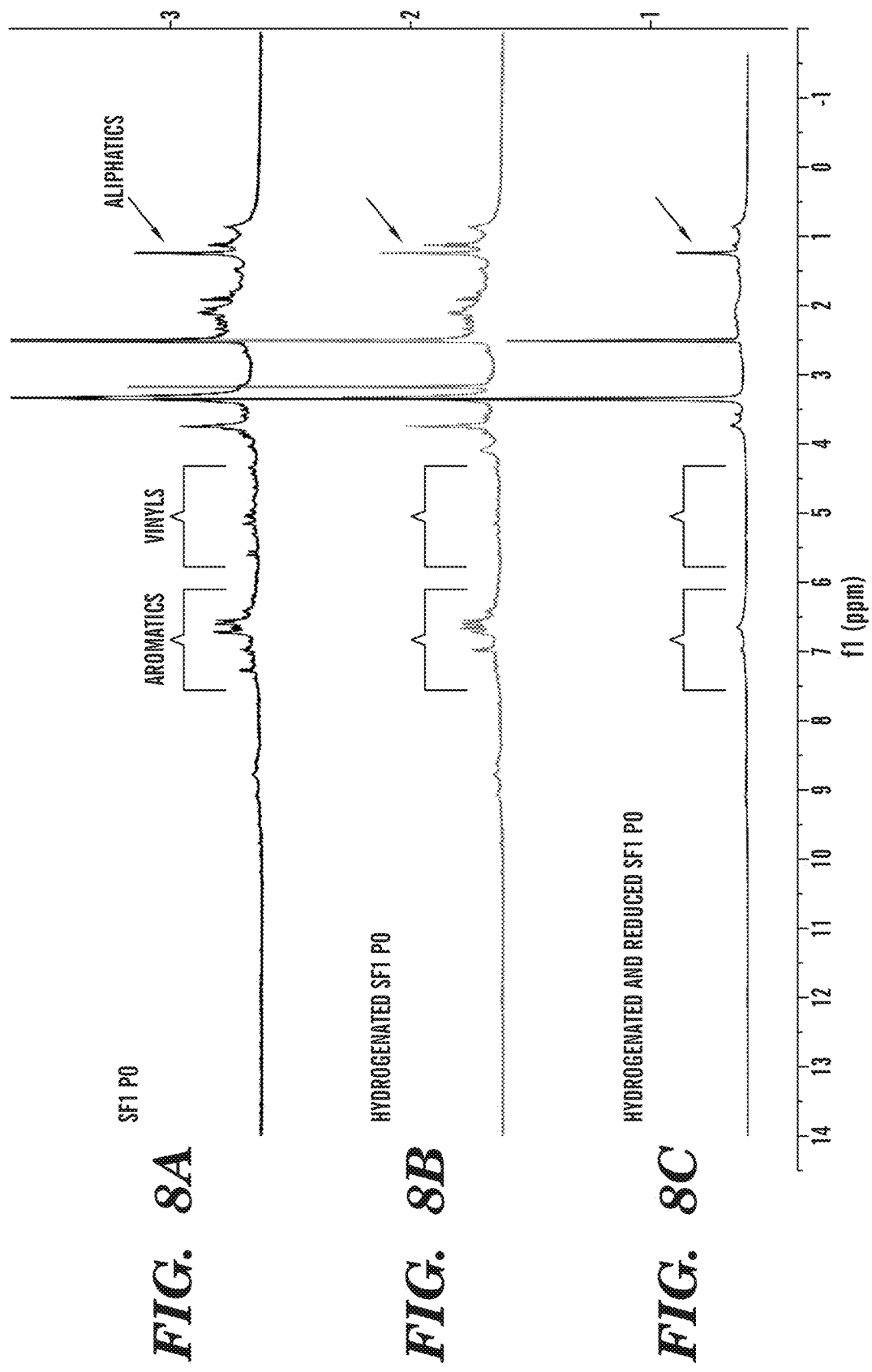

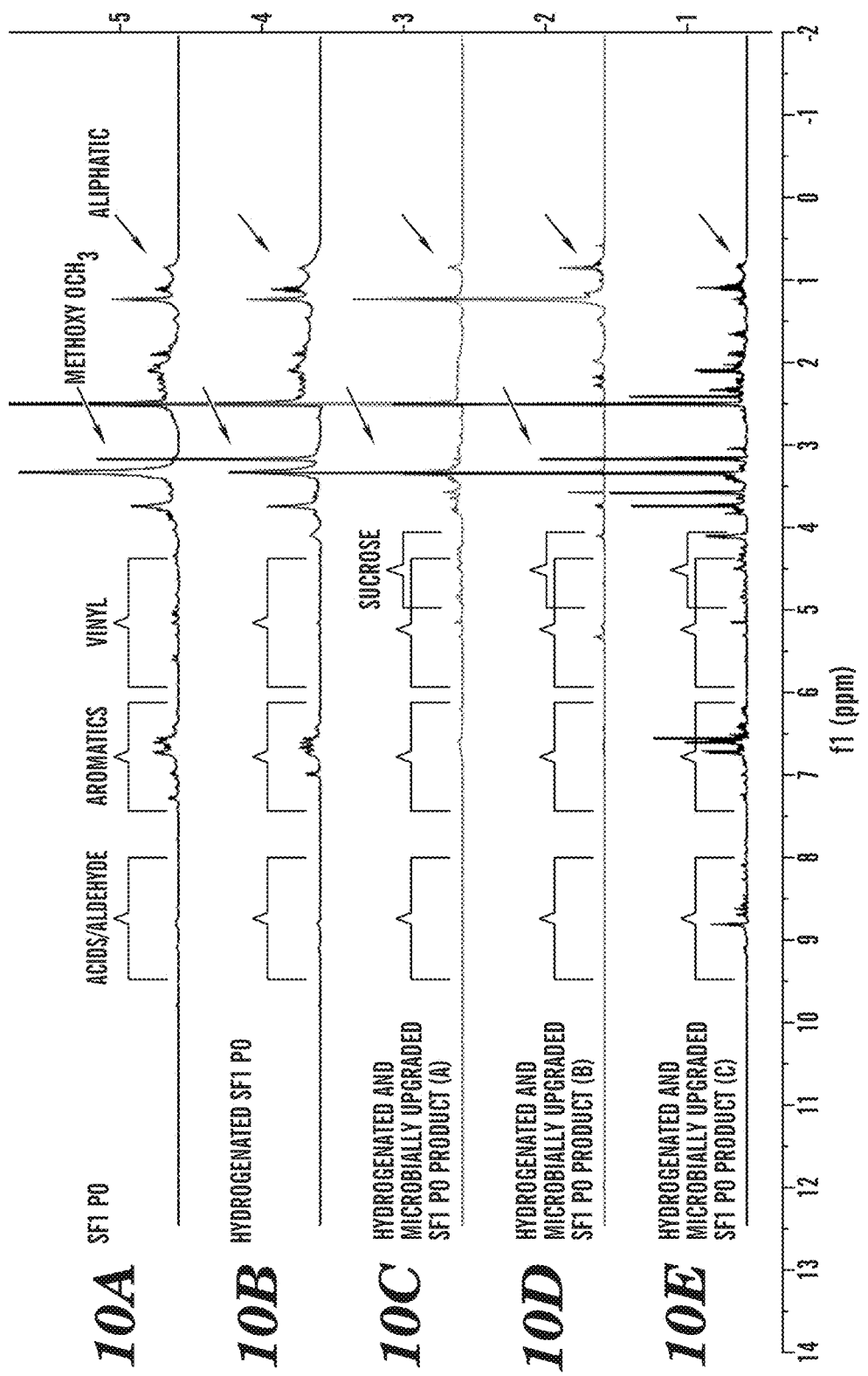

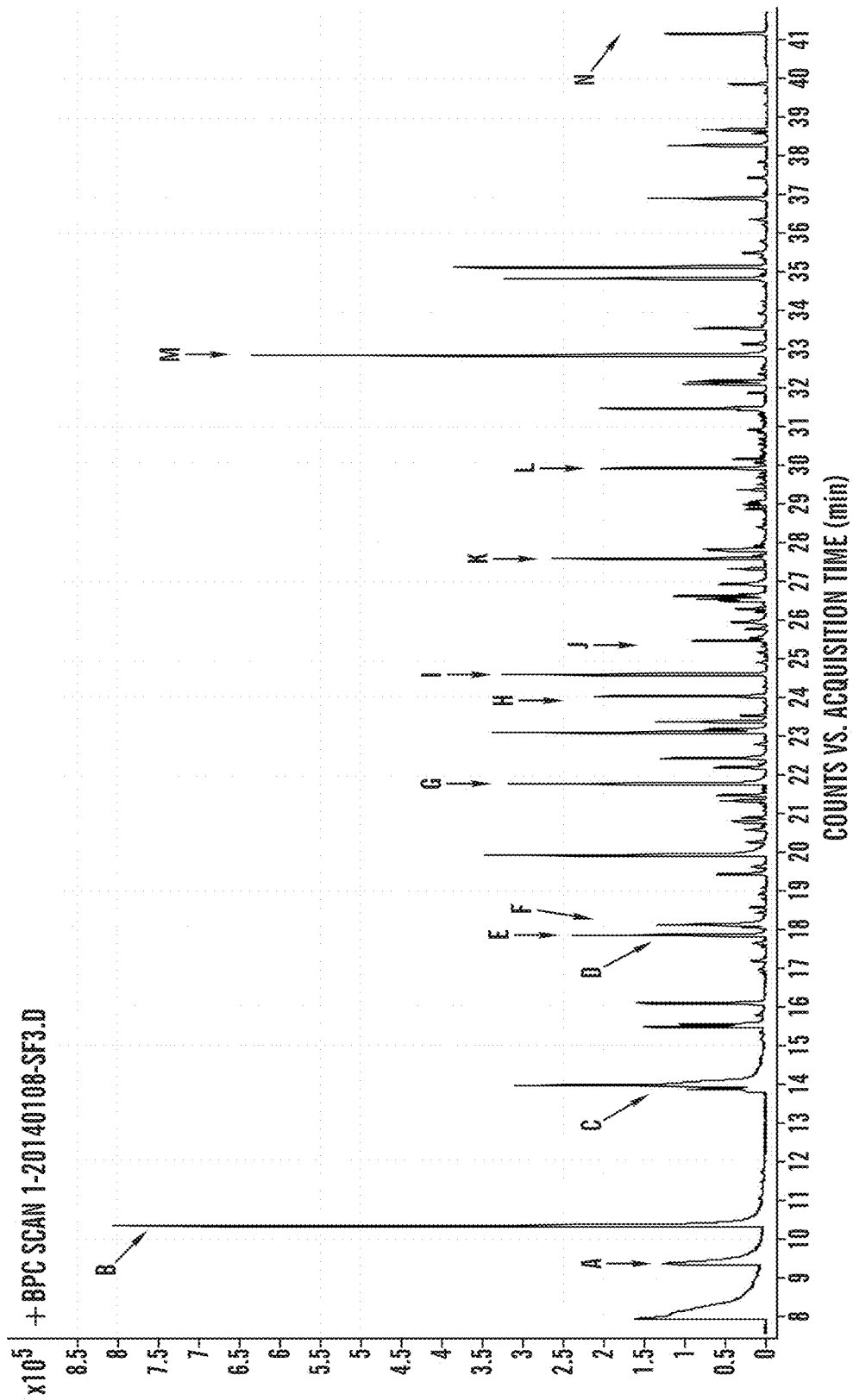

COMPOUNDS A-N:
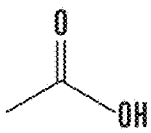
A. ACETIC ACID
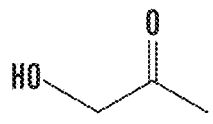
B. 2-PROPANONE, 1-HYDROXY-
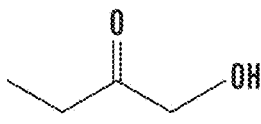
C. 1-HYDROXY-2-BUTANONE
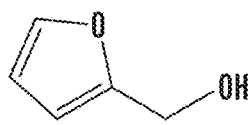
D. 2-FURANMETHANOL
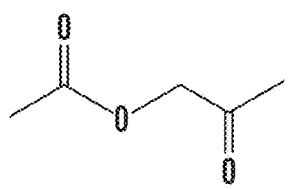
E. 2-PROPANONE, 1-(ACETYLOXY)-
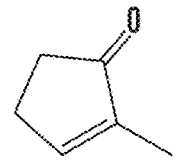
F. 2-CYCLOPENTEN-1-ONE, 2-METHYL-
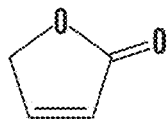
G. 2(5H)-FURANONE
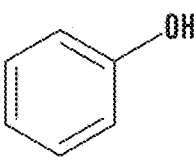
H. PHENOL
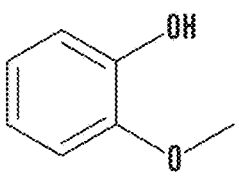
I. PHENOL, 2-METHOXY-
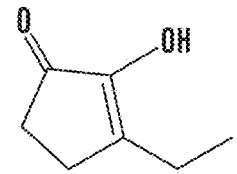
J. 2-CYCLOPENTEN-1-ONE, 3-ETHYL-2-HYDROXY-
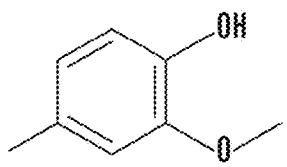
K. CREOSOL
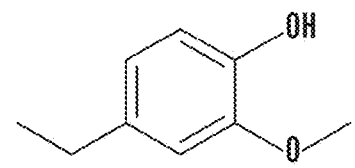
L. PHENOL, 4-ETHYL-2-METHOXY-
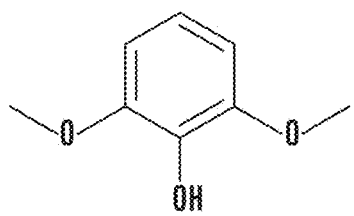
M. PHENOL, 2,6-DIMETHOXY
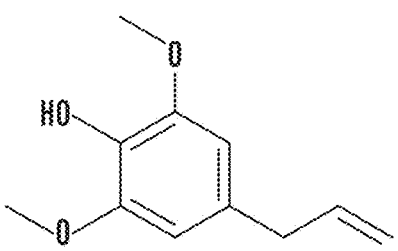
N. PHENOL, 2,6-DIMETHOXY-4-(2-PROPENYL)-
*FIG. 15A (cont.)*

COMPOUNDS A-L:
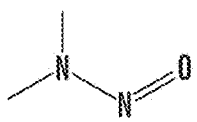
A. N-NITROSODIMETHYLAMINE
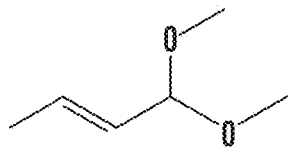
B. 2-BUTENE, 1,1-DIMETHOXY-
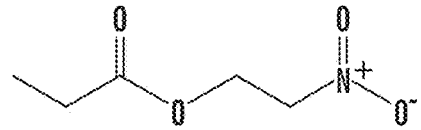
C. ETHANOL, 2-NITRO-, PROPIONATE (ESTER)
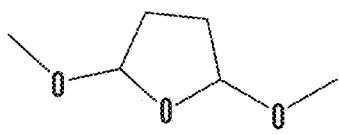
D. FURAN, TETRAHYDRO-2,5-DIMETHOXY-
E. 2-CYCLOPENTEN-1-ONE
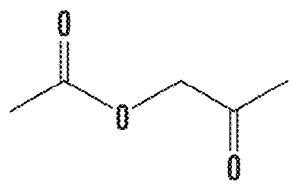
F. 2-PROPANONE, 1-(ACETYLOXY)-
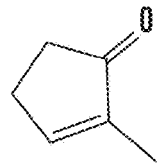
G. 2-CYCLOPENTEN-1-ONE, 2-METHYL-
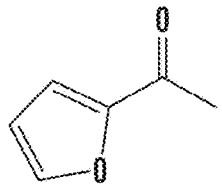
H. ETHANONE, 1-(2-FURANYL)-
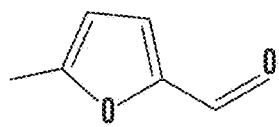
I. 2-FURANCARBOXALDEHYDE, 5-METHYL-
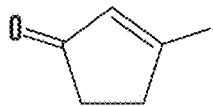
J. 2-CYCLOPENTEN-1-ONE, 3-METHYL-
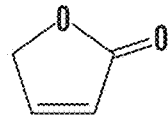
K. 2(5H)-FURANONE
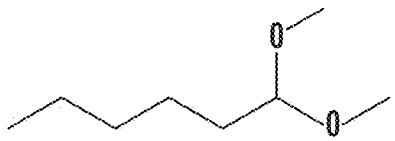
L. HEXANAL DIMETHYL ACETAL
*FIG. 15B (cont.)*

COMPOUNDS A-N:
A. 2-CYCLOPENTEN-1-ONE, 3-METHYL-
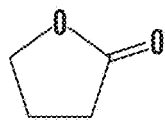
B. BUTYROLACTONE
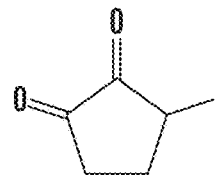
C. 1,2-CYCLOPENTANEDIONE, 3-METHYL-
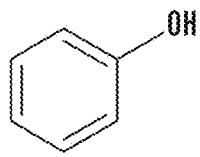
D. PHENOL
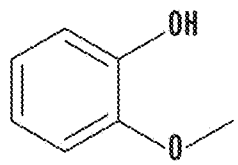
E. PHENOL, 2-METHOXY-
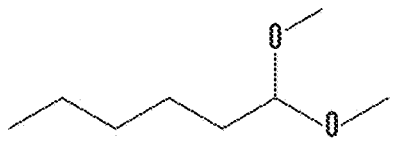
F. HEXANAL DIMETHYL ACETAL
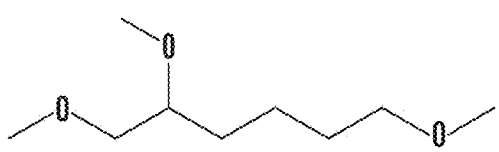
G. 1,2,6-TRIMETHOXY-HEXANE
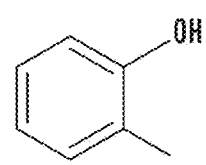
H. PHENOL, 2-METHYL-
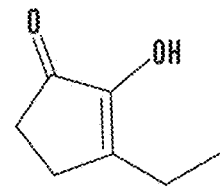
I. 2-CYCLOPENTEN-1-ONE, 3-ETHYL-2-HYDROXY-
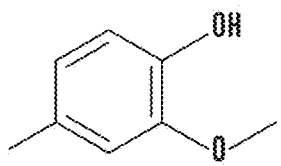
J. CREOSOL
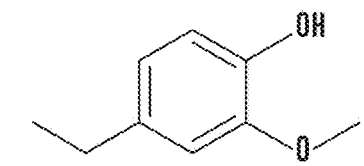
K. PHENOL, 4-ETHYL-2-METHOXY-
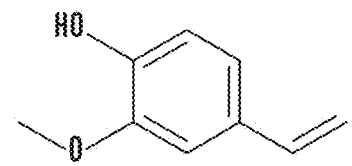
L. 2-METHOXY-4-VINYLPHENOL
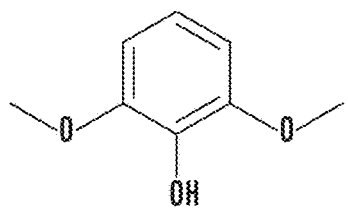
M. PHENOL, 2,6-DIMETHOXY
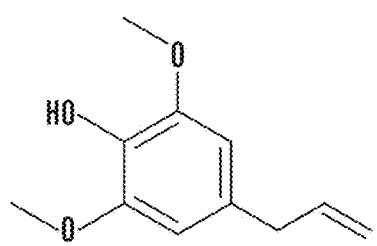
N. PHENOL, 2,6-DIMETHOXY-4-(2-PROPENYL)-
*FIG. 15C (cont.)*

COMPOUNDS A-J:
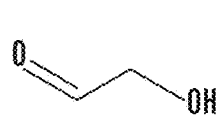
A. ACETALDEHYDE, HYDROXY
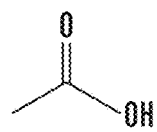
B. ACETIC ACID
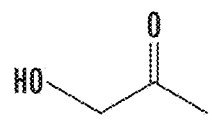
C. 2-PROPANONE, 1-HYDROXY
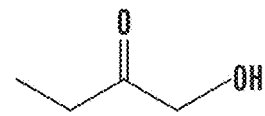
D. 1-HYDROXY-2-BUTANONE
E. 1,2-ETHANEDIOL, MONOACETATE
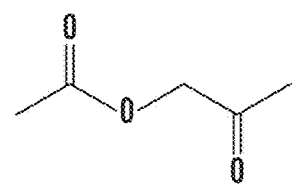
F. 2-PROPANONE, 1-(ACETYLOXY)-
G. 2-CYCLOPENTEN-1-ONE, 3-METHYL-
H. BUTANOIC ACID, 4-HYDROXY-
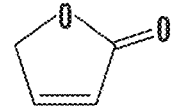
I. 2(5H)-FURANONE
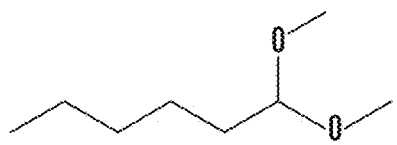
J. HEXANAL DIMETHYL ACETAL
*FIG. 15D (cont.)*

COMPOUNDS A-K:
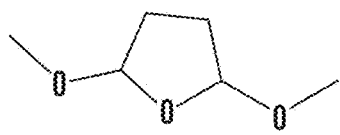
A. FURAN, TETRAHYDRO-2,5-DIMETHOXY
B. 2(5H)-FURANONE
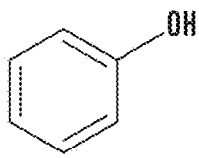
C. PHENOL
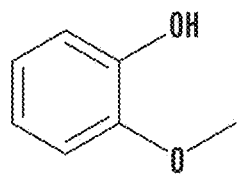
D. PHENOL, 2-METHOXY
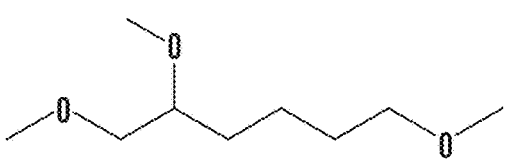
E. 1,2,6-TRIMETHOXY-HEXANE
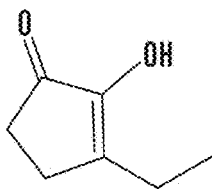
F. 2-CYCLOPENTEN-1-ONE, 3-ETHYL-2-HYDROXY-
G. 4-METHYL-5H-FURAN-2-ONE
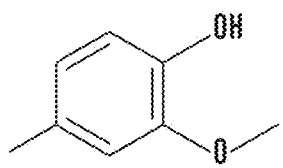
H. CREOSOL
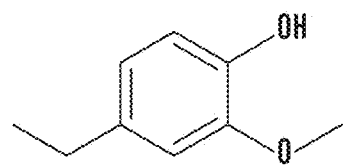
I. PHENOL, 4-ETHYL-2-METHOXY-
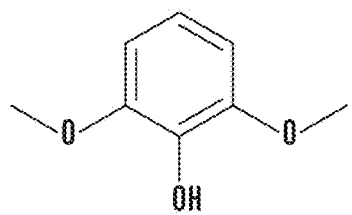
J. PHENOL, 2,6-DIMETHOXY
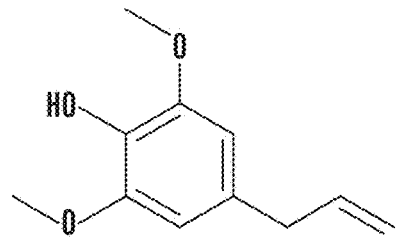
K. PHENOL, 2,6-DIMETHOXY-4-(2-PROPENYL)-
*FIG. 15E (cont.)*

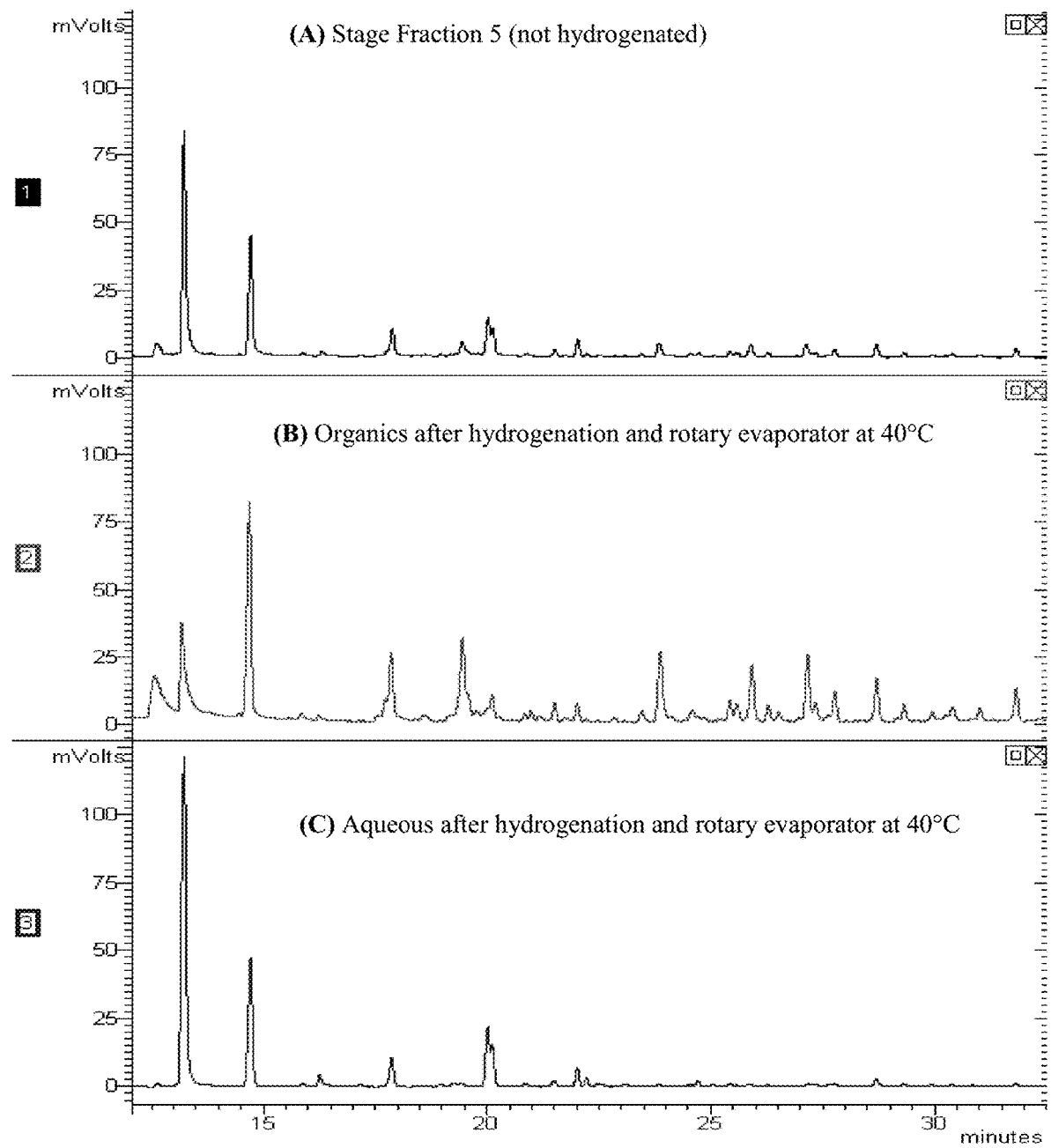
FIGURES 17A-C

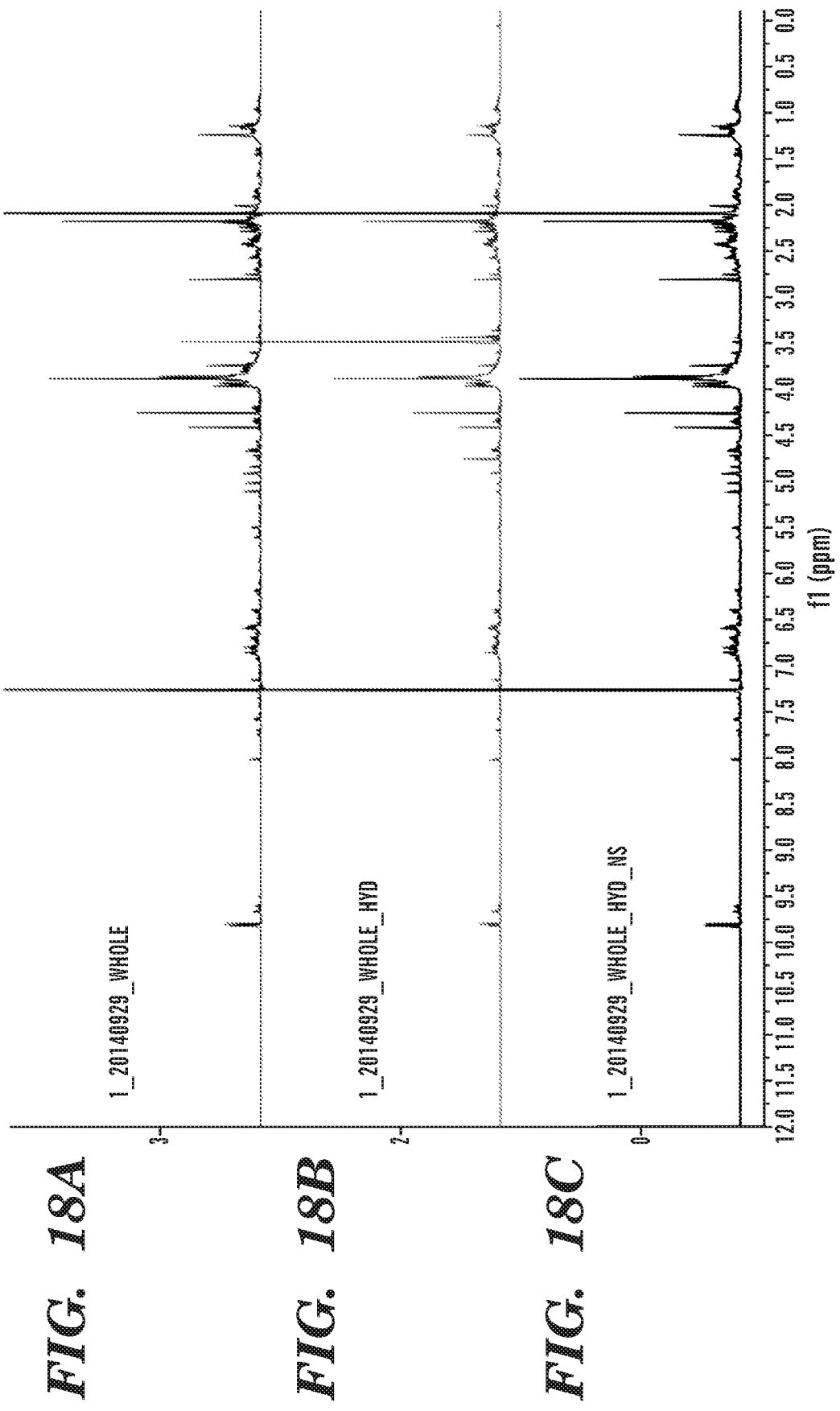

LOW TEMPERATURE, LOW PRESSURE UPGRADING AND STABILIZATION OF BIO-OIL OR BIO-OIL FRACTIONS

This application claims the benefit of U.S. Provisional Patent Application Ser. No. 61/979,697, filed Apr. 15, 2014, which is hereby incorporated by reference in its entirety.

FIELD OF THE INVENTION

The present invention relates to low temperature, low pressure upgrading and stabilization of bio-oil and bio-oil fractions.

BACKGROUND OF THE INVENTION

Worldwide energy consumption has never been higher than it is today, due to society's way of living and an increasing human population (United Nations Department of Economic and Social Affairs, 2010, http://www.un.org/esa/population/) and (U.S. Energy Information Administration Independent Statistics and Analysis, 2010, http://www.eia.doe.gov/). The transportation sector accounts for about one fifth of the total energy consumption (B. van Ruijven et al., *Energy Policy*, 37: 4797 4808 (2009)). Thus, as the world's population grows and means of transportation become more readily available, it is unavoidable that the need for fuels will only increase in the future (M. Balat, *Energy Conyers. Manage.*, 52: 858-875 (2011)). This increasing fuel need constitutes one of the major challenges of the near future, as present fuels are primarily produced from crude oil and these reserves are depleting (S. Sorrell, et al., *Energ. Policy*, 38: 5290-5295 (2010)).

Substantial research within the energy field is being performed in order to find alternative fuels to replace gasoline and diesel. The optimal solution would be an alternative fuel that is equivalent to the conventional fuels, i.e. compatible with the infrastructure, but also a fuel that is sustainable and will decrease $CO_2$ emissions, thereby decreasing man's environmental footprint (R. Pachauri, A. Reisinger (Eds.), *Climate Change* 2007: *Synthesis Report. Contribution of Working Groups I, II and III to the Fourth Assessment Report of the Intergovernmental Panel on Climate Change, Technical Report. IPCC* (2007)).

Biomass derived fuels could be the prospective fuel of tomorrow as they can be produced within a relatively short cycle and are considered benign for the environment (M. Balat, *Energy Conyers. Manage.*, 52: 858-875 (2011); A. Roedl, *Int. J. Life Cycle Assess.*, 15: 567-578 (2010)).

Bio-oil, in particular, is increasingly being recognized as an important feedstock (Lappas et al., "Production of Biofuels via Co-processing in Conventional Refining Processes," *Catalysis Today*, 145:55-62 (2009); Bridgwater, "Review of Fast Pyrolysis of Biomass and Product Upgrading," *Biomass and Bioenergy*, 38:68-94 (2012)) for thermochemical-based biorefinery applications for transportation fuels, energy and chemicals (Vitasari et al., "Water Extraction of Pyrolysis Oil: The First Step for the Recovery of Renewable Chemicals," *Biores. Technol.* 102(14):7204-7210 (2011)) even though bio-oil exhibits negative characteristics.

Bio-oil contains 42-48 wt % oxygen (Oasmaa et al., "Fast Pyrolysis Bio-Oils from Wood and Agricultural Residues," *Energy & Fuels* 24:1380-1388 (2009); Mohan et al., "Pyrolysis of Wood/Biomass for Bio-Oil: A Critical Review," *Energy & Fuels*, 20:848-889 (2006)), which must be reduced by catalytic upgrading before co-feeding in a refinery unit to produce transportation fuels (Lappas et al., "Production of Biofuels via Co-processing in Conventional Refining Processes," *Catalysis Today*, 145:55-62 (2009)). Several other problems to direct upgrading of bio-oil includes high water content (15-30%), limited stability, and high acidity (Lappas et al., "Production of Biofuels via Co-processing in Conventional Refining Processes," *Catalysis Today*, 145:55-62 (2009); Oasmaa et al., "Fuel Oil Quality of Biomass Pyrolysis Oils—State of the Art for the End User," *Energy & Fuels*, 13:914-921 (1999); Chiaramonti et al., "Power Generation using Fast Pyrolysis Liquids from Biomass," *Renew. Sust. Energy Rev.* 11:1056-1086 (2007)).

Bio-oil, the liquid product of fast pyrolysis (i.e., thermal deconstruction) of biomass, superficially resembles petroleum. Both are dark, viscous liquids consisting of hundreds of organic compounds. The superficial similarities between petroleum and bio-oil have encouraged efforts to employ petroleum hydroprocessing in the upgrading of bio-oil, which has had limited success.

Bio-oil is an emulsion of predominantly lignin-derived phenolic oligomers in an aqueous phase containing primarily carbohydrate-derived compounds (D. Mohan, et al., *Energy & Fuels*, 20: 848-889 (2006)). Bio-oil has several characteristics that make it undesirable as fuel[3, 4] such as poor storage stability (A. V. Bridgwater, *Biomass and Bioenergy*, 38: 68-94 (2012); L. Busetto, et al., *Fuel*, 90: 1197-1207 (2011); high acidity and corrosivity (L. Busetto, et al., *Fuel*, 90: 1197-1207 (2011); T. N. Pham, et al., *Applied Catalysis B: Environmental*, 145: 10-23 (2014); P. M. Mortensen, et al., *Applied Catalysis A: General*, 407: 1-19 (2011); F. d. M. Mercader, et al., *Fuel*, 89: 2829-2837 (2010)); low heating value, high viscosity, incomplete volatility (L. Busetto, et al., *Fuel*, 90: 1197-1207 (2011); S. Czernik and A. V. Bridgwater, *Energy & Fuels*, 18: 590-598 2004)); and immiscibility with petroleum fuels (D. Mohan, et al., *Energy & Fuels*, 20: 848-889 (2006); F. d. M. Mercader, et al, *Fuel*, 89: 2829-2837 (2010)).

For bio-oil to be upgraded into transportation fuels, both deoxygenation and saturation of bio-oil is required. However, attempts to use hydroprocessing at the severe conditions typical in petroleum refining leads to coke formation and poor yields of organic liquids. Petroleum consists of non-polar hydrocarbons that are relatively stable, requiring elevated temperatures and pressures (400-800° C. and 68-138 bar) (OSHA, ed. U. S. D. o. Labor, Washington, D.C., 2013) to encourage chemical transformations, whereas bio-oil consists of oxygenated organic compounds whose high degree of functionality makes them chemically reactive even at low temperatures and pressures. Attempts to catalytically upgrade bio-oil have been hampered by its poor thermal stability at elevated temperatures, leading to coke formation and rapid catalyst deactivation (15. J. Wildschut, et al., *Applied Catalysis B: Environmental*, 99: 298-306 (2010); X. Xu, et al., *Chemosphere*, 93: 652-660 (2013); X. Li, et al., *Fuel*, 116: 642-649 (2014); A. Ardiyanti, Ph.D., University of Groningen (2013); J. Wildschut, Ph.D., University of Groningen (2009)). Bio-oil is thermally unstable as a result of the high chemical reactivity of the various functional groups it contains, particularly carbonyl and vinyl groups.

A major problem with upgrading bio-oil is its poor thermal stability at elevated temperatures, leading to heavy tar and coke formation, which rapidly deactivates upgrading catalysts.[11-17] (G. W. Huber, et al., *Chemical Reviews*, 106: 4044-4098 (2006); F. Huang, et al., *Chemical Engineering & Technology*, 33: 2082-2088 (2010); F. H. Mahfud, et al.,

*Journal of Molecular Catalysis A: Chemical*, 264: 227-236 (2007); J. Wildschut, et al., *Industrial & Engineering Chemistry Research*, 48: 10324-10334 (2009); J. Wildschut, et al., *Applied Catalysis B: Environmental*, 99: 298-306 (2010); X. Xu, et al., *Chemosphere*, 93: 652-660 (2013); X. Li, et al., *Fuel*, 116: 642-649 (2014)).

Studies have specifically implicated polymerization of phenolic compounds in bio-oil to form "asphalt-like" materials that dehydrate to coke and ultimately cause deactivation of the hydroprocessing catalyst (J. Wildschut, et al., *Applied Catalysis B: Environmental*, 99: 298-306 (2010); A. Ardiyanti, Ph.D., University of Groningen (2013)). Even when stored for long periods or heated in the absence of catalysts, bio-oil tends to polymerize (A. Ardiyanti, Ph.D., University of Groningen (2013)).

It is thought that the most important precursors to coke formation are the lignin-derived phenolic compounds (X. Li, et al., *Fuel*, 116: 642-649 (2014), which polymerize to heavy phenolic oligomers that dehydrate to coke[18] and cause rapid catalyst deactivation (J. Wildschut, et al., *Applied Catalysis B: Environmental*, 99: 298-306 (2010); J. Wildschut, PhD, University of Groningen, (2009)). Unfortunately, these polymerization/condensation reactions are accelerated by the elevated temperatures typically employed in hydroprocessing (F. Huang, et al., *Chemical Engineering & Technology*, 33: 2082-2088 (2010) making conventional hydroprocessing of raw bio-oil counterproductive to achieving high carbon yields of fuel-range molecules.

Researchers have attempted to stabilize bio-oil at "milder" hydroprocessing conditions. For example, Baker and Elliott (E. G. Baker and D. C. Elliott, in *Pyrolysis Oils from Biomass. Producing, Analyzing, and Upgrading*, ed. A. C. Society, American Chemical Society, Washington D.C., 376: 228-240 (1988)) reduced hydroprocessing temperature and pressure to around 274° C. and 140 bar in the presence of cobalt and molybdenum (CoMo) catalyst. Although hydrogenation occurred with a conversion of 69 vol %, the loss of water and the saturation of carbon bonds increased the viscosity of the bio-oil (as measured at 60° C.) from 10 cP to 14,200 cP. Similarly, experiments with two-stage hydroprocessing in the temperature range of 150-450° C. and 207 bar using sulfided nickel molybdenum (NiMo) and CoMo catalysts also dramatically increased the viscosity of the bio-oil, yielding a "tar-like" product (E. G. Baker and D. C. Elliott, in *Pyrolysis Oils from Biomass. Producing, Analyzing, and Upgrading*, ed. A. C. Society, American Chemical Society, Washington D.C., 376: 228-240 (1988); L. Conti, et al., in *Bio-Oil Production and Utilization*, ed. A. V. B. a. E. N. Hogan, CPL Press, Newbury, UK, 198-205 (1996)). Likewise, although bio-oil stability improved after "mild" hydrotreating at 275° C. and 152 bar using a sulfided NiMo catalyst as measured by accelerated aging, but the viscosity of the upgraded bio-oil increased one thousand fold (L. Conti, et al., in *Bio-Oil Production and Utilization*, ed. A. V. B. a. E. N. Hogan, CPL Press, Newbury, UK, pp. 198-205 (1996); L. Conti, et al., in *Developments in Thermal Biomass Conversion*, eds. B. A. V. and D. G. B. Boocock, Blackie Academic and Professional, London, pp. 622-632 (1997); J. P. Diebold, ed. N. R. E. L. (NREL), Thermalchemie, Inc., Lakewood, pp. 1-38 (2000)).

More recently, Chaiwat et al. (W. Chaiwat, et al., *Fuel*, 112: 302-310 (2013)) performed a series of "mild hydroprocessing" studies on bio-oil (i.e., 250° C. and 56-62 bar pressure for 3.0 hours produced 7.8 wt % oil phase, 44.7 wt % water phase, and 20.2 wt % heavy compounds; 200° C. and 57-64 bar pressure for 3 hours produced 21.2 wt % oil phase, 43.3 wt % water phase, and 16.6 wt % heavy compounds). It was not clear whether the heavy compounds were suitable for hydrocracking to fuel range molecules. However, even if the heavy compounds were suitable, the yield of potentially upgradable compounds was clearly unacceptably low for commercial applications.

Additionally, a three-stage process for hydrotreating bio-oil was developed (S. B. Jones, et al., *Production of Gasoline and Diesel from Biomass via Fast Pyrolysis, Hydrotreating and Hydrocracking: A Design Case*, Pacific Northwest National Laboratory, Richland (2009)). The first two stages, characterized as hydrotreating at 240° C., 170 bar and 370° C., 137 bar, respectively, were intended to partially deoxygenate and stabilize the bio-oil followed by more severe hydrocracking/hydrodeoxygenation at 425° C., 87 bar to produce fuel-range hydrocarbon molecules (S. B. Jones, et al., *Production of Gasoline and Diesel from Biomass via Fast Pyrolysis, Hydrotreating and Hydrocracking: A Design Case,* Pacific Northwest National Laboratory, Richland (2009)). However, carbon yields under these conditions remained modest and rapid coking of catalysts remained a problem.

The present invention is directed to overcoming these and other deficiencies in the art.

SUMMARY OF THE INVENTION

One aspect of the invention relates to a method for upgrading bio-oil or a bio-oil fraction comprising providing a bio-oil or bio-oil fraction and providing hydrogen (H2). The bio-oil or bio-oil fraction and hydrogen are reacted in the presence of a catalyst at a temperature of less than 150° C. and a pressure of less than 100 bar (absolute) to produce a hydrogenated liquid oil at a carbon yield of over 75%.

Another aspect of the present invention relates to a method for upgrading bio-oil or a bio-oil fraction comprising providing a bio-oil or bio-oil fraction and providing oxygen reducing reaction conditions. The bio-oil or bio-oil fraction is reacted under the oxygen reducing reaction conditions at low temperature and/or low pressure to produce an upgraded bio-oil product containing fewer carbonyl groups than the bio-oil or bio-oil fraction.

The present invention also relates to a method for upgrading bio-oil or a bio-oil fraction comprising providing a bio-oil or bio-oil fraction and providing a solution comprising one or more fermentation organisms a sugar source. The solution and bio-oil or bio-oil fraction are combined to obtain a fermentation mixture comprising the bio-oil, the sugar source, and the one or more fermentation organisms. The fermentation mixture is incubated at 15° C. to 30° C. for 16 hours to 72 hours to produce an upgraded bio-oil fermentation product containing fewer carbonyl groups than the bio-oil or bio-oil fraction.

Bio-oil contains lignin-derived phenolic oligomers, which have the potential to be used for resins, adhesives, plastics, carbon fibers, fuel oil and numerous other applications. However, phenolic oligomers contain both conjugated and nonconjugated carbon-carbon double bonds (vinyl groups) as well as carbon-oxygen double bonds (carbonyl groups) that are reactive, such that they can readily polymerize and dehydrate when hydroprocessed, resulting in low carbon yields of fuel range molecules and deactivation of hydroprocessing catalysts.

Hydrogenation can break these double bonds, but conventional hydroprocessing, even so-called "mild" hydroprocessing, as previously reported in the literature, is too severe for the reactive feedstocks derived from biomass. Thus, attempts at catalytic upgrading to date have resulted in significantly reduced yields, coking of the catalyst and/or increased viscosity, all of which render the bio-oil not suitable for use as a fuel oil or other industrial applications.

The present invention utilizes low temperature, low pressure (LTLP) hydrogenation of bio-oil or a bio-oil fraction to produce a stable, low viscosity product at high yields. The methods of the present invention can be used to upgrade and/or stabilize bio-oil or a bio-oil fraction.

As demonstrated in the examples below, LTLP hydrogenation of phenolic oligomers derived from bio-oil converts carbonyl bonds to alcohols and saturates vinyl groups to aliphatic groups with virtually no coking (see Example 1). LTLP hydrogenation is also able to dramatically reduce the viscosity of the phenolic oligomer samples, despite only small reductions in the molecular weight of the starting material. The reduction in viscosity was attributed to the self-solvating power of the alcohols formed during hydrogenation. These results are in contrast with more conventional "mild hydroprocessing," which occurs at much higher temperatures and pressures than employed in the present study. These more severe conditions, practiced in the prior art, promote complete saturation of carbon-carbon bonds as well as deoxygenation of functional groups such as carboxylic acids, ketones, and aldehydes. Without the production of alcohols, the saturation of carbon-carbon bonds leads to the classical viscosity thickening observed for hydrogenation of lipids and severely hydroprocessed bio-oil. The absence of coking during LTLP hydrogenation suggests that these mild conditions promote hydrogenation of the phenolic oligomers over their polymerization, which is ultimately responsible for coke formation.

An example is also provided below to show that LTLP hydrogenation experiments can be performed to whole or crude bio-oil as well as bio-oil fractions collected from condenser and electrostatic precipitator stages of the bio-oil collection system (e.g., stage fractions (SFs) 1, 2, 3, 4, and 5, or combinations thereof). The LTLP hydrogenation can separate the light oxygenates from the phenolics for specific end-use. By treating these bio-oil streams with LTLP hydrogenation, specific catalysts can be used for upgrading and/or separating streams for specialty chemical separation and industrial use.

In particular, the methods disclosed herein solve the problems associated with using conventional hydroprocessing to upgrade bio-oil that occur due to the high temperatures and pressures used to upgrade. In particular, the inventors have discovered that dramatic mass losses, coking, and catalyst deactivation do not become an issue when bio-oil or a bio-oil fraction is upgraded under mild conditions (i.e., temperatures less than 150° C. and/or pressure less than 100 bar). For example, mild hydrogenation stabilizes bio-oil or a bio-oil fraction by adding hydrogen to very unstable vinyl groups (C═C) in lignin-derived phenolic based bio-oil and drastically reduces viscosity by converting a portion of the carbonyls (C═O) to alcohols. This ultimately eliminates coking and polymerization allowing the oil to be sprayed using nozzles, which is important in fuel oil applications. The product from mild hydrogenation can be used for current fuel oil applications (e.g., both firing/co-firing with petroleum based fuel oil).

Further upgrading reactions, e.g., Clemmensen reduction and fermentation by a microorganism (e.g., yeast), performed at mild temperatures and/or pressures remove most carbonyls (C═O), thus further stabilizing the bio-oil.

Thus, the present invention discloses novel low temperature and/or low pressure techniques (e.g., up to 150° C. and 100 bar) that can be used to upgrade bio-oil or a bio-oil fraction, which substantially eliminates polymerization and dehydration reactions that lead to coking of catalysts and, thus, results in high carbon yields (e.g., over 75%). The present application includes three examples to illustrate this concept. Firstly, a mild hydrogenation technique to stabilize the phenolic oligomeric compounds found in the water-insoluble fraction of the heavy ends of pyrolysis liquids (bio-oil) has been performed. Secondly, a method utilizing zinc (Zn) and hydrochloric acid (HCl) at −20° C. to 0° C. was utilized to remove carbonyl groups (C═O) for upgrading purposes. Thirdly, yeast was used to convert carbonyls to alcohols and ethers at 21° C.

These mild conditions, which are close to ambient temperature and atmospheric pressure, simplify the process, dramatically reduce capital and operating costs for the system and produce higher yields of organic liquids and virtually no coking of catalysts.

The upgraded bio-oil produced according to the methods provided herein may be used to obtain improved yields of an upgraded, stabilized bio-oil product for further upgrading and/or suitable for use in current fuel oil applications or other applications that use phenolic oligomers, e.g., resins, adhesives, plastics, carbon fibers.

BRIEF DESCRIPTION OF THE DRAWINGS

FIG. 3A shows the FTIR spectra of untreated and hydrogenated cornstover-derived stage fraction 1 phenolic oligomers (CS SF1 PO). FIG. 3B shows the FTIR spectra of untreated and hydrogenated cornstover-derived stage fraction 2 PO (CS SF2 PO).

FIG. 4A shows the $^1$H NMR spectra of CS SF1 PO and CS SF2 PO before and after hydrogenation, while FIG. 4B shows the $^1$H NMR spectra of RO SF1 PO and RO SF2 PO before and after hydrogenation.

FIG. 6A shows the HSQC spectra of CS SF1 bio-oil, and FIG. 6B shows the HSQC spectra of hydrogenated CS SF1 bio-oil. The loss of ethers, esters, and vinyls is seen in the hydrogenated sample.

FIG. 8 is a graph comparing the $^1$H NMR spectra of SF1 PO after hydrogenation (B) and SF1 PO after hydrogenation and reduction (decarbonylation using Zn) (C), illustrating the further loss of aromatics and aliphatics. The $^1$H NMR spectra of SF1 PO absent any upgrading (A) is also shown.

FIG. 10 is a graph comparing the $^1$H NMR spectra of SF1 PO (A), hydrogenated SF1 PO (B), product (a), i.e., dry yeast precipitate, from hydrogenated SF1 PO subject to fermentation with Baker's yeast (16 hour) (C), product (b), i.e., hexane soluble, from hydrogenated SF1 PO subject to fermentation (D), and product (c), i.e., ethyl acetate soluble, from hydrogenated SF1 PO subject to fermentation (E). Products (a), (b), and (c) contain different types of compounds, which are evident in the spectra.

FIGS. 15A-E are graphs showing the gas chromatography/mass spectrometry (GC/MS) results of stage fraction (SF) 3. FIG. 15A shows SF 3 prior to hydrogenation. FIG. 15B shows control distillate sample (distilled without hydrogenation of SF 3). FIG. 15C shows control raffinate sample (distilled without hydrogenation of SF 3). FIG. 15D shows hydrogenated SF 3 distillate (5% $H_2$, 25° C., 1 bar, 10% Pd/C). FIG. 15E shows hydrogenated SF 3 raffinate (5% $H_2$, 25° C., 1 bar, 10% Pd/C). Note: the compound identifications for all results in FIGS. 15A-E were obtained from NIST library.

FIG. 16A shows SF 4 prior to hydrogenation. FIG. 16B shows the control non-hydrogenated SF 4 distillate sample. FIG. 16C shows the hydrogenated SF 4 distillate sample (5% $H_2$, 25° C., 1 bar, 10% Pd/C). FIG. 16D shows the hydrogenated SF 4 raffinate sample (5% $H_2$, 25° C., 1 bar, 10% Pd/C).

FIGS. 17A-C are graphs showing the GC/MS results of stage fraction (SF) 5. FIG. 17A shows SF 5 prior to hydrogenation. FIG. 17B shows the hydrogenated SF 5 organic sample (separated from the aqueous phase via rotary evaporation at 40° C.). FIG. 17C shows the hydrogenated SF 5 aqueous sample (separated from the organics via rotary evaporation at 40° C.).

FIGS. 18A-C are graphs comparing NMR spectra of the whole bio-oil (non-hydrogenated) (FIG. 18A), the hydrogenated whole bio-oil using methanol as a solvent during hydrogenation (FIG. 18B), and the hydrogenated whole bio-oil using no solvent (NS) during hydrogenation (FIG. 18C).

DETAILED DESCRIPTION OF THE INVENTION

Figure 1:
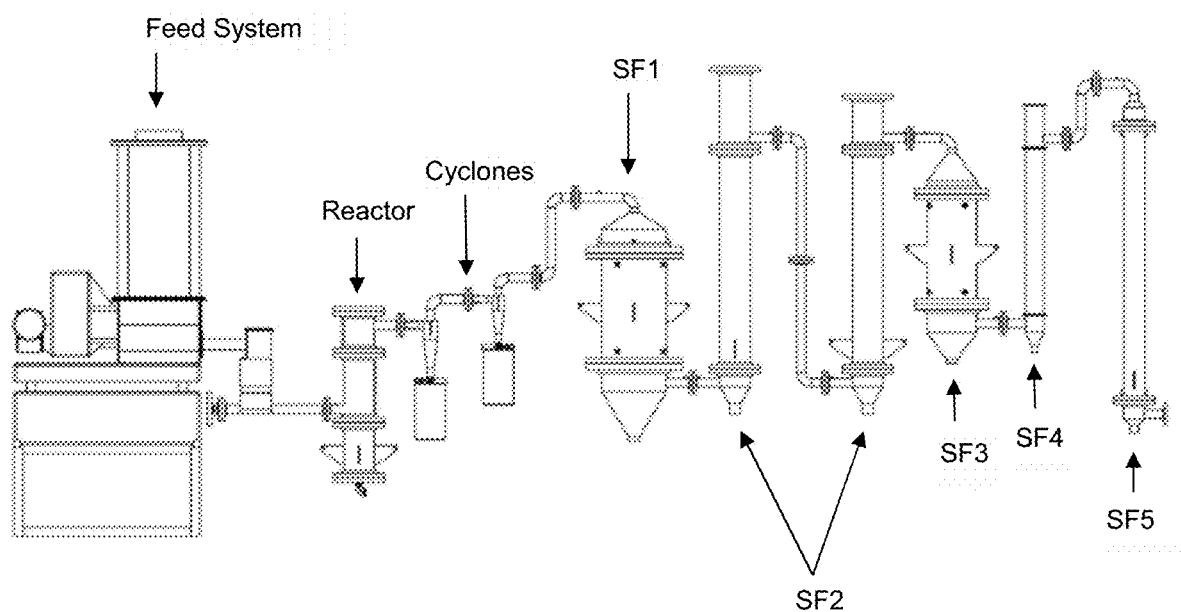
FIG. 1 is a schematic drawing showing the fast pyrolysis reactor and the five stage fractions (SF) of bio-oil recovery utilized to carry out the present invention.

The present invention generally relates to methods for upgrading and/or stabilize whole or fractionated bio-oil under mild conditions, i.e., low temperature and/or low pressure. The methods include hydrogenating bio-oil or a bio-oil fraction under low temperature and/or pressure conditions; reacting bio-oil or a bio-oil fraction under the oxygen reducing reaction conditions at low temperature and/or low pressure; and/or performing microbial fermentation of the bio-oil or bio-oil fraction under low temperature and/or pressure conditions. The upgraded bio-oil produced according to these methods may be stabilized, e.g., by removal of vinyl and/or carbonyl groups, for further processing and/or suitable for use in current fuel oil applications or other applications utilizing phenolic oligomers.

The methods of the present invention can be used to upgrade and/or stabilize bio-oil or a bio-oil fraction.

Upgrading of Bio-oil or a Bio-oil Fraction at Low Pressure and/or Low Temperature One aspect of the invention relates to a method for upgrading bio-oil or a bio-oil fraction comprising providing a bio-oil or bio-oil fraction and providing hydrogen ($H_2$). The bio-oil or bio-oil fraction and hydrogen are reacted in the presence of a catalyst at a temperature of less than 150° C. and a pressure of less than 100 bar (absolute) to produce a hydrogenated liquid oil at a carbon yield of over 75%.

In some aspects, the carbon yield is over 80%, over 85%, over 90% or over 95% (molar percent carbon in PO).

Alternatively, the carbon yield of hydrogenated liquid oil from whole or fractionated bio-oil treated according to the methods provided herein is over 0.06 db, over 0.065 db, over 0.07 db, 0.075 db or 0.08 db (mole/g in bio-oil). This unit of measurement, i.e., mole/g bio-oil (db), provides a direct comparison with carbon yields reported by other researchers. See Table 2. In all instances, substantially no (or very little) coking and/or carbon gas loss was encountered in obtaining hydrogenated liquid oil according to the LTLP hydrogenation of whole or fractionated bio-oil described herein.

In a particular aspect, the bio-oil or bio-oil fraction and hydrogen are reacted in the presence of a catalyst at a temperature of 10° C. to 100° C. and/or a pressure of 0.05 bar (absolute) to 50 bar (absolute) to produce a hydrogenated liquid oil at a carbon yield of over 75%, over 80%, over 85%, or over 90%.

In a specific embodiment, the hydrogenation reaction is carried out at a temperature of 15° C. to 50° C. and a pressure of 0.5 bar (absolute) to 10 bar (absolute).

Non-limiting examples of suitable catalysts may include one or more transition metals from group 3 to group 12, more specifically metals comprising group 9 or 10 metals, for example cobalt or palladium, respectively, or a platinum group metal (e.g., palladium, platinum, rhodium, ruthenium, iridium and osmium).

Preferred catalysts are based on palladium, preferably supported on porous carbon. Although a mono-metallic catalyst of the group 10 metal, e.g., Pd based catalyst, is preferred, a bi-metallic catalyst (e.g., Ni—Zr, Ni—Ce, Ni—Ce—Zr, Ni—Cr, Ni—Mo, Ni—W, Ni—Mn, Ni—Re, Ni—Fe, Ni—Ru, Ni—Cu, Co—Mo) can also be used.

In one aspect, the catalyst comprises Pd, Ru, Ru+Pd, Pt, Raney Ni, Ni, CoMo, or NiMo. Preferably, the catalyst comprises Pd. More preferably, the catalyst is palladium on activated carbon (Pd/C).

For example, the 10% Pd/C catalyst used for hydrogenation of SF1 PO and SF2 PO (see Example 1) was chosen for, e.g., high activity, mild process conditions, carbon support availability, and the recovery the Pd metal by simply burning off the carbon support (J. Panpranot, et al., *Applied Catalysis A: General*, 292: 322-327 (2005); T. Harada, et al., *Journal of Molecular Catalysis A: Chemical*, 268: 59-64 (2007); N. Numwong, et al., *Chemical Engineering Journal*, 210: 173-181 (2012), which are hereby incorporated by reference in their entirety).

Support materials are chosen to bring the active (metal) phase of the catalyst into contact with reactants. Non-limiting examples of suitable catalyst support materials include one or more of, e.g., carbon supports, alumnia supports, silica supports titanium supports, zirconia supports, niobium pentoxide materials and calcium supports. In particular, exemplary supports for the catalyst include, but are not limited to, C, $Al_2O_3$, $SiO_2$, $Al_2O_3+SiO_2$, $CaCO_3$, $TiO_2$, $ZrO_2$, and $Nb_2O_5$.

Preferably, the support material is porous carbon (such as activated carbon). This support shows no tendency to hydrolyze and deteriorate in water and acid rich environments. A further benefit of carbon-supported catalyst is the low cost of the carbon support and the ability of recovering the metals from spent catalysts by simply burning off the carbon, rather than more expensive refining or recovery processes.

The resulting hydrogenated bio-oil has a lower viscosity than the non-hydrogenated bio-oil (e.g., at least 45%, at least 50%, at least 55%, at least 60%, at least 65%, at least 70%, at least 75%, or at least 80% less viscous than the non-hydrogenated bio-oil);

Given the efficient recovery of carbon using the LTLP hydrogenation methods disclosed herein, i.e., about 60-100% of carbon is returned from the feed, the hydrogenated liquid oil contains substantially no coke and/or substantially no carbon gases and/or substantially no polymerization of phenolic molecules.

Additionally, the hydrogenated bio-oil may contain fewer vinyl groups, ether groups, and/or aldehydes than the untreated (non-hydrogenated) bio-oil.

Moreover, the hydrogenated bio-oil may contain increased aliphatics, phenolic monomers, and/or alcohols compared to the untreated (non-hydrogenated) bio-oil.

In some aspects, the bio-oil or fractionated bio-oil is upgraded by only hydrogenation, i.e., no additional upgrading steps are performed to further stabilize the bio-oil.

However, in addition to hydrogenation, whole bio-oil or fractionated bio-oil can be further upgraded to reduce the presence of reactive groups, e.g., by reacting the hydrogenated bio-oil (whole or fractionated) with zinc and hydrochloric acid at a temperature of less than 0° C., as described in more detail infra. In one aspect, hydrogenated bio-oil can be further processed by such reaction with Zn and HCl. Moreover, whole bio-oil or fractionated bio-oil can be further upgraded to reduce the presence of reactive carbonyl groups by fermentation.

Another aspect of the present invention relates to a method for upgrading bio-oil or a bio-oil fraction comprising providing a bio-oil or bio-oil fraction and providing oxygen reducing reaction conditions (e.g., conditions that reduce carbonyls present in components of bio-oil or a bio-oil fraction to alcohols and/or alkanes). The bio-oil or bio-oil fraction is reacted under the oxygen reducing reaction conditions at low temperature and/or low pressure to produce an upgraded bin-oil product containing fewer carbonyl groups than the bio-oil or bio-oil fraction.

Any number of oxygen reducing reactions may be used at low temperature and/or low pressure to reduce carbonyls to alcohols and/or alkanes. Suitable catalysts for use in these oxygen reducing reactions include, but arc not limited to, $PtO_2$, Pt, Pd/C, LiAlH4, $NaBH_4$, DIBAL-H, $BH_3$, $NH_2NH_2$ (Hydrazine), Thioacetal/Raney Ni, $Et_3SiH$.

In one aspect, the method comprises providing a bio-oil or bio-oil fraction and providing zinc (Zn) and hydrochloric acid (HCl). The bio-oil or bio-oil fraction is reacted with the Zn and HCl at a temperature of less than 0° C. to produce an upgraded bio-oil product containing fewer carbonyl groups than the bio-oil or bio-oil fraction. This particular embodiment utilizes a modified Clemmensen reduction, which is performed under mild conditions (0° C. for 1-2 hours) to upgrade (whole or fractionated) bio-oil by reducing ketones found in bio-oil. See Example 2.

In some aspects, the bio-oil or fractionated bio-oil is upgraded by only treatment with Zn and HCl under the conditions specified infra, i.e., no additional upgrading steps are performed to further stabilize the bio-oil. However, in other aspects, in addition to reducing carbonyl groups using oxygen reducing reactions, e.g., treatment with Zn and HCl at a temperature of less than 0° C., whole bio-oil or fractionated bio-oil can be further upgraded to reduce the presence of reactive groups, e.g., by hydrogenation in the presence of a catalyst at a temperature of 10° C. to 100° C. and/or a pressure of 0.05 bar (absolute) to 50 bar (absolute) and/or fermentation as set forth in detail below.

The present invention also relates to a method for upgrading bio-oil or a bio-oil fraction comprising providing a bio-oil or bio-oil fraction and providing a solution comprising one or more fermentation organisms a sugar source. The solution and bio-oil or bio-oil fraction are combined to obtain a fermentation mixture comprising the bio-oil, the sugar source, and the one or more fermentation organisms. The fermentation mixture is incubated at 15° C. to 30° C. for 16 hours to 72 hours to produce an upgraded bio-oil fermentation product containing fewer carbonyl groups than the bio-oil or bio-oil fraction.

Fermentation may be performed using any microbe capable of reducing undesirable chemical groups, e.g., carbonyl groups, contained in bio-oil (whole or fracitonated). The micrboes may be naturally-occurring or modified, e.g., genetically modified, to promote fermentation of bio-oil. Non-limiting example of microbes that may be suitable for use in the LTLP fermentation methods disclosed herein include, but are not limited to, *Geobacter* spp., *Cellulomonas* spp., *Saccharomyces* spp., *Schizosaccharomyces* spp., *Pichia* spp., and *Cyanobacteria* spp. In particular, the one or more fermentation organisms is/are selected from *Saccharomyces cerevisiae*, *Schizosaccharomyces pombe*, or *Pichia stipitis*.

Fermentable sugar obtained from lignocellulosic material exhibits potential as a renewable feedstock for the production of bio-fuels. A potentially viable source of fermentable sugars is bio-oil. Depending on the type of lignocellulosic material used and the operating conditions for the process of pyrolysis, bio-oil can contain up to 33 wt % of 1,6-anhydro-β-D-glucopyranose (levoglucosan, LG), an anhydrosugar that can be readily hydrolyzed to glucose. Fermentation by microbes (e.g., bacteria, yeast, algae and/or molds) can be used to modify the components of bio-oil to generate a more stable bio-oil product.

Non-limiting exemplary sugar sources for used in the methods disclosed herein include, but are not limited to, glucose, fructose, sucrose, maltose, maltotriose or other fermentable sugar feed.

In some aspects, the bio-oil or fractionated bio-oil is upgraded by only fermentation as set forth infra, i.e., no additional upgrading steps are performed to further stabilize the bio-oil. However, in other aspects, in addition to reducing carbonyl groups by incubating the bio-oil (whole or fracitonated) with a solution comprising one or more fermentation organisms a sugar source and then incubating the mixture at 15° C. to 30° C. for 16 hours to 72 hours to produce an upgraded bio-oil fermentation product containing fewer carbonyl groups than the bio-oil, the bio-oil can be further upgraded to reduce the presence of reactive groups, e.g., by hydrogenation in the presence of a catalyst at a temperature of 10° C. to 100° C. and/or a pressure of 0.05 bar (absolute) to 50 bar (absolute) and/or treatment with Zn and HCl at a temperature of less than 0° C.

Production of Bio-oil

The methods of the present invention can be used to treat "bio-oil" or a "bio-oil fraction" to upgrade or stabilize them. The bio-oil can be a whole or crude bio-oil recovered directly from pyrolysis of a biomass. The bio-oil fraction can be recovered from the pyrolysis of a biomass at different stages. Bio-oil fractions can be recovered from the product of a biomass at different stages, such as stage fraction 1 (SF1), stage fraction 2 (SF2), stage fraction 3 (SF3), stage fraction 4 (SF4), stage fraction 5 (SF5), or combinations thereof. The components in the different stage fractions are described infra.

Bio-oil can be obtained from a variety of biomass types. Biomass is biological material from living, or recently living organisms. Biomass can be in the form of products, by-products, and/or residues of the forestry and agriculture industries. Biomass includes, but is not limited to, forest and mill residues, agricultural crops and wastes, wood and wood wastes, animal wastes, livestock operation residues, aquatic plants, fast-growing trees and plants, and municipal and industrial wastes. The crop residues that can be used for the present invention include materials such as, e.g., corn stover. Biomass can include cellulose, hemicelluose, and/or lignin. Lignocellulosic biomass typically refers to plant biomass. Typically, lignocellulosic biomass can include cellulose, hemicelluose, and/or lignin.

Bio-oil can be recovered, for example, by fast pyrolysis of biomass. Pyrolysis is the thermochemical decomposition of biomass at elevated temperatures (typically around 300 to 550° C.) in the absence of oxygen. One method of obtaining bio-oil from fast-pyrolysis of biomass is described in Pollard et al., "Characterization of Bio-oil Recovered as Stage Fractions with Unique Chemical and Physical Properties," *J. Anal. Appl. Pyrolysis* 93: 129-139 (2012), which is hereby incorporated by reference in its entirety. It teaches a bio-oil recovery system that recovers bio-oil as distinctive stage fractions while eliminating many of the problems associated with traditional condenser based bio-oil recovery systems. When treated at these temperatures, biomass decomposes to three primary products: charcoal, bio-oil, and gases (e.g., CO, $H_2$, $CO_2$, and $CH_4$).

Bio-oil is a mixture of water, light volatiles, and non-volatiles and is highly reactive because of the presence of significant quantities of oxygen. The bio-oil is a complex mixture of chemical species that result from the decomposition of cellulose, hemicellulose, and lignin. There are over 300 compounds, including, but not limited to, hydroxyaldehydes, hydroxyketones, sugars, carboxylic acids, and phenolics. The abundance of these chemical species in bio-oil makes it similar to crude petroleum oil and, thus, an attractive resource for obtaining chemicals and fuels.

The various bio-oil fractions contain a variety of chemical species including, without limitation, furans, minor carbohydrates, acetic acid, levoglucosan, water insoluble compounds, water, syringols, guaiacols, phenols, hydroxyaldehyde, hydroxyketones, solids, other sugars, and phenolic compounds.

The method of the present invention can be used to treat crude (i.e., whole) or fractionated bio-oil. The fractions of fractionated bio-oil may be those described in U.S. patent application Ser. No. 12/551,103 to Brown, et al., which is hereby incorporated by reference in its entirety.

The first liquid fraction (SF1) (see FIG. 1) collected from crude bio-oil is high in water insolubles and anhydrosugars. This fraction is typically recovered in a condenser operated in accordance with U.S. patent application Ser. No. 12/551,103 to Brown, et al. which is hereby incorporated by reference in its entirety. There is also a small amount of water, between 3-7%. The percentage of water insoluble components can range from 50-75% (largely dependent on the biomass that was used). The water insolubles are thought to come from the lignin in the biomass. The first fraction of bio-oil also contains between 5-15% levoglucosan, a 6 carbon anhydrous sugar. The amount of levoglucosan is a function of biomass and reactor operating conditions. The bio-oil condensation product composition at the first stage comprises furans having a weight percentage in the range of 2 to 7%; minor carbohydrates having a weight percentage in the range of 0 to less than 5%; acetic acid having a weight percentage in the range of 0 to less than 4%; levoglucosan having a weight percentage in the range of 5 to 15%; water insoluble compounds having a weight percentage in the range of 50 to 75%; water having a weight percentage in the range of 3 to 7%; syringols having a weight percentage in the range of 0 to less than 5%; guaiacols having a weight percentage in the range of 3 to 7%; and phenols having a weight percentage in the range of 1 to 7%.

The second liquid fraction (SF2) (see FIG. 1) collected from crude bio-oil is very similar to the first fraction (i.e. the bio-oil condensation product composition at the second stage comprises furans having a weight percentage in the range of 2 to 7%; minor carbohydrates having a weight percentage in the range of 0 to less than 5%; acetic acid having a weight percentage in the range of 0 to less than 4%; levoglucosan having a weight percentage in the range of 5 to 15%; water insoluble compounds having a weight percentage in the range of 50 to 75%; water having a weight percentage in the range of 3 to 7%; syringols having a weight percentage in the range of 0 to less than 5%; guaiacols having a weight percentage in the range of 3 to 7%; and phenols having a weight percentage in the range of 5 to 10%). This fraction is typically recovered in an electrostatic precipitator operated in accordance with U.S. patent application Ser. No. 12/551,103 to Brown, et al. which is hereby incorporated by reference in its entirety.

The third liquid fraction (SF3) (see FIG. 1) collected from crude bio-oil is a mixture of many different components. This fraction is typically recovered in a condenser operated in accordance with U.S. patent application Ser. No. 12/551,103 to Brown, et al. which is hereby incorporated by reference in its entirety. The key to the third fraction is the high percentage of phenols. This can be anywhere from 10-18% of this fraction of bio-oil. This fraction has 5-15% water as well. The bio-oil condensation product composition at the third stage comprises furans having a weight percentage in the range of 6 to 12%; minor carbohydrates having a weight percentage in the range of 10 to 20%; acetic acid having a weight percentage in the range of 0 to less than 5%; levoglucosan having a weight percentage in the range of 0 to less than 4%; water insoluble compounds having a weight percentage in the range of 10 to 20%; water having a weight percentage in the range of 5 to 15%; syringols having a weight percentage in the range of 3 to 10%; guaiacols having a weight percentage in the range of 7 to 15%; and phenols having a weight percentage in the range of 10 to 18%.

The fourth liquid fraction (SF4) (see FIG. 1) collected from crude bio-oil is very similar to the third fraction. This fraction is typically recovered in an electrostatic precipitator operated in accordance with U.S. patent application Ser. No. 12/551,103 to Brown, et al. which is hereby incorporated by reference in its entirety. There is a high percentage of phenols and acetic acid (5-18%). This fraction can also be between 5-20% water. This fraction will collect mainly low molecular weight compounds and a low percentage of water insoluble compounds. The bio-oil condensation product composition at the fourth stage comprises furans having a weight percentage in the range of 6 to 12%; minor carbohydrates having a weight percentage in the range of 10 to 20%; acetic acid having a weight percentage in the range of 5 to 15%; levoglucosan having a weight percentage in the range of 0 to less than 4%; water insoluble compounds having a weight percentage in the range of 10 to 25%; water having a weight percentage in the range of 5 to 20%; syringols having a weight percentage in the range of 3 to 10%; guaiacols having a weight percentage in the range of 7 to 15%; and phenols having a weight percentage in the range of 10 to 18%.

The fifth liquid fraction (SF5) (see FIG. 1) collected from crude bio-oil is a watery fraction that is rich in low molecular weight compounds. This fraction is typically recovered in a condenser operated in accordance with U.S. patent application Ser. No. 12/551,103 to Brown, et al. which is hereby incorporated by reference in its entirety. This fraction contains more than 55% water and is low in water insolubles and solids (<1% each). This fraction also contains a large amount of acetic acid (5-15%). The bio-oil condensation product composition at the fifth stage comprises furans having a weight percentage in the range of 0 to less than 5%; minor carbohydrates having a weight percentage in the range of 8 to 15%; acetic acid having a weight percentage in the range of 5 to 15%; hydroxyacetaldehyde having a weight percentage in the range of 0 to less than 4%; water insoluble compounds having a weight percentage in the range of 0 to less than 1%; water having a weight percentage in the range of 56 to 90%; guaiacols having a weight percentage in the range of 0 to less than 3%; and phenols having a weight percentage in the range of 0 to less than 5%.

The "heavy ends" contain mostly sugar monomers and oligomers derived from carbohydrate and phenol oligomers derived from lignin found in the biomass. The sugars are mostly water soluble while the phenolic oligomers are water insoluble. The heavy ends are dark, viscous liquid which sometimes cools to a vitreous solid. The present invention exploits the difference in solubility between the carbohydrate and lignin-derived compounds and provides a method for washing the sugars from the insoluble fraction with flow properties superior to the original heavy fraction. The sugars can be subsequently clarified and vacuum distilled to yield "pyrolytic sugars."

The elemental composition of these liquid fractions is shown in Table 1 as follows:

TABLE 1

Elemental Compositions Analysis of the Different Fractions

| Ultimate Analysis | SF1 (Condenser) | SF2 (ESP) | SF3 (Condenser) | SF4 (ESP) | SF5 (Condenser) |
|---|---|---|---|---|---|
| Carbon | 55-65 | 55-65 | 45-60 | 40-50 | 15-25 |
| Hydrogen | 5-10 | 5-10 | 5-10 | 5-10 | 5-10 |
| Nitrogen | <1% | <1% | <1% | <1% | <1% |
| Sulfur | <1% | <1% | <1% | <1% | <1% |
| Oxygen (by difference) | 25-40 | 25-40 | 40-50 | 40-60 | 70-80 |
| Ash | <1% | <1% | <1% | <4% | <1% |
| Karl Fischer Analysis (% Moisture) | 3-7% | 3-7% | 5-15% | 5-20% | >55% |
| % Water Insolubles | 50-75% | 50-75% | 10-20% | 10-25% | <1% |
| % Solids | <3% | <3% | <1% | <1% | <1% |
| TAN (mg KOH/gram bio-oil) | 30-40 | 25-50 | 60-75 | 110-130 | 60-160 |
| Higher Heating Value (MJ/kg) | 23-26 | 23-27 | 21-24 | 19-22 | 5-10 |
| Viscosity (cSt) | 1000-2000 | 3000-6000 | 50-100 (40° C.) | 100-150 (40° C.) | 1-2 (40° C.) |

A useful system for carrying out the method of the present invention is exemplified in FIG. 1. As shown in this figure, biomass is withdrawn from the feed system and fed in to the reactor, where it is charged while fluidizing gas is provided. Exiting pyrolysis product gas passes through the cyclones.

Solids removed by the cyclones are collected in containers, while vapors are withdrawn for recovery of bio-oil liquid fractions as described above. The first and second stage of the reactor (SF1 and SF2, respectively) condense≥30-50% of the produced bio-oil and contain the largest majority of the produced phenolic compounds. These two stages also contain the lowest percentage of water of any of the stages (2.0-7.0%) derived from the biomass feedstock and formed as a by-product as a result of pyrolysis reactions.

The present invention may be further illustrated by reference to the following examples.

EXAMPLES

The following examples are intended to illustrate, but by no means are intended to limit, the scope of the present invention as set forth in the appended claims.

Example 1

Hydrogenation of Bio-Oil Under Mild Conditions

Materials and Methods

Figure 2:
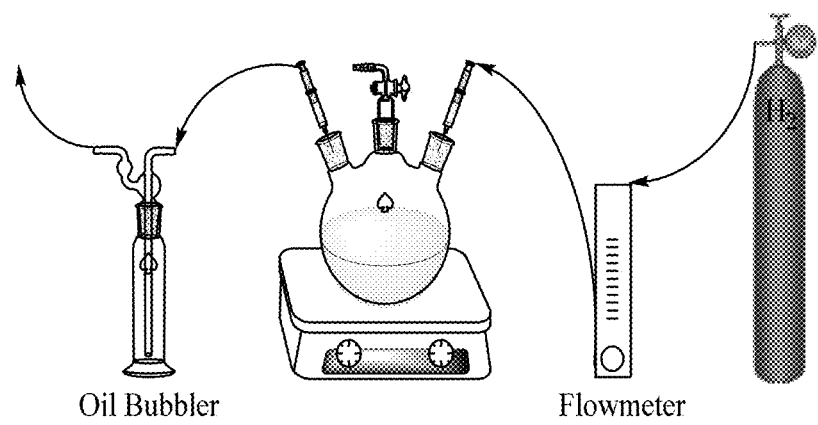
FIG. 2 is a schematic drawing showing the set-up for hydrogenation of bio-oil phenolic oligomers (PO).

Hydrogenation experiments were performed on phenolic oligomers obtained from the heavy ends (higher molecular weight species) of bio-oil collected from condenser and electrostatic precipitator stages of the bio-oil collection system, which are designated respectively as SF1 PO and SF2 PO. The experimental set-up for hydrogenation is shown in FIG. 2.

The phenolic oligomers from these two stage fractions were produced from corn stover (CS) that had been in cold storage (5° C.) for 6 months and red oak (RO) that was hydrogenated immediately after its production. Biomass was passed through a 60 hp hammer mill equipped with a 3 mm screen, resulting in a particle range of approximately 200 micron to 3 mm.

Fast pyrolysis was performed utilizing a fluidized bed reactor with a staged bio-oil recovery system (FIG. 1). See, e.g., A. S. Pollard, et al., *Journal of Analytical and Applied Pyrolysis*, 93: 129-138 (2012); M. R. Rover, et al., *Journal of Analytical and Applied Pyrolysis*, 105: 262-268 (2014), which are herein expressly incorporated by reference in their entirety).

Stage 1, a condenser, collects the high boiling point compounds (i.e. levoglucosan, phenolic oligomers) with the temperature controlled utilizing a shell-and-tube heat exchanger operated with gas inlet and outlet temperatures of 345° C. and 102° C., respectively. Stage 2 is an electrostatic precipitator that collects aerosols formed during pyrolysis or during cooling in Stage 1. It is operated at 40 kVDC and heat traced to 129° C. to prevent premature vapour condensation (M. R. Rover, et al., *Journal of Analytical and Applied Pyrolysis*, 105: 262-268 (2014), which is herein expressly incorporated by reference in its entirety). One of the many advantages of this condenser system is that the sugars are collected in SF1 and SF2 and ultimately removed utilizing a water wash. The bio-oil remaining after the wash is comprised of less viscous POs derived from the lignin portion of biomass (M. R. Rover, et al., *ChemSusChem*, under review, which is herein expressly incorporated by reference in its entirety). The removal of sugars and the fact that the POs contains insignificant quantities of other constituents such as aldehydes and carboxylic acids[42] that are also known to promote instability (X. Li, et al., *Fuel*, 116: 642-649 (2014); X. Li, et al., *Fuel*, 90: 2530-2537 (2011), which are herein expressly incorporated by reference in their entirety), provide a stream of bio-oil that can be easily hydrogenated to form intermediate products that can then be further upgraded.

LTLP hydrogenation experiments were performed at 21° C. and 1 bar (absolute) pressure.

The sample size for the hydrogenation was approximately 100 g of both CS SF1 and SF2 PO, which were placed separately in a 1000 ml round bottom flask along with a large stir bar. SF1 was dissolved in 300 ml methanol and SF2 was dissolved in 500 ml methanol. The sample size for RO SF1 PO and SF2 PO was 40 g dissolved in 200 ml and 300 ml methanol, respectively. The flask was placed under vacuum 3 times to remove any oxygen present and then purged each time with argon. The catalyst (1.5 g for CS and 0.5 g for RO), 10% Pd/C, was quickly added to the round bottom flask.

The flask was again placed under vacuum and then a hydrogen atmosphere was introduced to the system. The flask was stirred at 750 rpm with hydrogen flowing at 0.25 L/m through the 1000 ml round bottom flask and out the bubbler (FIG. 2) for 16 hours in a fume hood. Upon completion of the hydrogenation, the samples were filtered with a fritted funnel using Celite® 503 and rinsed 3 times (100 ml, 50 ml, 50 ml) with methanol. The hydrogenated samples were rotary evaporated at 20° C. for 1.5 hours to remove the methanol solvent.

Proton NMR was carried out using an Agilent/Varian MR-400 (Agilent Technologies, Inc. Santa Clara, Calif.) with a narrow bore 9.4 tesla/400 MHz magnet equipped with OneNMR pulse-field-gradient probe. VNMRJ 3.0 was used for data acquisition with the MNova software (MestReNova, Escondido, Calif.) for data processing. Fourier transformed spectra were auto-phased and baseline corrected with dimethyl sulfoxide-$d_6$ (DMSO-$d_6$) solvent referenced at 2.50 ppm. Integration of the DMSO was normalized to 1.00. Subsequent integration of the various spectral regions ($\delta$ 10-8.0, 8.0-6.8, 6.8-6.4, 6.4-4.2, 4.2-3.0, 2.2-1.6, and 1.6-0.0 ppm) was performed. DMSO and residual methanol solvent peaks were subtracted from the integration set which allowed for the calculation of percent change in each region of interest.

Sample size was 10 mg sample $ml^{-1}$ DMSO solvent. Prior to adding the DMSO solvent the samples were dried with a small stream of nitrogen for 20 minutes with all samples filtered with a 0.45 micron filter. The sample size used for $^1$NMR analyses was 750 µL.

Gel permeation chromatography (GPC) was used to determine the molecular weight distribution of the phenolic oligomer-rich raffinates separated from the heavy ends of the bio-oil. The high performance liquid chromatography (HPLC) system used was a Dionex Ultimate 3000 (Sunnyvale, Calif.) equipped with a Shodex Refractive Index (RI) and Diode Array detector (DAD). The software used to control the instrument and evaluate the samples was Dionex Chromeleon version 6.8. For the GPC analyses, the eluent for the phenolic oligomers was tetrahydrofuran (THF) with two Agilent PLgel 3 µm 100 Å 300×7.5 mm and one Mesopore 300×7.5 mm. The column flow rate and temperature was 1.0 mL min-1 at 25° C. The phenolic oligomers samples were prepared using 10 mL of THF and 0.02 g of heavy ends from the bio-oil. All samples were filtered with a Whatman 0.45 µ Glass Microfiber syringe filter before analysis. The GPC standards were purchased from Agilent (Agilent Technologies, Inc. Santa Clara, Calif.). Standards used for the bio-oil calibration curve ranged from 162-3790 g $mol^{-1}$. The polystyrene standards were diluted with JT Baker GPC grade Stabilized THF.

All chemical analyses were performed on a 430 GC/FID (Bruker Corporation, Bruker Daltonics, Inc., Fremont, Calif.) fitted with a 1701 capillary column 60 meters in length, 0.25 mm inner diameter with a 0.25 mm film thickness (Phenomenex, Inc. Torrance, Calif.). The operating system used was Galaxie Chromatography Data System version 1.9.302.530 (Bruker Corporation, Bruker Daltonics, Inc., Fremont, Calif.). The carrier gas was helium (99.9995%) with a constant flow rate of 1.0 mL min$^{-1}$. The helium make-up was 25 mL min$^{-1}$, hydrogen flow at 30 mL min$^{-1}$ with an air flow of 300 mL min$^{-1}$. The oven was programmed to be held for 4 min at 45° C. and ramped at 3° C. min$^{-1}$ to 235° C. and held for 10 min for a total of 77.33 min. A sample volume of 14 was injected utilizing a Varian CP 8400 (Bruker Corporation, Bruker Daltonics, Inc., Fremont, Calif.) auto sampler with a split ratio of 1:45. Peak identification was based on calibration standards purchased from Fisher Scientific (Thermo Scientific® Hanover Park, Ill.). For each of the calibration standards, calibration lines were made by injecting a minimum of five standard solutions on the GC/FID run in triplicate. The concentration range was determined by injection of the standard solutions until a range was determined that comprised the quantified value (C. Branca, et al., *Industrial & Engineering Chemistry Research*, 42: 3190-3202 (2003), which is herein expressly incorporated by reference in its entirety).

Dynamic viscosity was accomplished using a Brookfield Viscometer model DV-II+pro rotational viscometer (Brookfield Engineering Laboratories, Inc., Middleboro, Mass.) using SC4-15. The viscometer was calibrated using Brookfield viscosity standard 500 silicone (Brookfield Engineering Laboratories, Inc., Middleboro, Mass.). A water bath was used with a temperature controller and held at 60.0±0.1° C. All sample viscosities were performed using the SC4-15 spindle at 15 rpm, except RO SF 2 PO. Its viscosity was determined at 5 rpm, because it was extremely viscous.

Moisture content of the bio-oil was determined by a MKS 500 Karl Fischer Moisture Titrator (Kyoto Electronics Manufacturing Co., LTD, Kyoto, Japan) using ASTM E203 Standard Test Method for Water Using Karl Fischer Reagent. The reagent used was Hydranal Composite 5K and the solvent was Hydranal Working Medium K purchased from Thermo Scientific® (Hanover Park, Ill.). The percent moisture of the bio-oil samples was determined in a minimum of four trials (M. R. Rover, et al., *Journal of Analytical and Applied Pyrolysis*, 104: 194-201 (2013), which is herein expressly incorporated by reference in its entirety).

The FTIR spectrometer used for all experiments was a Thermo Scientific Nicolet iS10 (Thermo Fisher Scientific Inc. Waltham, Mass.) equipped with a Smart iTR accessory. The spectrometer has the OMNIC Software operating system. Background was collected before every sample and attenuated total reflectance correction was used with 4 wavenumber resolution.

The visual appearance of the samples, dissolved in equal amounts of solvent prior to $^1$H NMR analyses, was assessed before and after hydrogenation. The samples became lighter in color as hydrogenation progressed with time. Color-producing chromophores in molecules are known to arise from conjugated double bonds (C=C); thus, the color change is visible evidence of hydrogenation of the phenolic oligomers (R. A. Day and A. L. Underwood, *Quantitavtive Analysis*, Prentice & Hall, Englewood Cliffs, 6th edn. (1974), which is herein expressly incorporated by reference in its entirety). After 16 hours of hydrogenation, there was no evidence of viscous polymeric materials in the samples, as commonly reported by other researchers using more severe hydrogenation conditions (W. Chaiwat, et al., *Fuel*, 112, 302-310 (2013); H. Ben, et al., *Fuel*, 103, 1148-1153 (2013), which are herein expressly incorporated by reference in their entirety).

Yields and properties of LTLP hydrogenated phenolic oligomers are summarized in Table 2A and compared to the yields and properties of traditionally hydroprocessed bio-oils in Table 2B. In particular, Table 2A provides the yields, hydrogen consumption, carbon content (molar), viscosity, density, average relative molecular weights, elemental analysis, and H/C and O/C ratios for products of LTLP hydrogenation of phenolic oligomers (PO) obtained from SF1 and SF2 recovered from the pyrolysis of corn stover (CS) or red oak (RO), compared to hydroprocessed bio-oils as reported in the literature in Table 2B.

TABLE 2

Comparison of yields and properties of LTLP hydrogenated phenolic oligomers and hydroprocessed bio-oils as reported in the literature

A.

|  | Unit | Hydrogenated CS SF1 PO | Hydrogenated CS SF2 PO | Hydrogenated RO SF1 PO | Hydrogenated RO SF2 PO |
| --- | --- | --- | --- | --- | --- |
| Catalyst |  | Pd/C | Pd/C | Pd/C | Pd/C |
| Temperature | ° C. | 21 | 21 | 21 | 21 |
| Pressure | bar | 1.0 | 1.0 | 1.0 | 1.0 |
| Oil Product Yield | wt % | 94.5 | 86.1 | 85.0 | 99.7 |
| Carbon Yield | mole/g bio-oil (db) | 0.077 | 0.071 | 0.065 | 0.065 |
| Hydrogen Consumption | L/L feed | 62.1 | 41.0 | — | 234 |
| Hydrogenated PO Carbon Content | molar % of carbon in PO | 98.2 | 98.5 | 91.8 | 77.7 |
| Viscosity | cP (60° C.) | 299 | 729 | — | 58 |
| Density | g/ml | 1.16 | 1.19 | 1.36 | 1.27 |
| Ash Content | wt % | 0.17 | 0.07 | 0.08 | 0.06 |
| Average Relative Molecular Weight | Da | 913 | 774 | 1148 | 925 |

TABLE 2-continued

Comparison of yields and properties of LTLP hydrogenated phenolic oligomers
and hydroprocessed bio-oils as reported in the literature

| C (db) | wt % | 64.2 | 67.7 | 57.7 | 62.2 |
|---|---|---|---|---|---|
| H (db) | wt % | 7.23 | 7.11 | 8.27 | 6.59 |
| N (db) | wt % | 1.74 | 1.25 | 0.242 | 0.132 |
| O (by difference) | wt % | 26.8 | 24.0 | 33.8 | 31.1 |
| H/C (db) | molar | 1.3 | 1.3 | 1.7 | 1.3 |
| O/C(db) | molar | 0.31 | 0.27 | 0.44 | 0.38 |

B.

| | Unit | Conti et al.[21] | Mortensen et. al[8] Wildschut et. al[14] | Ardiyanti[18] | Mortensen et. al[8] Wildschut et. al[14] |
|---|---|---|---|---|---|
| Catalyst | | Pd/C | Pd/C | Ru/C | Ru/C |
| Temperature | °C. | 340 | 350 | 225 | 350 |
| Pressure | bar | 140 | 200 | 200 | 200 |
| Oil Product Yield | wt % | 45 | 65 | 47.8 | 53 |
| Carbon Yield | mole/g bio-oil (db) | 0.059 | — | — | — |
| C (db) | wt % | 79.4 | — | 67.9 | — |
| H (db) | wt % | 10.2 | — | 6.85 | — |
| N (db) | wt % | 2.4 | — | 0.5 | — |
| O (by | wt % | 8.29 | — | 24.8 | — |
| H/C (db) | molar | 1.5 | 1.6 | 1.2 | 1.5 |
| O/C (db) | molar | 0.1 | 0.7 | 0.28 | 0.8 |

The LTLP hydrogenation of phenolic oligomers resulted in high product yield: 94.5 wt % for CS SF1 PO, 86.1 wt % for CS SF2 PO, 85 wt % for RO SF1 PO and 99.7 wt % for RO SF2 PO. These are significant yields of upgraded product compared to previous studies on hydroprocessing whole bio-oil, which only averaged 53 wt % (P. M. Mortensen, et al., *Applied Catalysis A: General*, 407: 1-19 (2011); J. Wildschut, et al., *Industrial & Engineering Chemistry Research*, 48: 10324-10334 (2009); A. Ardiyanti, Ph.D., University of Groningen (2013); L. Conti, et al., in *Bio-Oil Production and Utilization*, ed. A. V. B. a. E. N. Hogan, CPL Press, Newbury, UK, pp. 198-205 (1996), which are expressly incorporated by reference herein in their entirety).

The carbon yields for hydrogenated CS SF1 PO and CS SF2 PO were 0.077 mol carbon/g bio-oil feed dry basis (db) and 0.071 mol carbon/g bio-oil feed (db), respectively. The carbon yield for hydrogenated RO SF1 PO and RO SF2 PO showed slightly lower carbon yields, 0.065 mol carbon/g bio-oil feed (db). In comparison, Elliot et al., *Environmental Progress & Sustainable Energy*, 28: 441-449 (2009), which is herein expressly incorporated by reference in its entirety, obtained a carbon yield of 0.059 mol carbon/g bio-oil feed (db) when hydroprocessing whole bio-oil produced from cornstover.

Hydrogen consumption was 62.1 L/L bio-oil for CS SF1 PO and 41.0 L/L bio-oil for CS SF2. RO SF2 PO resulted in hydrogen consumption of 241 L/L bio-oil. These results are similar to Elliot et al., *Environmental Progress & Sustainable Energy*, 28: 441-449 (2009), who reported hydrogen consumption to be 76-128 L/L bio-oil and 252 L/L bio oil for whole bio-oils from cornstover and poplar wood, respectively.

Elemental analysis indicated CS PO SF1 and SF2 contain 59% (wb) of total carbon while RO PO SF1 and SF2 contained 57% of total carbon (wb) in the produced bio-oils. The carbon content of the hydrogenated CS SF1 PO was 98.2 molar % of overall molar % of carbon content in the CS SF1 PO. High carbon content yields were obtained for the hydrogenated CS SF2 PO, RO SF1 PO and RO SF2 PO samples as well; 98.5 molar %, 91.8 molar %, and 77.7 molar %, respectively. These yields show a significant increase compared to those reported in literature, 33-35 molar % carbon content of the bio-oil feed after hydrogenation of pyrolytic lignin/water insoluble bio-oil at 250-300° C. at 140 bar pressure (H. Ben, et al., *Fuel*, 103: 1148-1153 (2013), which is herein expressly incorporated by reference in its entirety). Therefore, the carbon content after LTLP hydrogenation remained in the sample and was not lost to noncondensable gases, tars, and coking.

The viscosities of phenolic oligomer samples (measured at 60° C.) dropped dramatically upon hydrogenation both for samples prepared from (6 month aged) corn stover and fresh red oak. CS SF1 PO and CS SF2 PO were 1,598 cP and 1,375 cP, respectively, before hydrogenation, dropping to 299 cP and 729 cP, respectively, after hydrogenation. RO SF2 PO showed a more dramatic drop in viscosity, decreasing from 4859 cP before hydrogenation to a very fluid 57.7 cP after hydrogenation (RO SF 1 PO was not tested because of insufficient sample size). The fact that hydrogenation of fresh stage fraction bio-oil produced a greater drop in viscosity than the aged stage fraction bio-oil suggests that the fresh sample contained more reactive functional groups and was able to react with more hydrogen than the aged sample, an idea explored in subsequent chemical analysis.

This viscosity thinning after LTLP hydrogenation is in sharp contrast to the viscosity thickening observed by researchers who hydroprocessed bio-oil at higher temperatures and pressures. Normally, hydrogenation of unsaturated carbon bonds is expected to increase the viscosity of oil. However, as subsequent chemical analyses reveals, the stage fractions before hydrogenation contain both unsaturated carbon bonds and carbonyl groups. Mild hydrogenation of the latter yields alcohols that can provide self-solvation power to the phenolic oligomers.

The O/C as well as the H/C ratios fall within the range measured for bio-oil catalytically upgraded at much higher temperatures and pressures (225-350° C. and 200 bar)

utilizing Ru/C catalyst (P. M. Mortensen, et al. *Applied Catalysis A: General*, 407: 1-19 (2011); J. Wildschut, et al., *Applied Catalysis B: Environmental*, 99: 298-306 (2010); A. Ardiyanti, Ph.D., University of Groningen (2013), which are herein expressly incorporated by reference in their entirety). The H/C ratio is high enough and the O/C ratio low enough for the hydrogenated phenolic oligomers to be considered for direct use as fuel oil, although this possibility would require further evaluation to determine the combustion properties of the product.

In particular, Table 3 provides the percentage of hydrogen based on $^1$H NMR analysis of heavy ends phenolic oligomers (PO) bio-oil from fast pyrolysis of corn stover (CS) and red oak (RO) grouped according to chemical shift range (H. Ben, et al., *Fuel*, 103: 1148-1153 (2013); C. A. Mullen, et al., *Energy & Fuels*, 23: 2707-2718 (2009); L. Ingram, et al., *Energy & Fuels*, 22: 614-625 (2007); A. Oasmaa, et al., *Energy & Fuels*, 24: 5264-5272 (2010); M. Kosa, et al., *Green Chemistry*, 13: 3196-3202 (2011), which are herein expressly incorporated by reference in their entirety).

TABLE 3

Percentage of hydrogen based on $^1$H NMR analysis of heavy ends phenolic oligomers (PO) bio-oil from fast pyrolysis of corn stover (CS) and red oak (RO) untreated or subject to hydrogenation (Hyd).

| Chemical Shifts (ppm) | CS SF1 PO (%) | CS SF1 PO Hyd (%) | CS SF2 PO (%) | CS SF2 PO Hyd (%) | RO SF1 PO (%) | RO SF1 PO Hyd (%) | RO SF2 PO (%) | RO SF2 PO Hyd (%) |
|---|---|---|---|---|---|---|---|---|
| 1.6-0.0 | 15.5 | 32.2 | 29.0 | 36.4 | 2.8 | 12.6 | 5.4 | 14.3 |
| 2.2-1.6 | 16.3 | 24.1 | 16.9 | 21.0 | 8.4 | 12.4 | 6.1 | 8.1 |
| 4.2-3.0 | 39.6 | 21.6 | 31.7 | 20.1 | 68.6 | 43.6 | 70.9 | 49.7 |
| 6.4-4.2 | 3.0 | 0.8 | 3.3 | 1.6 | 6.8 | 8.4 | 3.8 | 5.4 |
| 6.8-6.4 | 9.5 | 7.5 | 6.6 | 6.8 | 4.7 | 9.3 | 6.6 | 8.9 |
| 8.0-6.8 | 2.5 | 1.5 | 1.6 | 1.5 | 0.6 | 0.9 | 1.7 | 0.8 |
| 10-8.0 | 0.8 | 0.8 | 0.1 | 0.3 | 2.1 | 1.8 | 0.9 | 2.2 |

LTLP hydrogenation of phenolic oligomers produced little or no detectable coke. In contrast, severe hydroprocessing of bio-oil yielded up to 40 wt % coke (P. M. Mortensen, et al., *Applied Catalysis A: General*, 407: 1-19 (2011); R. H. Venderbosch, et al., *Journal of Chemical Technology & Biotechnology*, 85: 674-686 (2010), which are herein expressly incorporated by reference in their entirety) and mild hydrotreating at 150-380° C., 138-172 bar produced between 1.0-8.2 wt % coke (R. J. French, et al., *Environmental Progress & Sustainable Energy*, 29: 142-150 (2010), which is herein expressly incorporated by reference in its entirety). Hydroprocessing of so-called pyrolytic lignin (obtained by separating phenolic oligomers from whole bio-oil) also was reported to produce severe coking of upgrading catalysts (H. Ben, et al., *Fuel*, 103: 1148-1153 (2013), which is herein expressly incorporated by reference in its entirety).

Figure 3A:
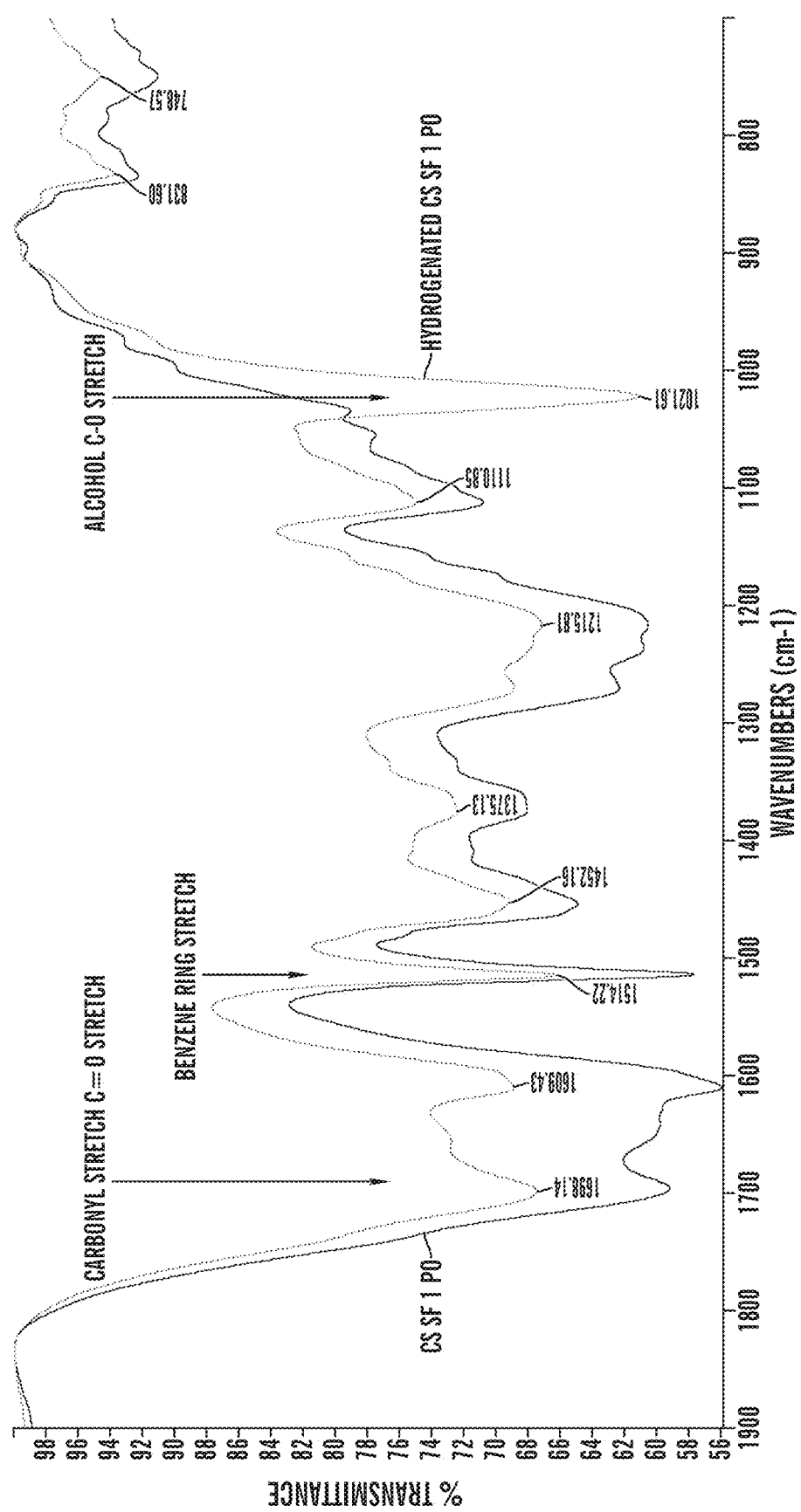
FIGS. 3A-B are graphs comparing the Fourier transform infrared (FTIR) for untreated (non-hydrogenated) and hydrogenated samples showing conversion of carbonyl groups to alcohol groups and the loss of the benzene ring stretch.
Figure 3B:
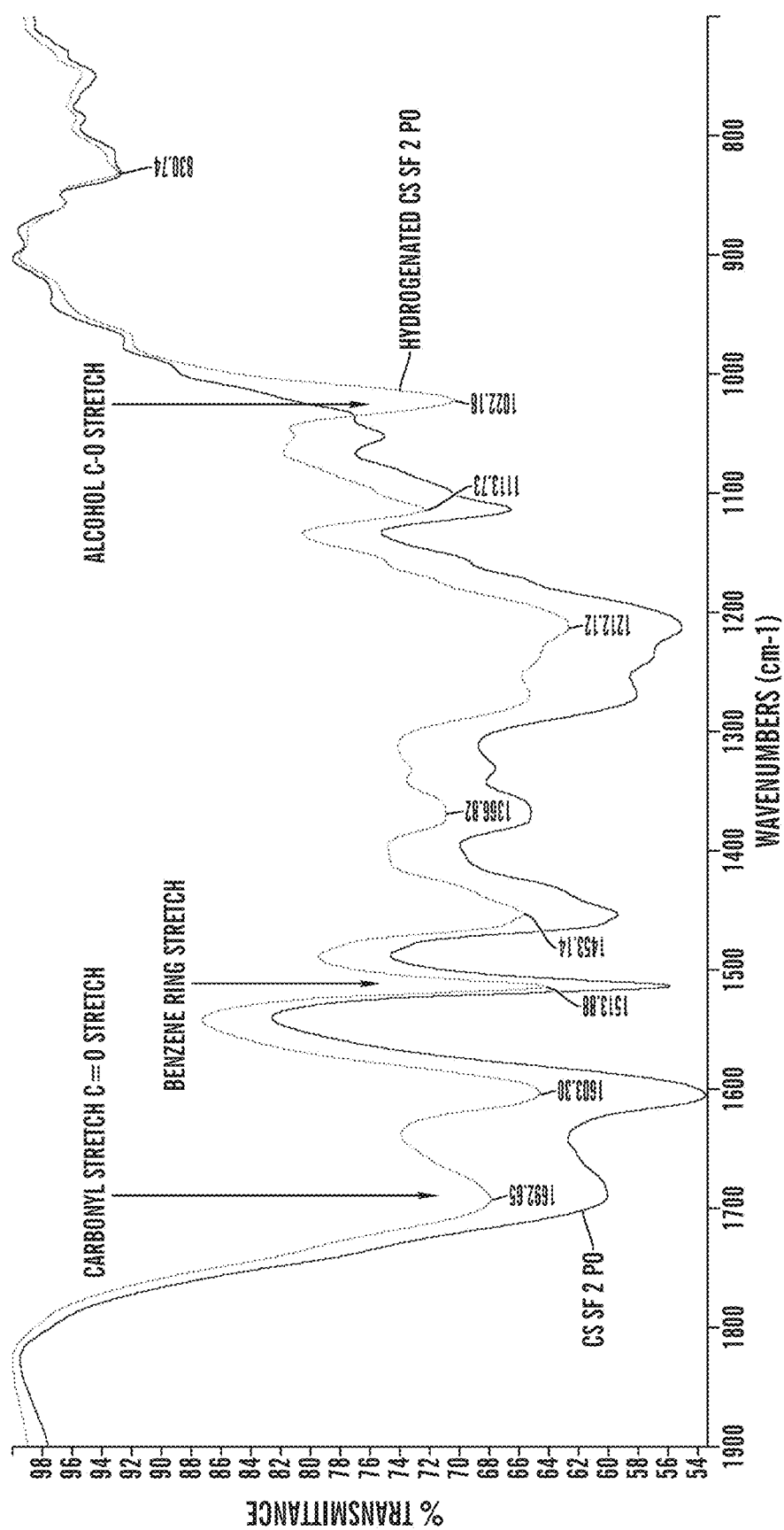

Fourier transform infra-red spectroscopy (FTIR) was used to evaluate changes in functional groups upon LTLP hydrogenation of CS SF1 PO and CS SF2 PO. As shown in FIG. 3, alcohols (1065-1015 cm$^{-1}$ C—O stretch in cyclic alcohols and 1060-1025 cm$^{-1}$ C—O stretch in primary alcohols) increase after hydrogenation while carbonyl groups (1710-1685 cm$^{-1}$ C=O stretch in aromatics, 1710-1690 cm$^{-1}$ C=O stretch in carboxylic acids, and 1720-1700 cm$^{-1}$ C=O stretch in ketones) decrease, which shows that LTLP hydrogenation converted carbonyl functionality in the phenolic oligomers to alcohol groups.

The aromaticity also decreased after LTLP hydrogenation of the both CS SF1 and SF2 PO, as indicated by a decrease in the benzene ring stretch (1515-1485 cm$^{-1}$).

Figure 4A:
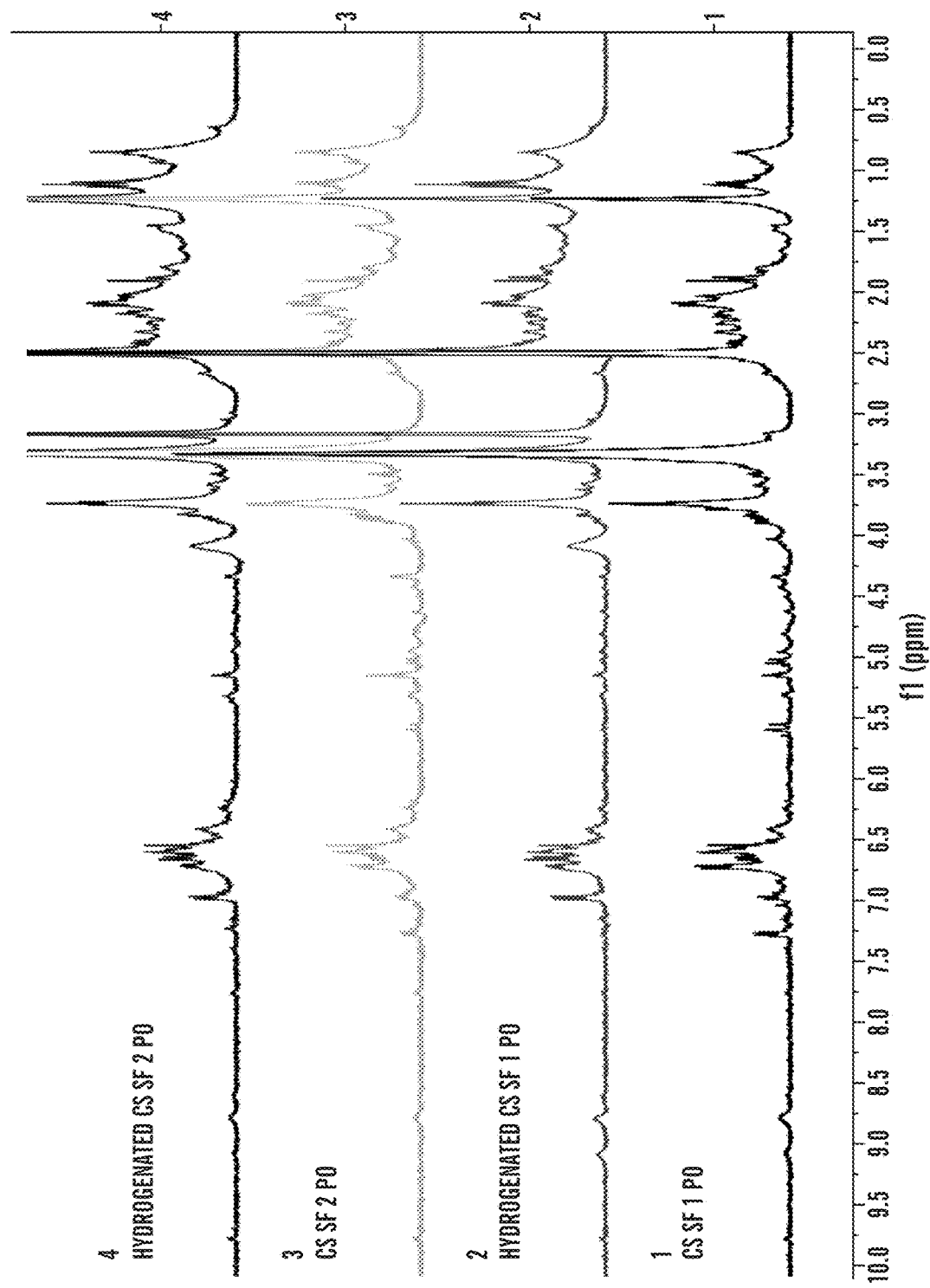
FIGS. 4A-B are graphs comparing the $^1$H NMR spectra of bio-oil stage fraction 1 phenolic oligomers (CS SF1 PO) and stage fraction 2 phenolic oligomers (SF2 PO) obtained from fast pyrolysis of corn stover (CS) or red oak (RO), before and after hydrogenation, indicating the loss of vinyl groups and the increase in aliphatic.
Figure 4B:
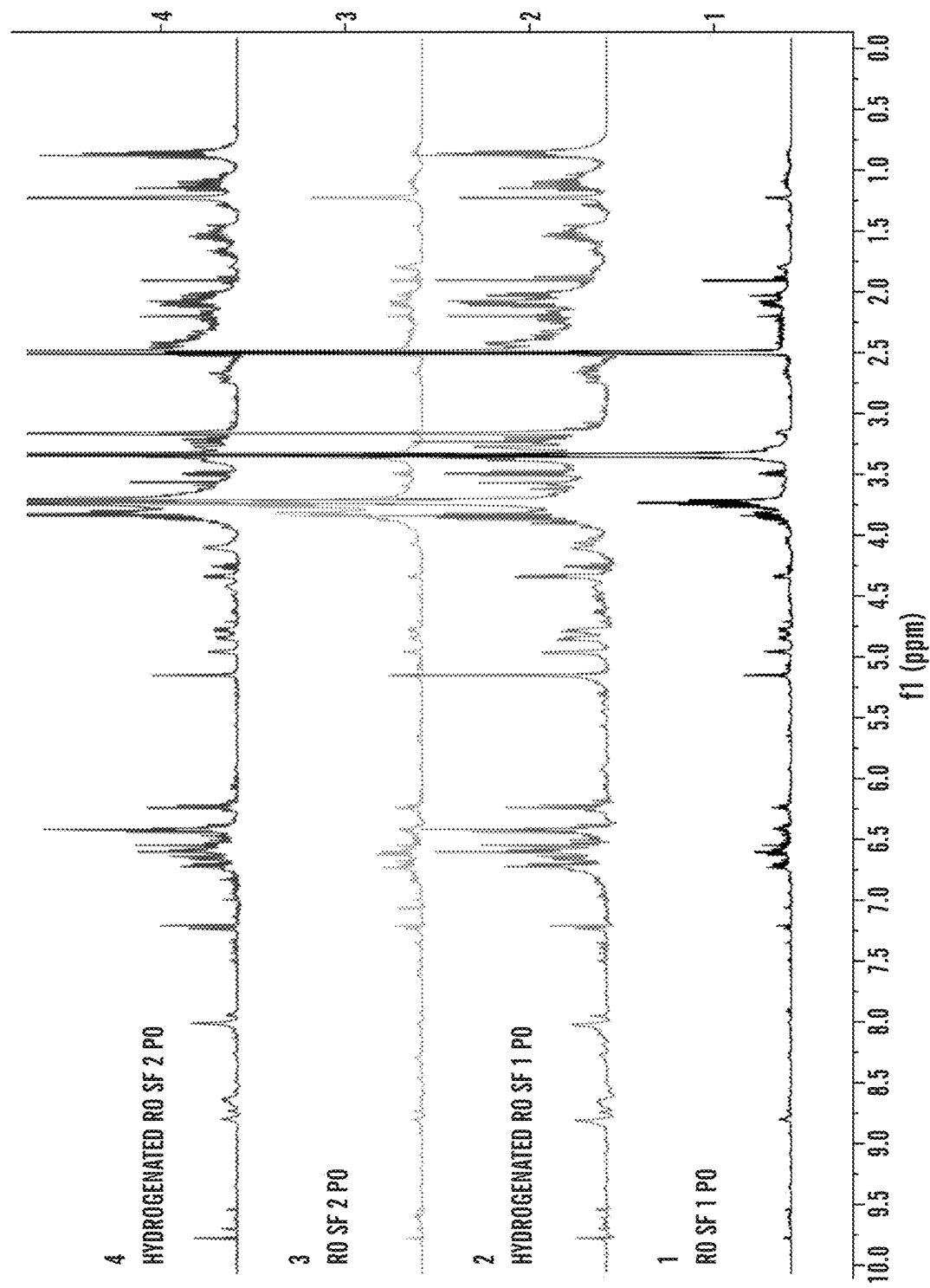

FIG. 4 provides the $^1$H NMR spectra of the phenolic oligomers before and after hydrogenation of the CS and RO bio-oil. These semi-quantitative results (shown in Table 3 below) were obtained by methods suggested by Mullen et al., *Energy & Fuels*, 23: 2707-2718 (2009) and Ingram et al., *Energy & Fuels*, 22: 614-625 (2007), which are herein expressly incorporated by reference in their entirety, that utilized normalized integration based on the $^1$H NMR.

The hydrogenated samples CS SF1 PO Hyd, RO SF1 PO Hyd, and RO SF2 PO Hyd showed substantial increases in the aliphatic proton resonance region (δ 2.2-0.0 ppm); 84.3%, 110% and 86.9%, respectively. Hydrogenated CS SF2 PO showed 39.8% increase in aliphatic protons. The increases in this region of the NMR spectrum confirmed that hydrogenation was successful. The hydrogenated CS SF1 and SF2 POs and the RO SF1 and SF2 show decreased resonance in the δ 4.2-3.0 ppm (i.e., resonances from methoxyls, ethers, aliphatic alcohols or methylene groups joining two aromatics) of 29.6-45.5%, which may be due to bond cleavage during hydrogenation. Oasmaa et al., *Energy & Fuels*, 24: 5264-5272 (2010), which is herein expressly incorporated by reference in its entirety, reported similar findings of decreasing methoxyl groups during hydrotreatment. The proton resonances decreased in the CS phenolic oligomers at δ 6.4-4.2 ppm (hydrogen on carbon atoms next to methoxyl groups, nonconjugated C=C and phenolic alcohols) but increased in the RO phenolic oligomers. Hydrogenated CS SF1 and SF2 POs decreased by 73.3% and 51.5%, respectively. The hydrogenated RO SF1 PO increased by 19.0% and RO SF2 PO increased by 29.6%, which may be due to alcohol conversion to phenolic alcohols (reflected in the dramatic decrease in viscosity of the hydrogenated RO SF2 PO).

Three samples showed loss of aromaticity (δ 8.0-6.8 ppm). The hydrogenated CS SF1 PO showed a loss of 40.0% proton resonance, CS SF2 PO showed a slight loss of 6.25%, while RO SF2 PO indicated a 52.9% loss. The FTIR analysis is in agreement, showing a loss of benzene ring stretching after hydrogenation that validates bio-oil reactivity.

Aldehyde, carboxylic acid, and lower field aromatic proton resonances (δ 10.0-8.0 ppm) showed a decrease in the RO SF1 hydrogenated sample while the CS and RO SF2 hydrogenated samples increased.

Figure 5:
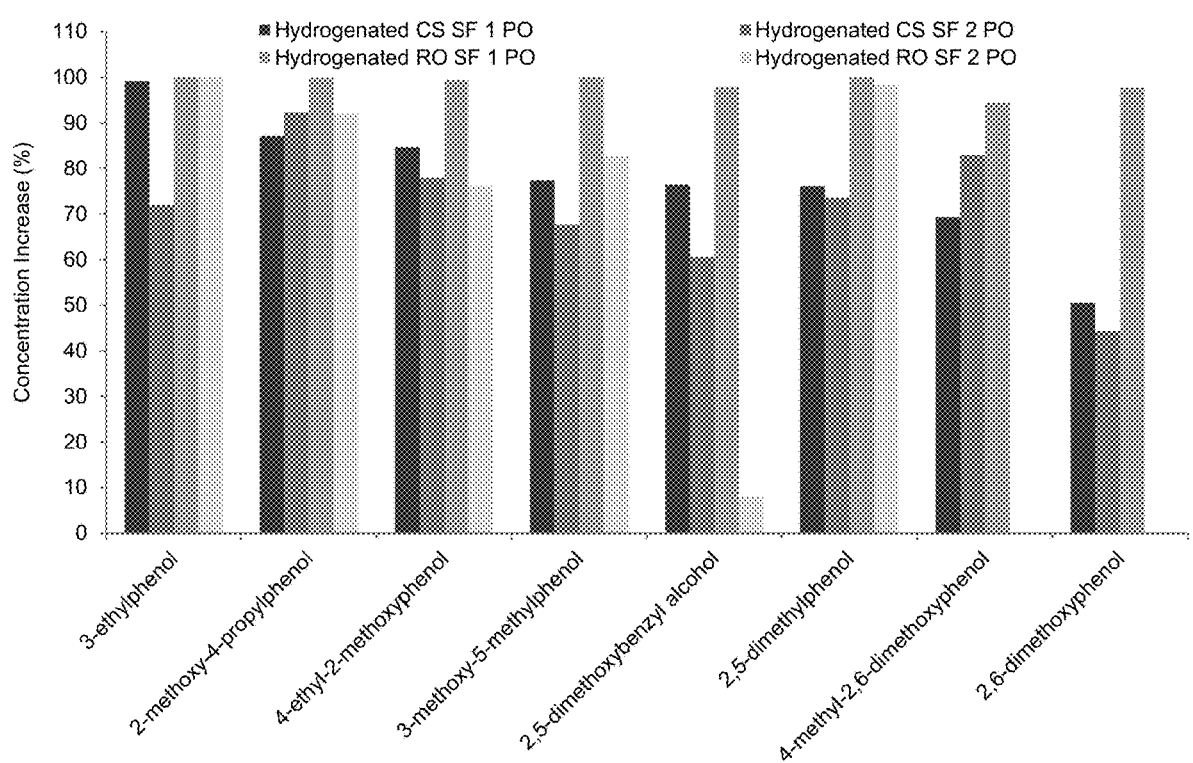
FIG. 5 is a graph showing the chemical species identified by calibrated GC/FID showing percent increase after hydrogenation of cornstover (CS) and red oak (RO) stage fraction (SF)1 and SF2 phenolic oligomers (PO) indicating production of syringol and derivatives of syringol and guaiacol.

GC/FID analyses indicated increases in specific calibrated compounds in the hydrogenated products (FIG. 5). The increased compounds included guaiacol, syringol and variations of these, demonstrating that aromatic monomers increased during LTLP. Hydroprocessing of bio-oil pyrolytic lignin at 300° C. using 140 bar pressure over Ru/C catalyst (sorted by area percentages) produced major components that included 2-methoxyl-4-methylphenol, 2-methoxylphenol, 2,4-dimethylphenol, 4-ethyl-2-methoxylphenol, 2-methylphenol, 4-methylphenol, and 2-methoxyl-4-propylphenol (H. Ben, et al., *Fuel*, 103: 1148-1153 (2013), which is herein expressly incorporated by reference in its entirety). These were similar types of compounds that increased in the LTLP hydrogenated CS and RO. This increase in monomeric phenols may have influenced viscosity of the hydrogenated products, making them more fluid in addition to carbonyl conversion to alcohols. The production of monomeric phenols during LTLP hydrogenation suggests these products may be stable enough for further upgrading at more severe temperatures and pressures.

Figure 6A:
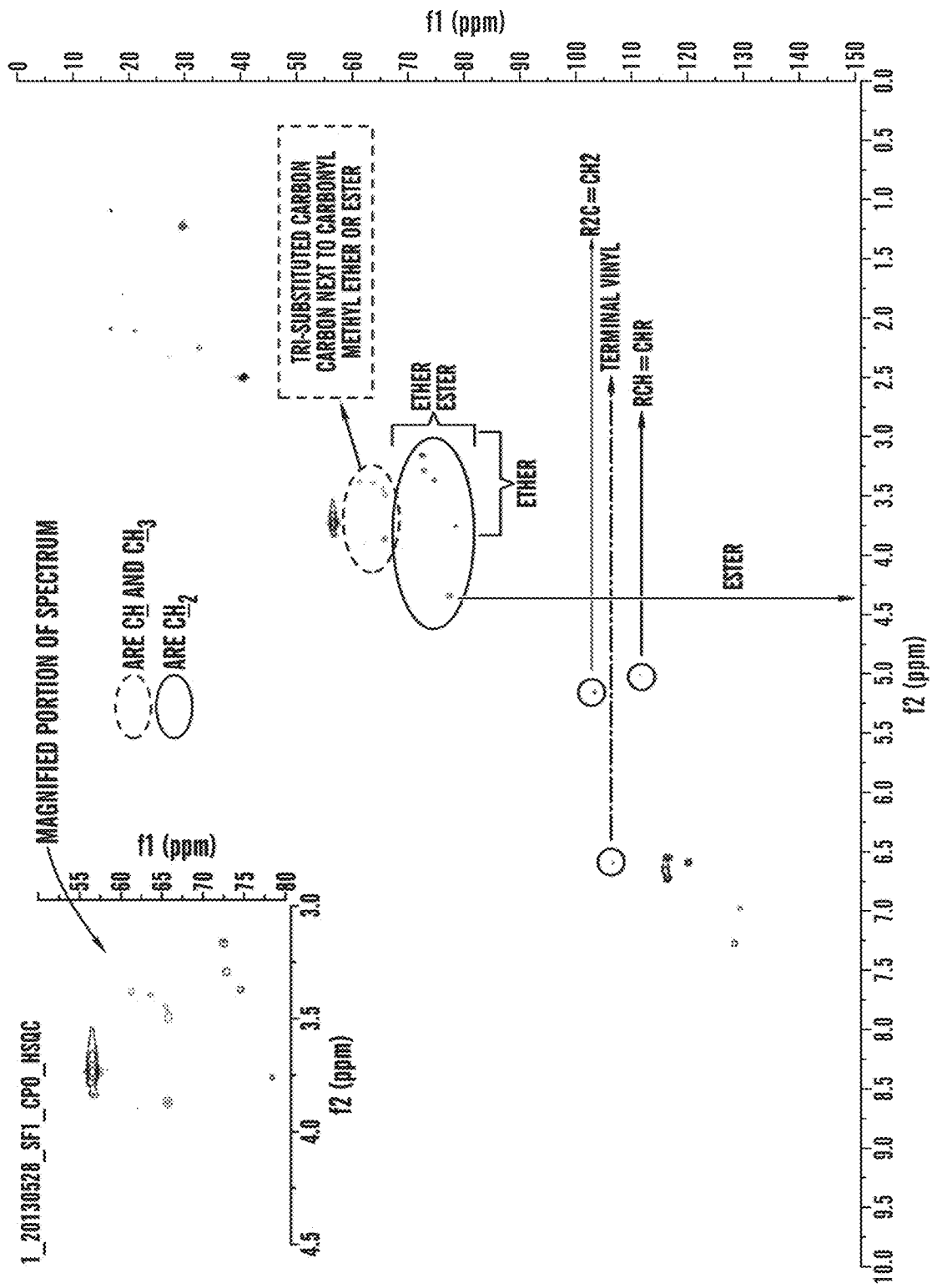
FIGS. 6A-B are graphs comparing the Heteronuclear Single Quantum Coherence (HSQC) spectra of cornstover (CS) stage fraction (SF) 1 bio-oil before and after hydrogenation.
Figure 6B:
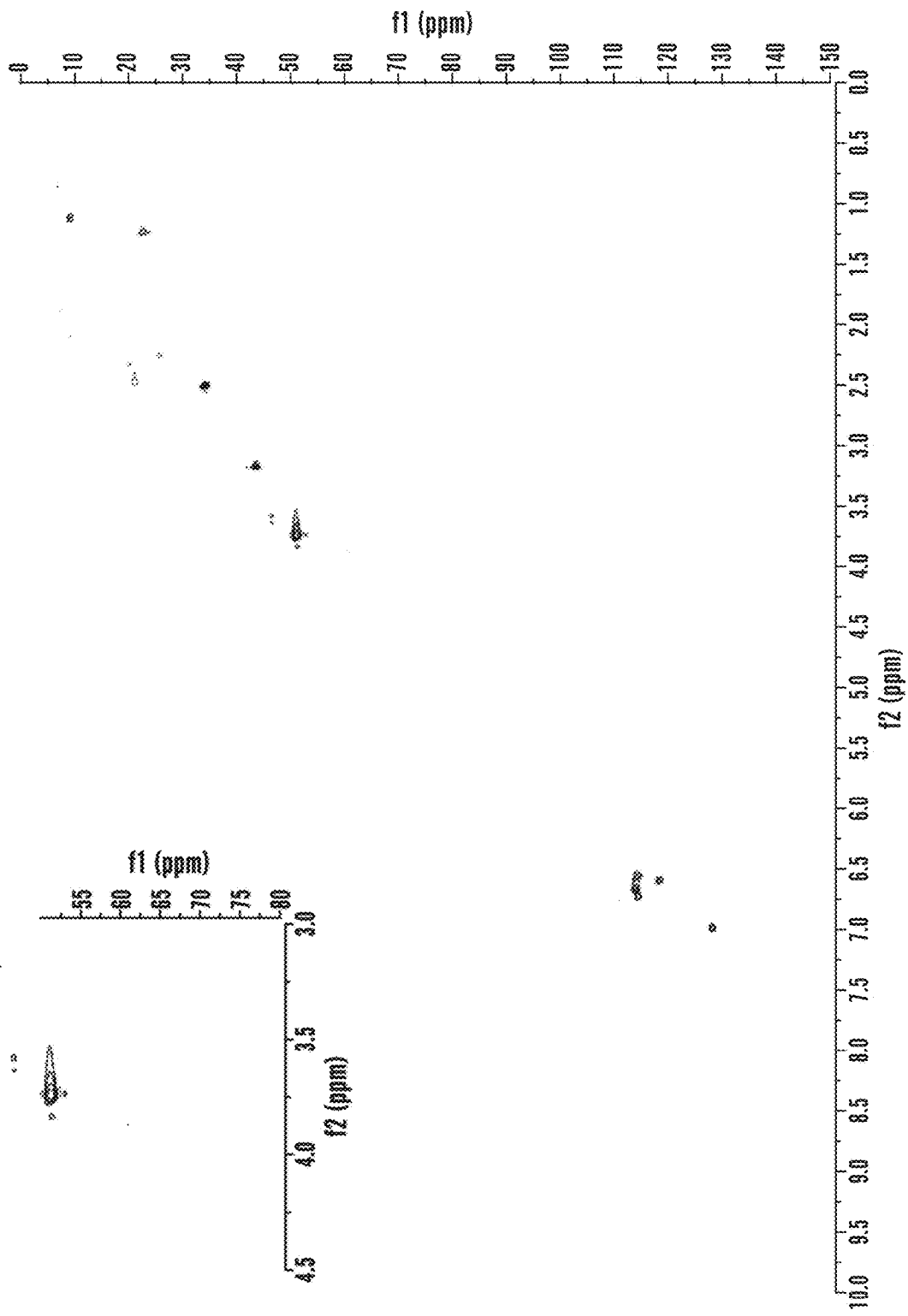

Additionally, Heteronuclear Single Quantum Coherence (HSQC) spectroscopy, in which the data is presented as the $^1$H NMR spectrum (x-axis) correlated with the $^{13}$C NMR spectrum (y-axis), as used to demonstrate that ether and ester bond cleavage occurred during LTLP hydrogenation of bio-oil at 21° C. and 1 bar pressure (FIG. 6A-B). Only those carbon atoms that have attached protons are shown.

As indicated in FIGS. 6A and 6B, ether and ester bonds were lost in the hydrogenated bio-oil samples. Ether and ester carbon resonances were present at δ 80-60 ppm on the $^{13}$C NMR spectrum, whereas the corresponding proton resonances for ethers and esters presented at approximately δ 3.75-3.25 ppm and δ 4.30-3.60 ppm, respectively. Semi-quantitative changes in the hydrogenated CS SF1 bio-oil were acquired by integration and normalization to the solvent peak. The integration of δ 4.5-3.3 ppm in both the starting material and product indicated 41.1% loss of ether and ester functionality.

Example 2

Zn and HCl Upgrading of Bio-Oil

The Clemmensen reduction[1] was used to upgrade hydrogenated bio-oil SF1 PO, e.g., to remove carbonyl groups. The Clemmensen reduction method is a general methodology in which ketones are converted to the corresponding hydrocarbons with amalgamated zinc and HCl. Modified to operate at much milder conditions (e.g., 0° C. for 1-2 hours), the Clemmensen reduction method reduces a variety of ketones found in whole or fractionated bio-oil (OSHA, ed. U. S. D. o. Labor, Washington, D.C. (2013), which is herein expressly incorporated by reference in its entirety). In this Example, the reaction was slightly modified (as explained below) for use with hydrogenated SF1 PO.

50 ml ether was added to a flask. The temperature was held at −10 to −15° C. HCl was added dropwise for 45 minutes (10 ml). Hydrogenated SF1 POs (2 g) was added to the ether. Since the hydrogenated SF1 PO was only slightly soluble, 25 ml of methanol was used to rinse the hydrogenated SF1 PO into the ether. The solution of ether and methanol was cooled to −20° C. and the bio-oil sample was dissolved. Activated Zn (2.5 g) was added to the solution (Zn was activated by using procedure from S. Yamamura, et al., in *Organic Syntheses*, John Wiley & Sons, Inc. (2003) over a 2-3 min period). The solution was kept at (0 to −4° C.) for 2 hours stirring with stir bar at 350 rpm. It was then filtered with Celite® 503, and the filtrate was rotary evaporated to dryness to remove solvent. 75 ml water was added to the filtrate and centrifuged at 1560 g. The water was decanted, and another 40 ml water was added prior to centrifugation at 1560 g. Again, the water was decanted and another 25 ml water was added prior to centrifugation at 1560 g. The mixture was filtered, and a brown powder was obtained.

Optionally, the aqueous layer can be extracted to recover water soluble, low molecular weight alcohols. For example, 5 or 6 carbon alcohols are suitable for aqueous phase extraction.

Figure 7:
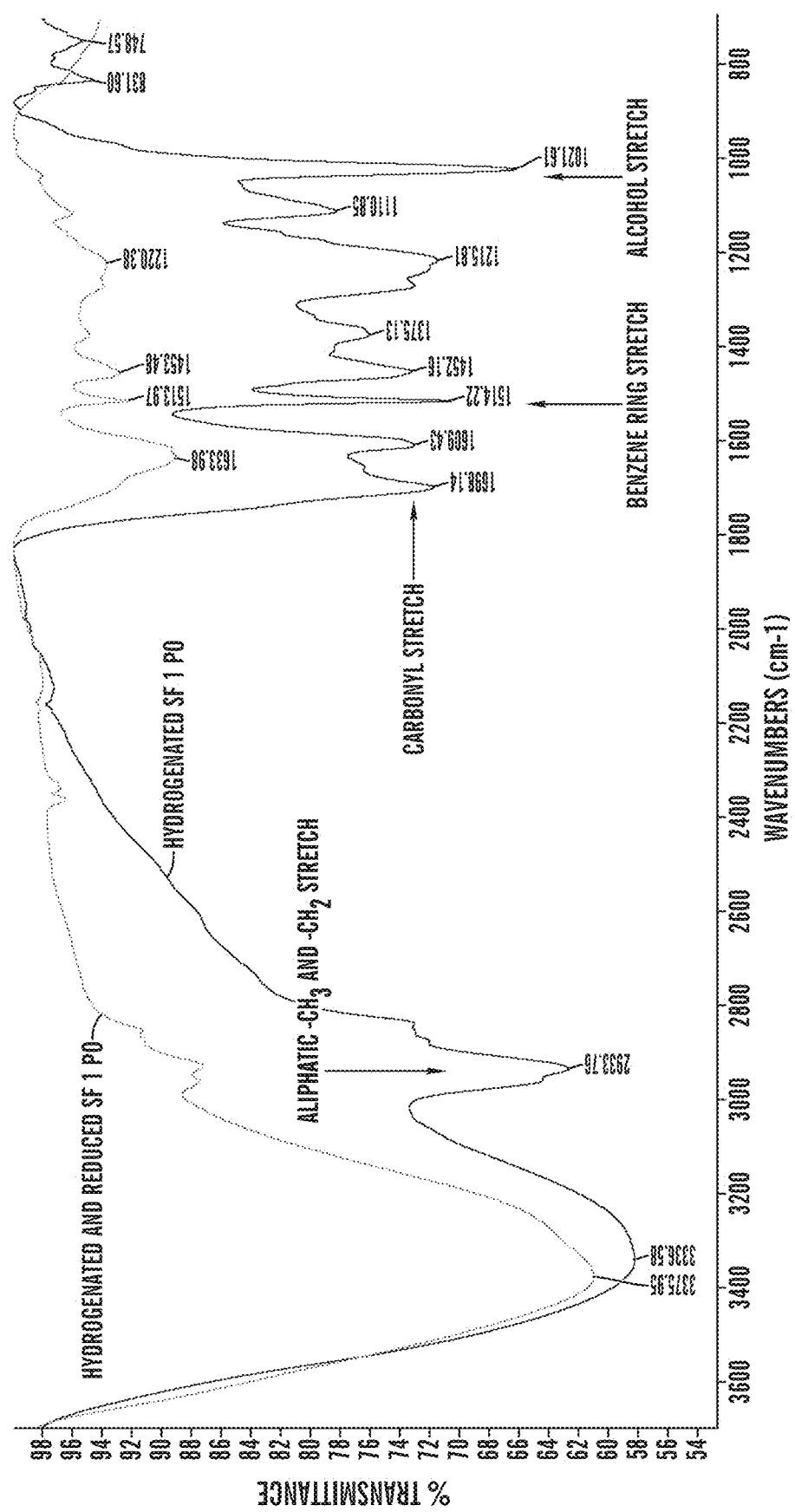
FIG. 7 is a graph comparing the FTIR spectra of SF1 PO after hydrogenation with SF1 PO after hydrogenation and reduction, illustrating the further loss of carbonyls, benzene and aliphatic —CH$_3$ and —CH$_2$—.

FTIR results indicate the filtrate powder (FIG. 7) lost aromaticity (i.e., benzene ring in aromatic compounds), as shown at 1514 cm$^{-1}$ (ring stretch). The filtrate was 82.3 wt % of the starting hydrogenated SF1 PO. Since the alcohol stretch at 1021 cm$^{-1}$ is missing in the upgraded SF1 PO, it is thought that the remaining 17.7 wt % includes alcohols. In this Example, extraction was not used on the aqueous layer to confirm whether alcohols were present.

Additionally, $^1$H NMR spectra (FIG. 8) also indicates the loss of aromaticity and aliphatic groups in the filtrate.

Overall, these results demonstrate that mild conditions can be used to "upgrade" bio-oil. In particular, the presently described modified Clemmensen reduction works well to remove reactive C=O groups from bio-oil at mild temperatures and pressures.

Example 3

Fermentation of Bio-Oil

Fermentation by Baker's yeast (*Saccharomyces cerevisiae*) is a mild and inexpensive method to reduce aldehydes and/or ketones (D. Mohan, et al., *Energy & Fuels*, 20: 848-889 (2006); C. A. Mullen, et al., *Energy & Fuels*, 23: 2707-2718 (2009), which are herein expressly incorporated by reference in their entirety). Specifically, microbial reduction of carbonyl compounds can be used to upgrade the phenolic oligomers found in bio-oil. Baker's yeast contains oxidoreductase enzymes and co-factors that reduce the substrate (D. Mohan, et al., *Energy & Fuels*, 20: 848-889 (2006), which is herein expressly incorporated by reference in its entirety). This enzymatic reduction is performed at ambient temperatures and pressure.

In this Example, the metholodolgy described by R. E. Bozak, et al., *Journal of Chemical Education*, 68: 427 (1991) was used for both 16 hour and 72 hour Baker's yeast experiments. To begin, 30 g of sucrose was added to 200 ml water and stirred for 10 minutes. Then 12 ml of methanol was added to 1 g hydrogenated SF1 PO and stirred until dissolved. The methanol/bio-oil solution was then added to the sucrose and water solution, and the fermentation mixture was left to ferment for 16 hours. The fermentation mixture was filtered with Celite® Celite 503 to remove yeast and any particulates. The Celite® 503 was washed 5 times with 50 ml methanol, and the filtrate was rotary evaporated to dryness. 100 ml of water was added to the sample and a precipitate formed. The precipitate was removed using a Buchner funnel. The sample was washed, and the precipitate was removed with water (3×100 ml water). The aqueous sample was extracted with 3×50 ml hexane. The hexane solubles were removed using a separatory funnel, and ethyl acetate was added to the hexane insoluble (aqueous phase) and extracted (3×100 ml). The hexane and ethyl acetate solubles were rotary evaporated. The remaining aqueous phase contained water-soluble compounds (e.g., alcohols and other low molecular weight species).

Figure 11A:
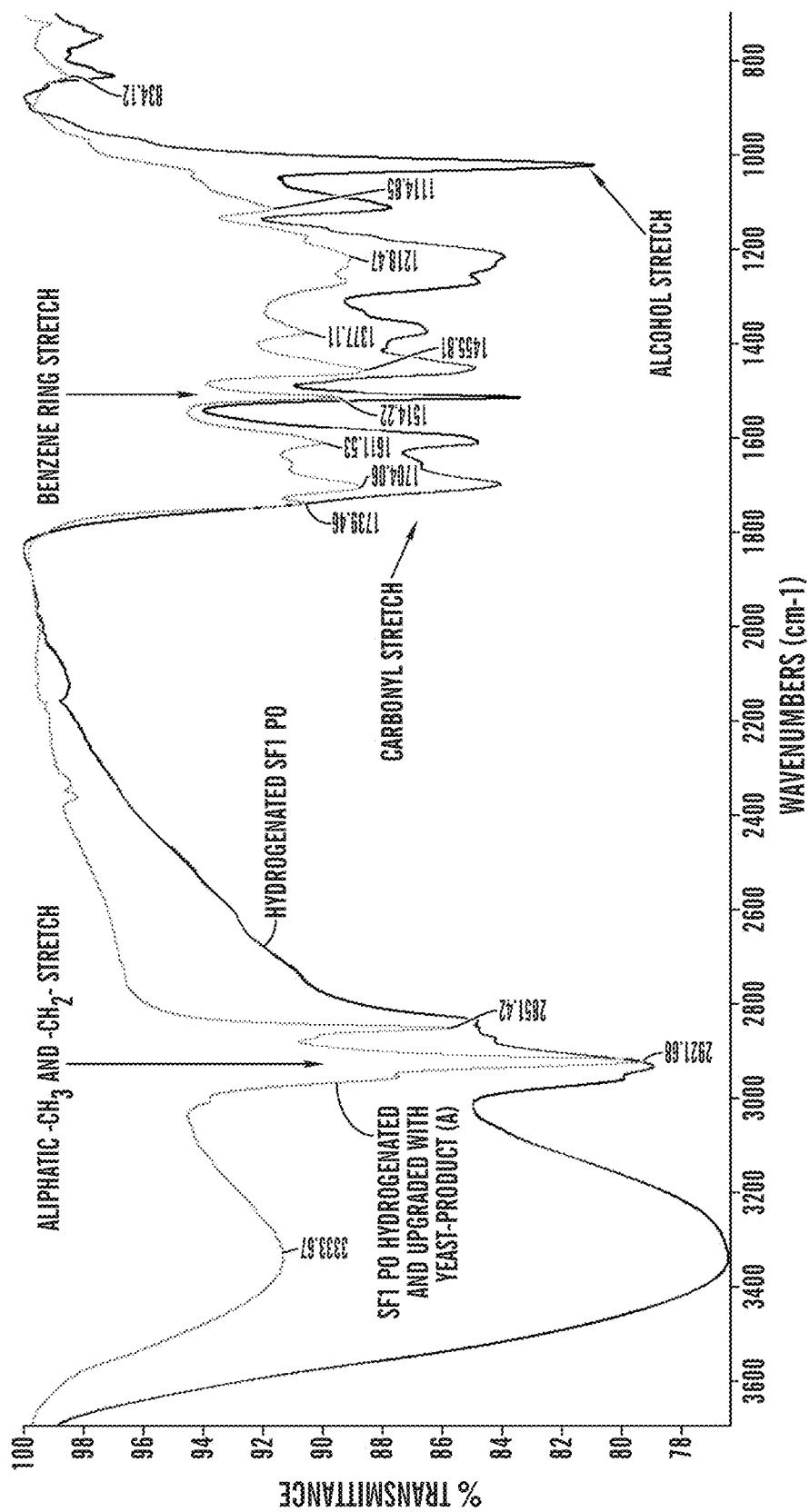
FIGS. 11A-C are graphs comparing the FTIR spectra of hydrogenated SF1 PO with hydrogenated SF1 PO subject to fermentation with Baker's yeast (72 hours). Product (a) shows a gain of aliphatic —$CH_3$ and —$CH_2$—, a slight loss of carbonyls and benzene, with the loss of alcohols (FIG. 11A), while the hexane soluble fermentation product (b) indicates gains in aliphatic —$CH_3$ and —$CH_2$— with losses in carbonyls and alcohols and a decrease in ethers (FIG. 11B). The ethyl acetate soluble fermentation product (c) shows losses of aliphatic, carbonyls, and benzene (FIG. 11C).
Figure 11B:
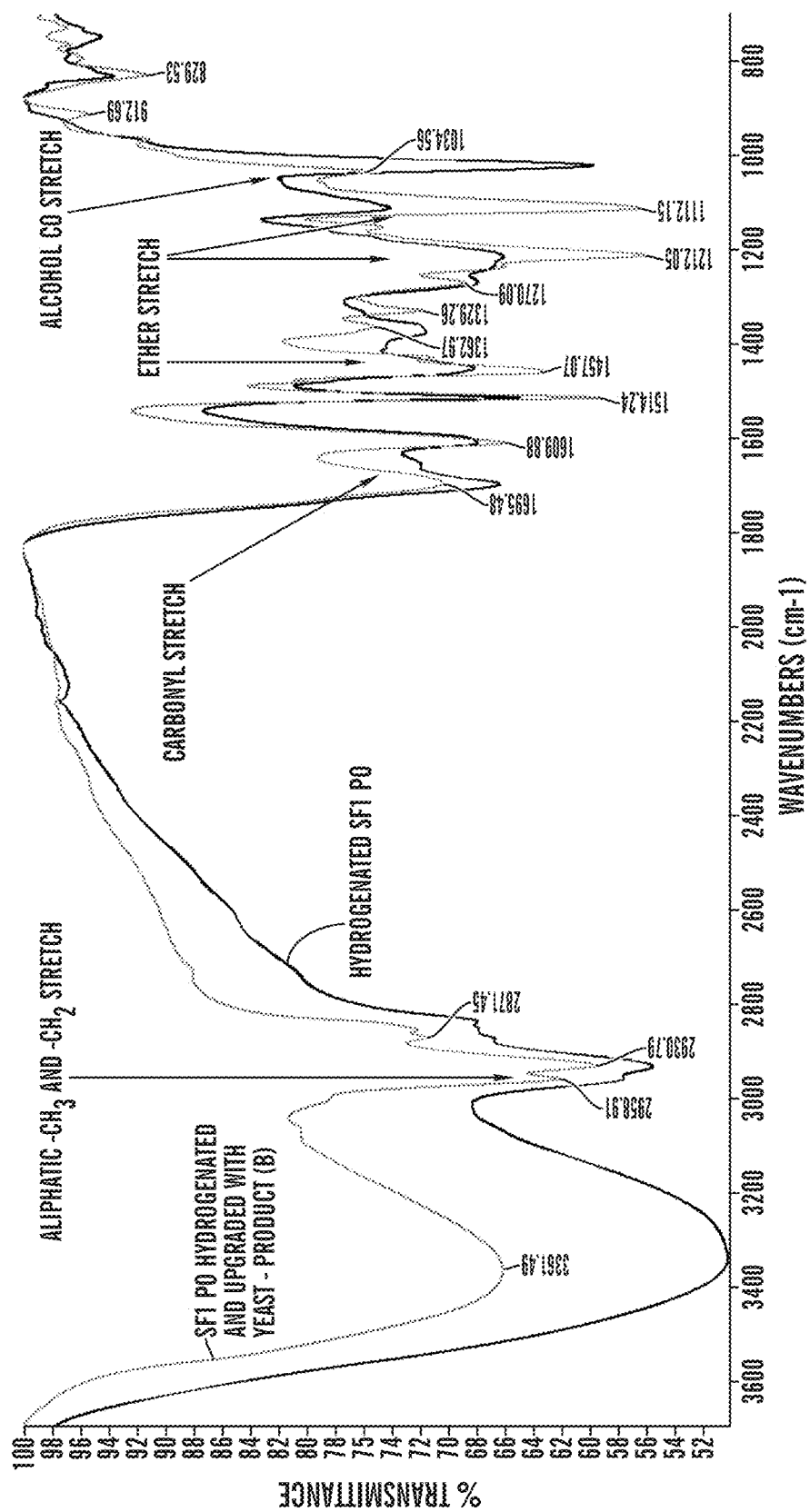
Figure 11C:
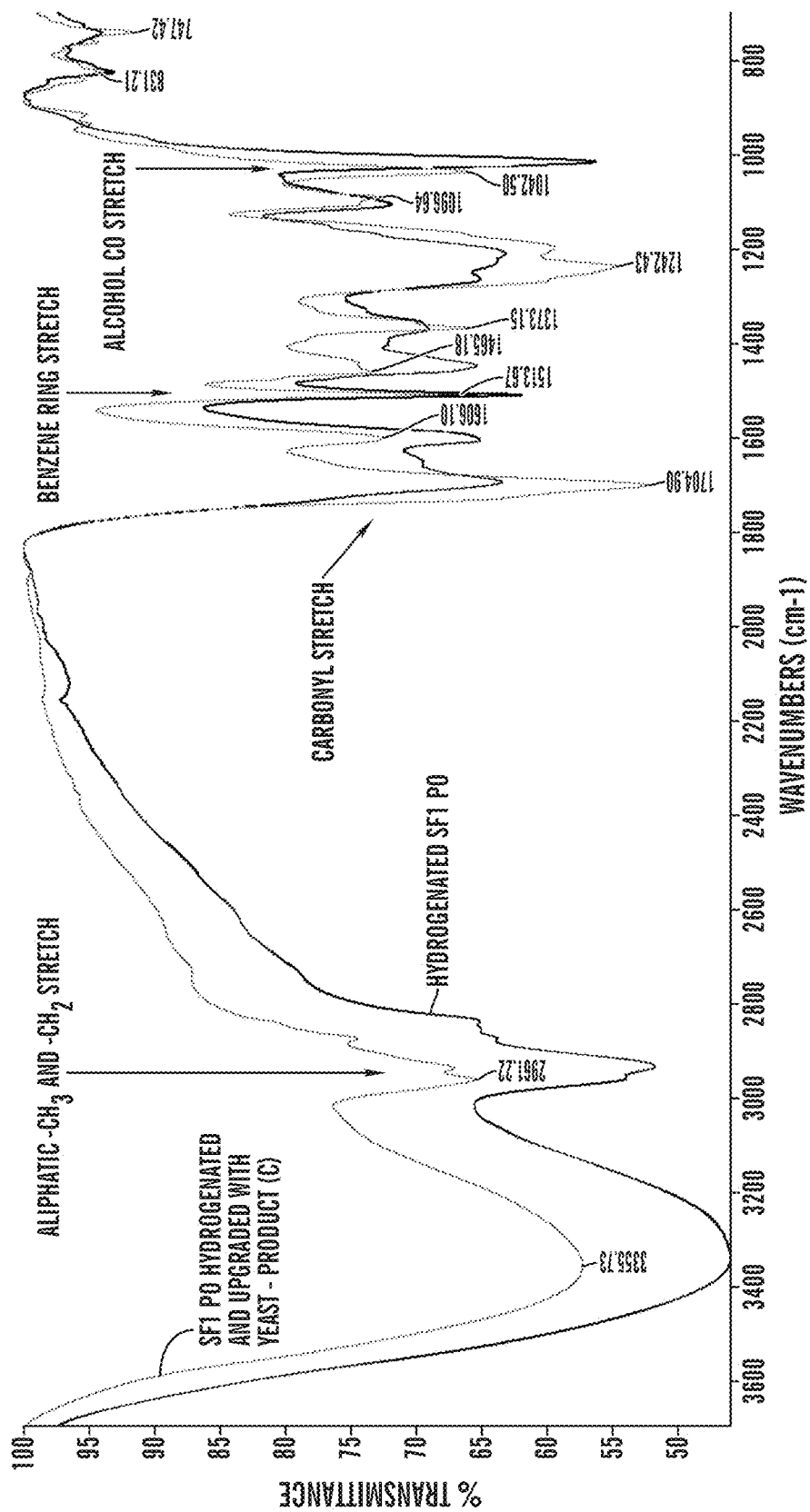

Four products were obtained utilizing Baker's yeast fermentation for 16 hours or 72 hours at room temperature, namely, product (a), i.e., a precipitate; product (b), i.e., the hexane soluble fraction; and product (c), i.e., the ethyl acetate soluble fraction. The color of the precipitate, i.e., product (a), from fermentation for 16 hours differs from that of fermentation for 72 hours. In particular, product (a) from the 16 hour fermentation is much darker in comparison to product (a) from the 72 hour fermentation. FIG. 11 indicates the formation of ethers, which were hexane soluble. Furthermore, during fermentation of two days or longer there is ether formation. Thus, the difference in color may be attributed to the formation of ether in the 72 hour fermentation experiment but not in the 16 hour fermentation experiment.

Three of the four products were further analyzed.

Figure 9A:
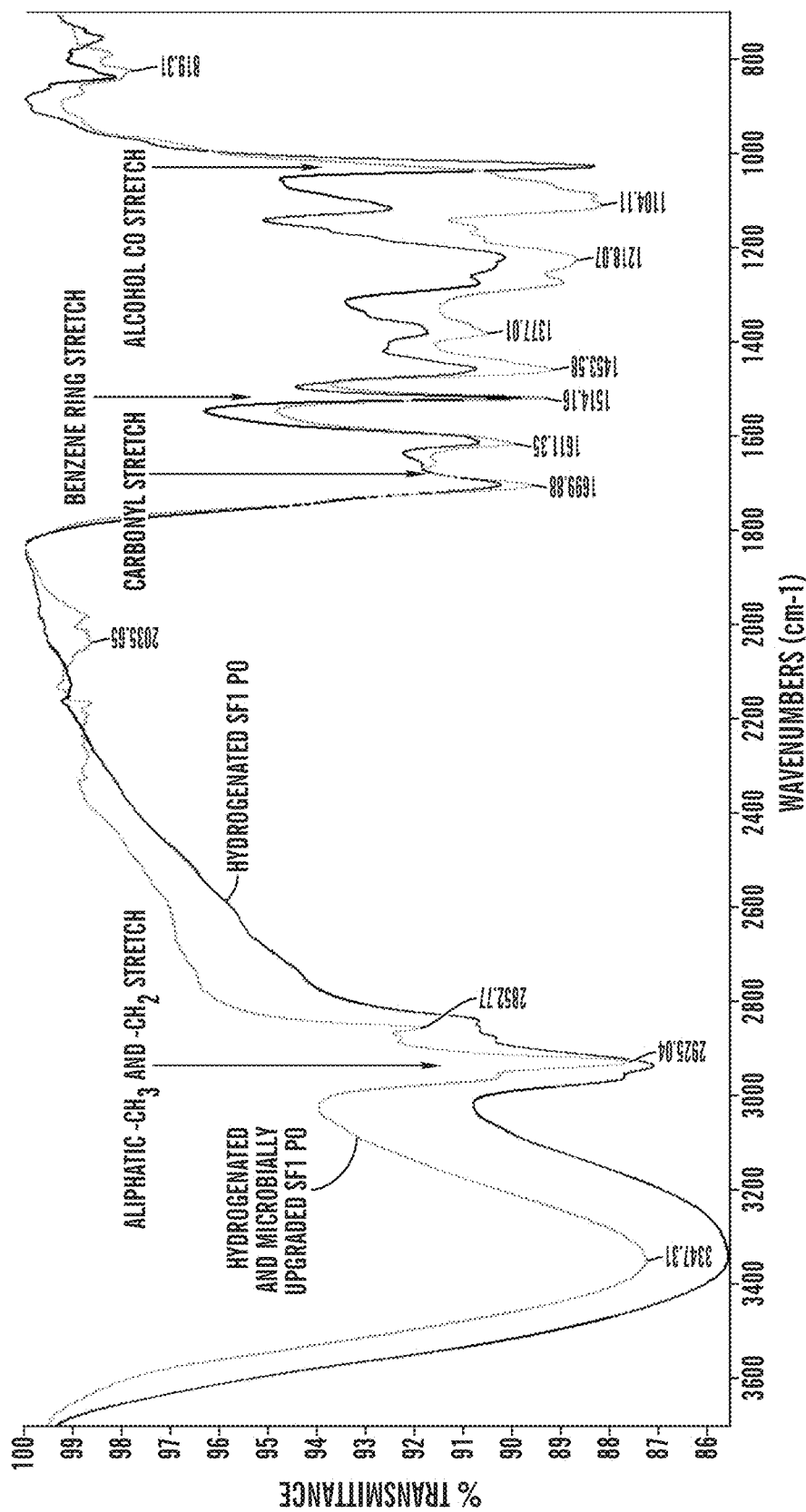
FIGS. 9A-C are graphs comparing the FTIR spectra of hydrogenated SF1 PO with SF1 PO after hydrogenation and fermentation with Baker's yeast (16 hours). The dry yeast precipitate shows a gain of aliphatic —$CH_3$ and —$CH_2$, a slight gain of carbonyls and benzene, with the loss of alcohols (FIG. 9A), while the hexane soluble product from fermentation indicates large gains in aliphatic —$CH_3$ and —$CH_2$— with large losses in carbonyls, benzene, and alcohols (FIG. 9B). The ethyl acetate soluble product from fermentation shows losses of aliphatic, carbonyls, and benzene (FIG. 9C).
Figure 9B:
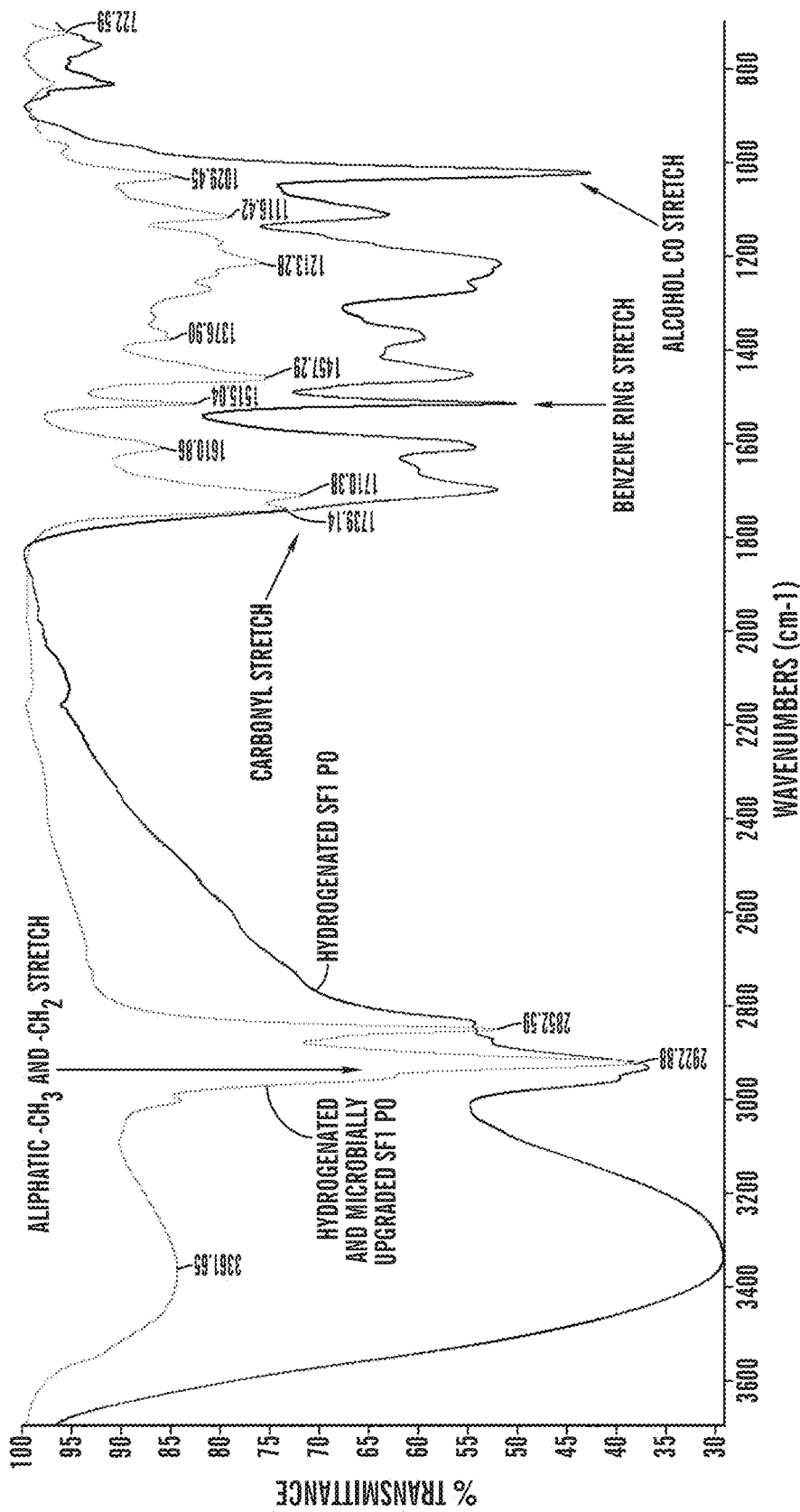
Figure 9C:
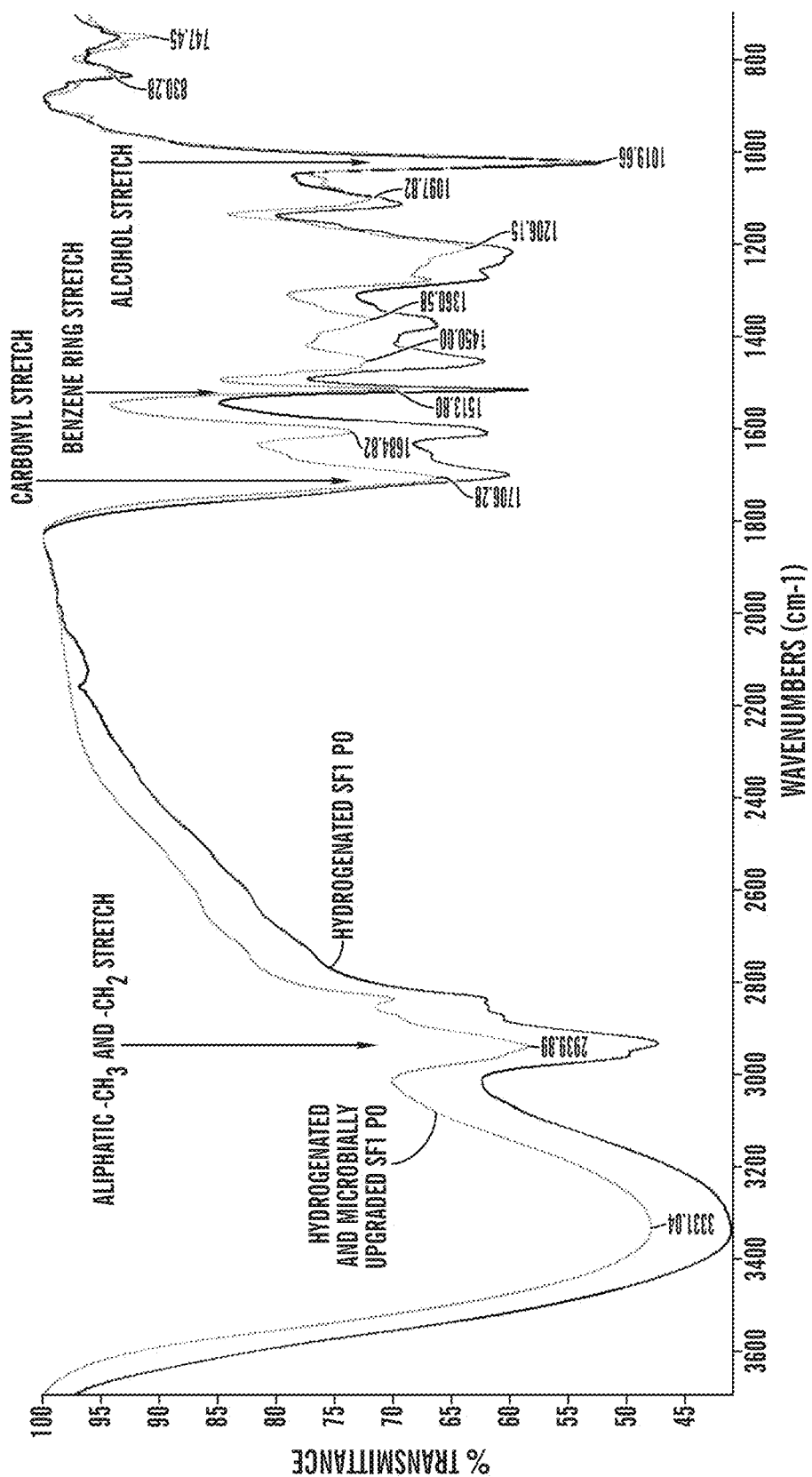

FIG. 9A-C shows the spectra of three of the obtained products following 16 hours fermentation. Product (a) was 22% of the sample. Product (b) was 16% of the initial sample. Product (c) was 28% of the initial sample. The fourth product, the aqueous phase, was not examined; however, it is expected that the low molecular weight alcohols and other water-soluble species would remain with the aqueous phase.

The 72 hour Baker's yeast fermentation produced 39% solid precipitate, 8% hexane soluble and 28% ethyl acetate soluble (not dried in vacuum oven, so it may contain a small percentage of solvent). The FTIR spectra (FIG. 10) indicated that the dry precipitate/product (a) gained aliphatic —$CH_3$ and —$CH_2$— groups, slightly gained carbonyls and benzene, and lost alcohols. The soluble constituents of the hexane soluble fraction/product (b) indicated large gains in aliphatic —$CH_3$ and —$CH_2$— with large losses in carbonyls, benzene, and alcohols. The ethyl acetate soluble fraction/product (e) showed a loss of aliphatic, carbonyls, and benzene. This was solvent dependant, as previously described, with the water-soluble components remaining in the aqueous phase.

Each product (a-c) contained different species of molecules and, therefore, the FUR and $^1$H NMR spectra show losses of alcohols in both products (a) and (b). The water-insoluble alcohols were present in product (c). Generally, Baker's yeast reduced ketones to alcohols and the shorter chain alcohols remained with the aqueous phase, i.e., product (d).

Example 4

Low Temperature Low Pressure Hydrogenation (LTLP-H) of Bio-Oil Fractions (SF3, SF4, and SF5) and Whole Bio-oil Fractionated distillation of bio-oil is typically not feasible because of the lignin-derived phenolic decomposition products, high water content, and hundreds of compounds containing various functional groups (Mohan et al., "Pyrolysis of Wood/Biomass for Bio-oil: A Critical Review" *Energy & Fuels* 20: 848-889 (2006), which is hereby incorporated by reference in its entirety). Typically, distillation is not used to completely vaporize constituents in bio-oil at 100° C. or higher temperatures due to bio-oil's high reactivity. At these elevated temperatures, a solid residue is produced, yielding up to 50 wt % of the original liquid (Mohan et al., "Pyrolysis of Wood/Biomass for Bio-oil: A Critical Review" *Energy & Fuels* 20: 848-889 (2006); Bridgwater, "Renewable Fuels and Chemicals by Thermal Processing of Biomass" *Chemical Engineering Journal* 91: 87-102 (2003); Czernik et al., "Overview of Applications of Biomass Fast Pyrolysis Oil" *Energy & Fuels* 18: 590-598 (2004), all of which are hereby incorporated by reference in their entirety).

Various distillation techniques have been tried, often requiring advanced distillation equipment (Capunitan et al, "Characterization and Separation of Corn Stover Bio-Oil by Fractional Distillation" *Fuel* 112: 60-73 (2013), which is hereby incorporated by reference in its entirety). A review of the literature concerning bio-oil distillation and separation and resulting yields are shown in Table 4.

TABLE 4

The distillation techniques used for the separation of bio-oil, the biomass used to produce the bio-oil, pressures and termperatures used during the distillation, and the resulting yields.

| Distillation Process | Biomass | Temperature (° C.) | Yield (wt %) | Ref* |
|---|---|---|---|---|
| Molecular Distillation | Sawdust | 130 | 55.4 | [5] |
| Ambient distillation | Softwood bark | 140 | 11.7 | [6] |
| Flash distillation | Wood tar | 300 | 44 | [7] |
| Vacuum Distillation | Cornstover | 100-180 | 57.1-65 | [4] |
| Rectification | Sawdust | 145 | <40 | [8] |

*Ref: [4] Capunitan et al, "Characterization and Separation of Corn Stover Bio-Oil by ractional Distillation" *Fuel* 112: 60-73 (2013); [5] Wang et al., "Separation of Bio-Oil by Molecular Distillation" *Fuel Processing Technology* 90: 738-745 (2009); [6] Boucher et al., "Bio-Oils Obtained by Vacuum Pyrolysis of Softwood Bark as a Liquid Fuel for Gas Turbines. Part I: Properties of Bio-Oil and its Blends with Methanol and a Pyrolytic Aqueous Phase" *Biomass and Bioenergy*, 19: 337-350 (2000); [7] Carazza et al., Fractionation of Wood Tar, in: Advances in Thermochemical Biomass Conversion 1465-1474 (Springer, 1993); and [8] Xu et al., "Experimental Research on the Bio-Oil Derived from Biomass Pyrolysis Liquefaction" *Nongye Gongcheng Xuehao/Transactions of the Chinese Society of Agricultural Engineering* 15: 177-181 (1999).

Low temperature, low pressure hydrogenation (LTLP-H) experiments were performed to whole bio-oil as well as bio-oils collected from condenser and electrostatic precipitator stages of the bio-oil collection system, designated as stage franctions (SFs) 3, 4, and 5, respectively. These experiments were carried out to determine if mild upgrading conditions would show improvements in the properties/characteristics of the resulting hydrogenated oil. The experimental set-up for the fractionation of bio-oil at SF3, SF4, and SF5 is similar to those described in U.S. Pat. No. 8,476,480 to Brown, et al. which is hereby incorporated by reference in its entirety (see also, the fast pyrolysis reactor and five stage fractions (SF) of bio-oil recovery, as shown in FIG. 1).

The experimental set-up for the fractionation and the LTLP-H reaction conditions are similar to those described in Example 1.

Methanol was used as a solvent for LTLP-H of SF3 (1:1 ratio of methanol:SF3), SF4 (3:1 ratio of methanol:SF4), and no solvent was used for LTLP-H of SF5. These ratios will vary according to the hydrogenation reactor system used. This work was accomplished with a flow-through reactor (H-Cube) which required dilution. The optimum results were obtained with a 5% $H_2$ supply (3mL/min), 25° C., and 1 bar of pressure using a 10% Pd/C catalyst for SF3 and SF4. The optimum conditions for SF5 was 10% $H_2$ (6 mL/min), 25° C., 1 bar, with 10% Pd/C. LTLP-H of the whole bio-oil was done using 100% $H_2$ (60 mL/min), 25° C., 1 bar, and a 10% Pd/C catalyst with a 1:1 ratio of methanol to whole bio-oil. A second reaction was also performed using the previously listed conditions for whole bio-oil with no solvent dilution during LTLP-H. Optimal results depend on the hydrogenation reactor.

Figure 12:
FIG. 12 is a photograph showing two collected distillates from the non-hydrogenated whole bio-oil.
Figure 13:
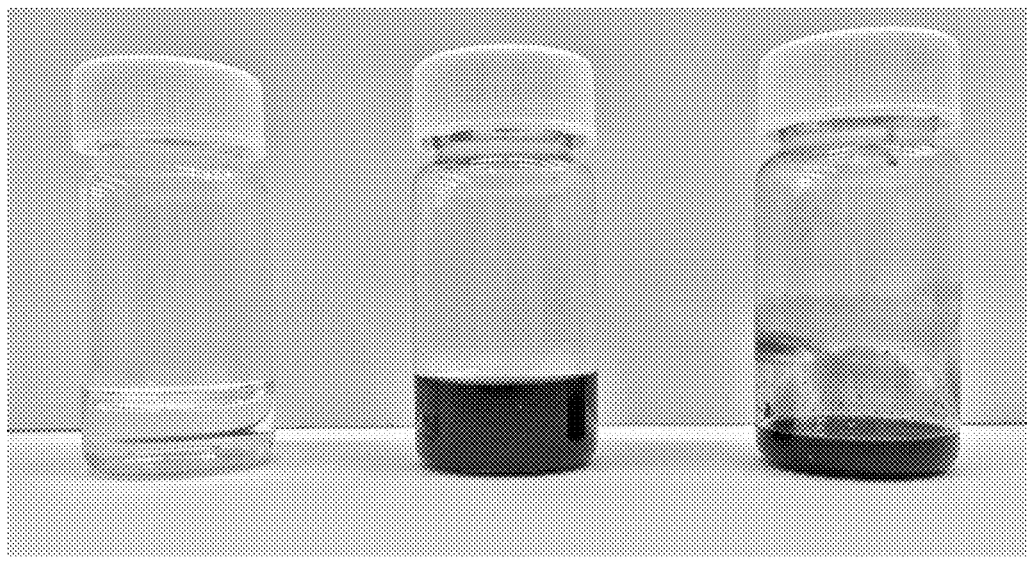
FIG. 13 is a photograph showing three collected distillates from the hydrogenated whole bio-oil. The left panel shows aqueous phase of the hydrogenated whole bio-oil extracted from the rotary evaporation prior to the vacuum distillation.
Figure 14:
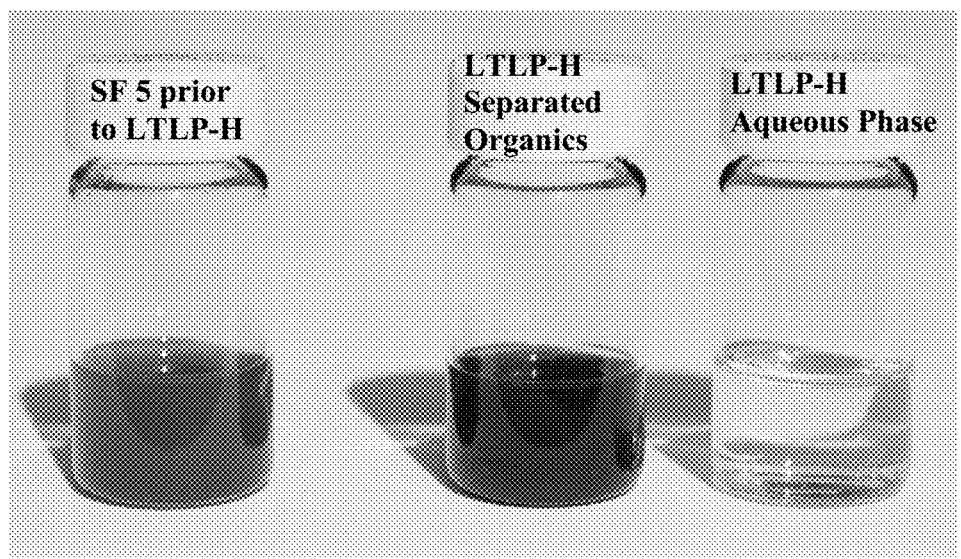
FIG. 14 is a photograph showing the bio-oil obtained from stage fraction (SF) 5 prior to low temperature, low pressure hydrogenation (LTLP-H) (left), as compared to the organic phase (middle) and aqueous phase (right) obtained from SF 5 after LTLP-H and rotary evaporation at 40° C.
Figure 15B:
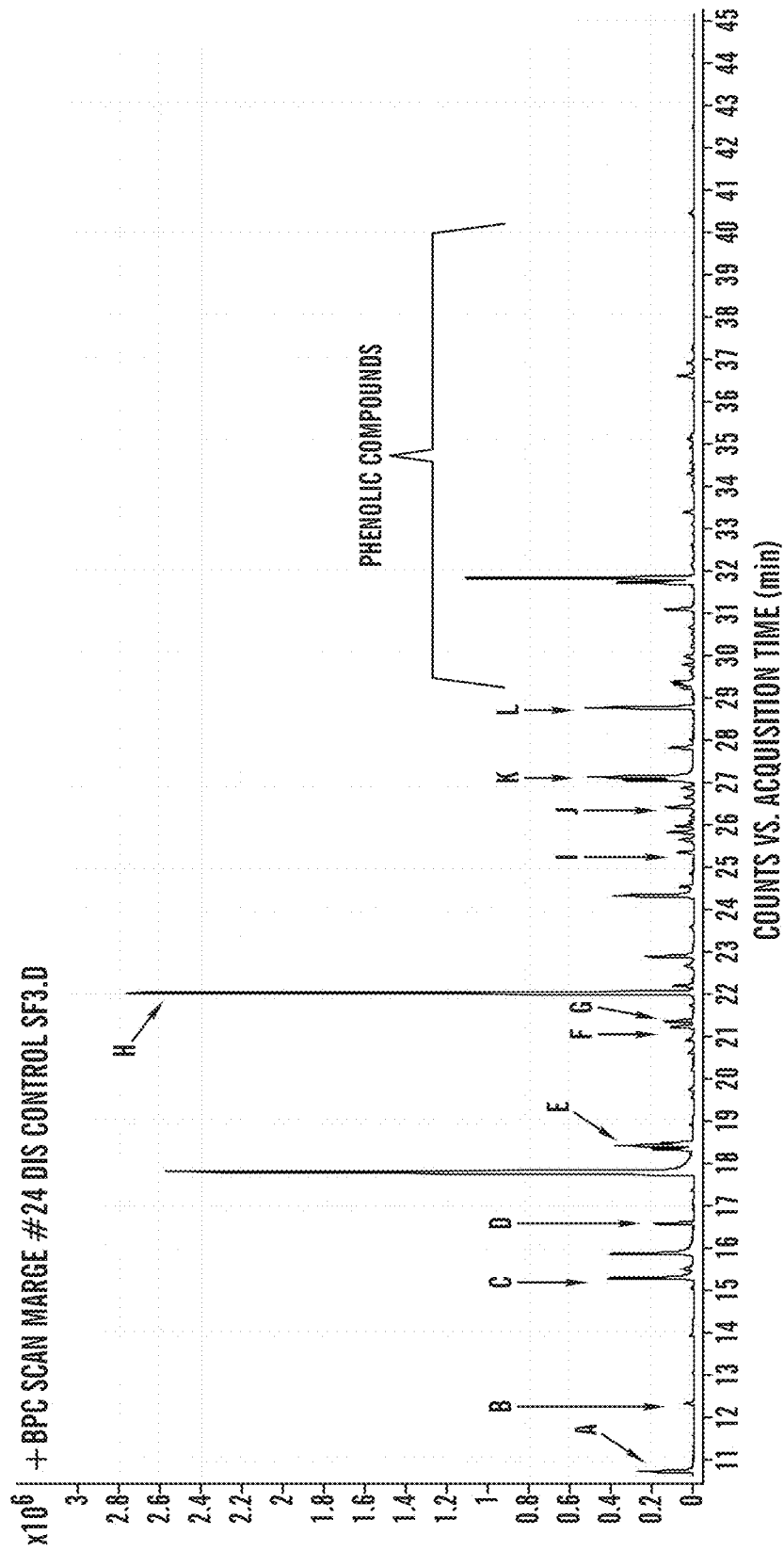
Figure 15C:
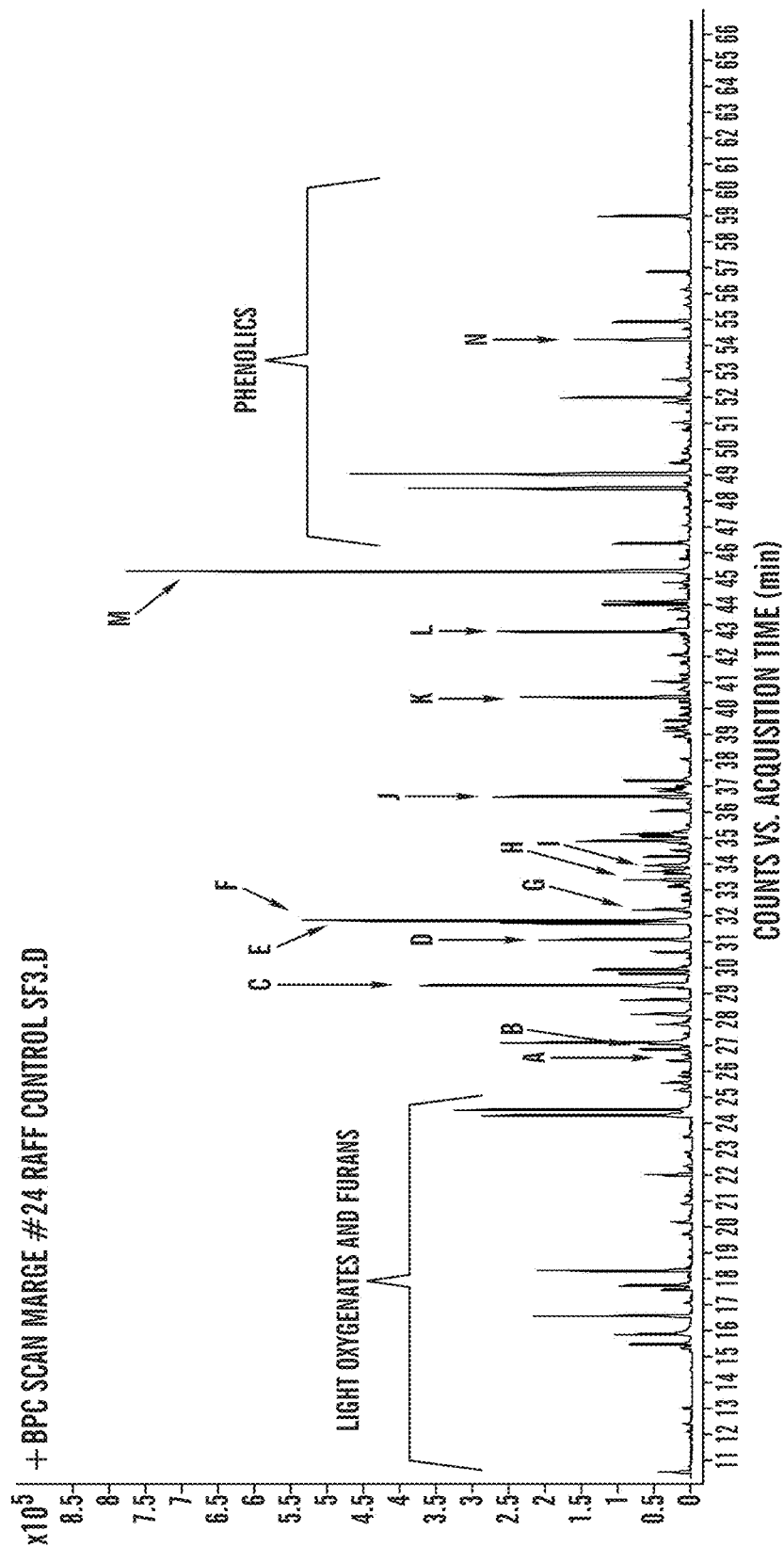
Figure 15D:
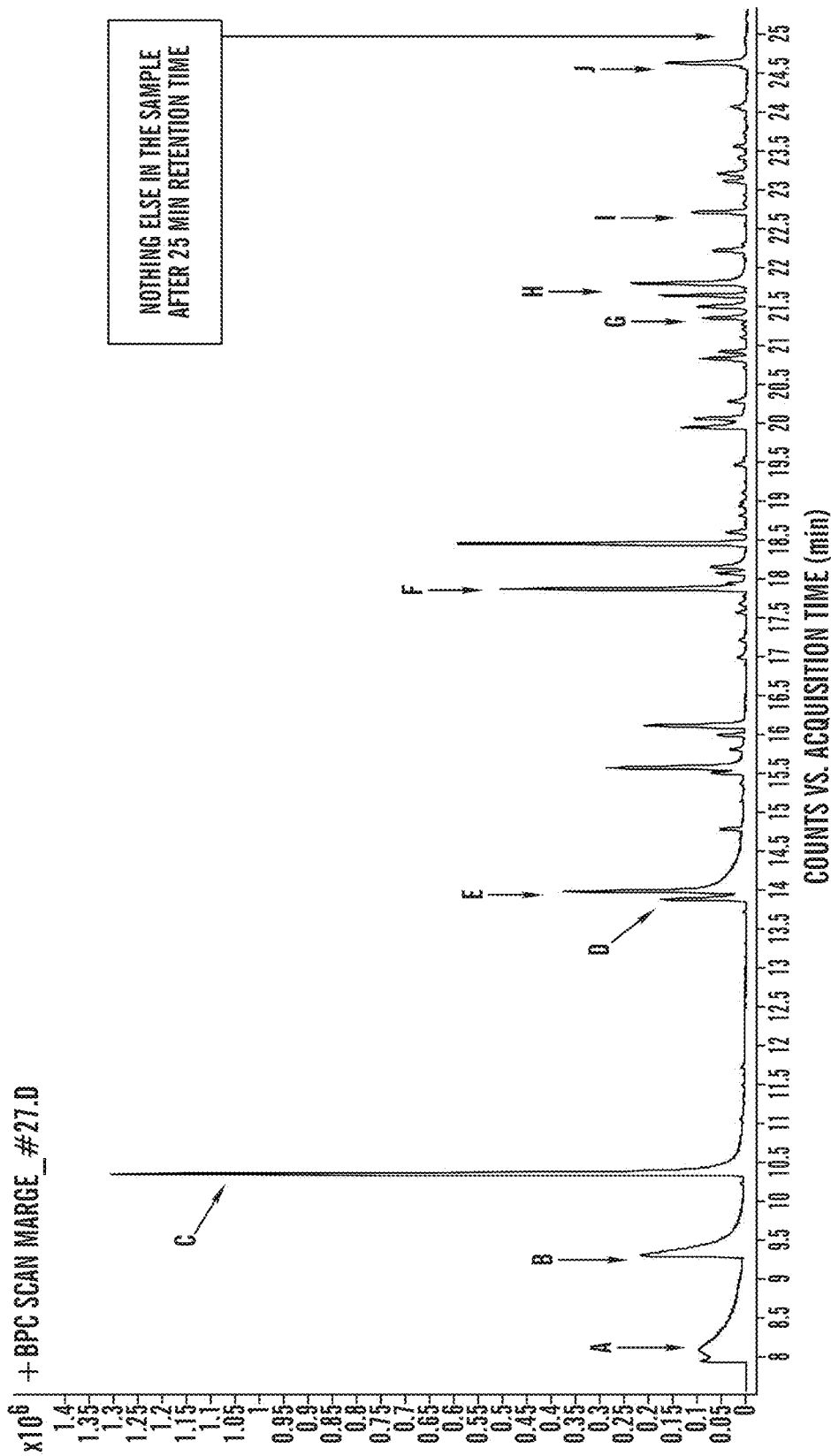
Figure 15E:
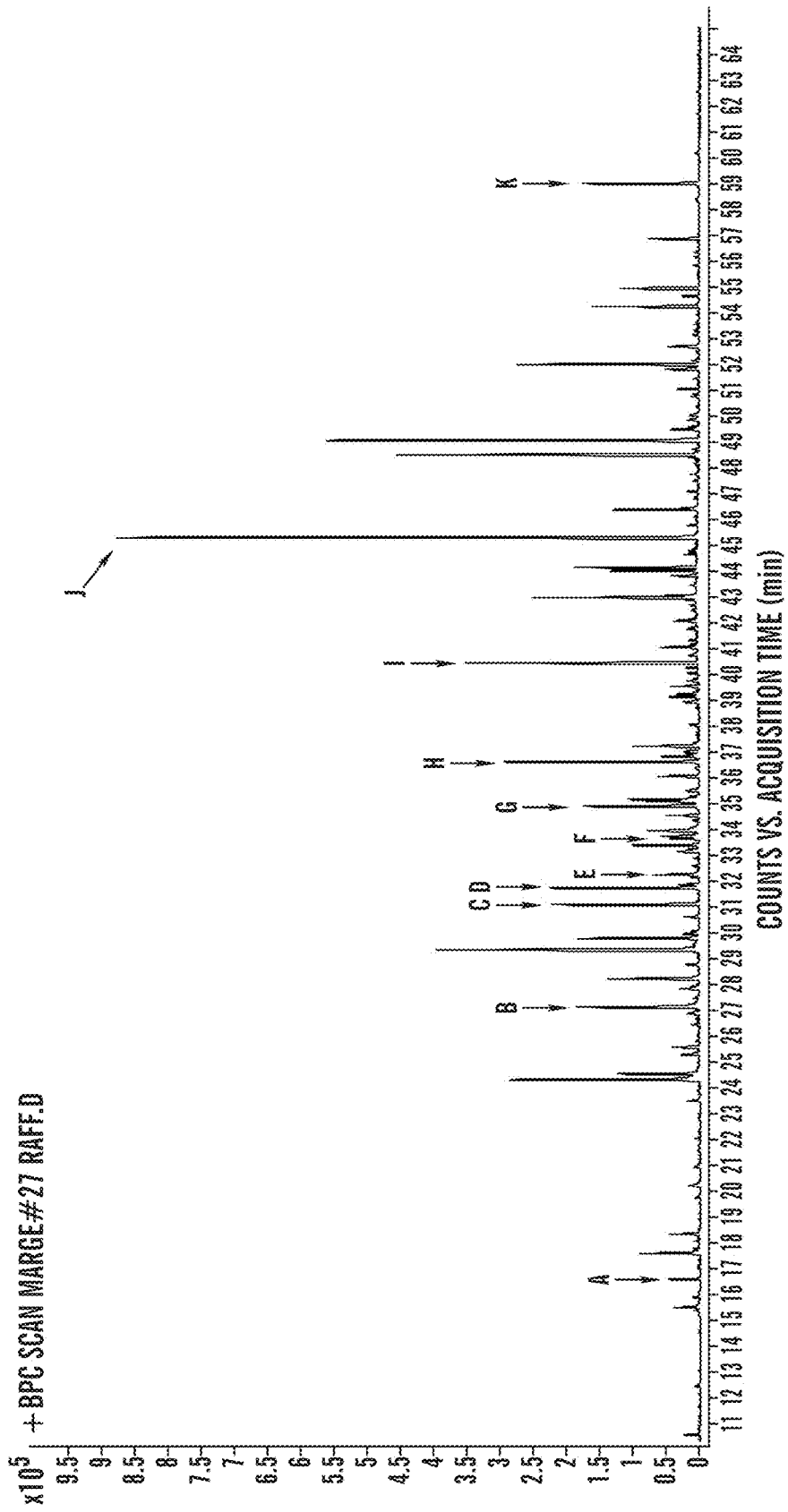
Figure 16A:
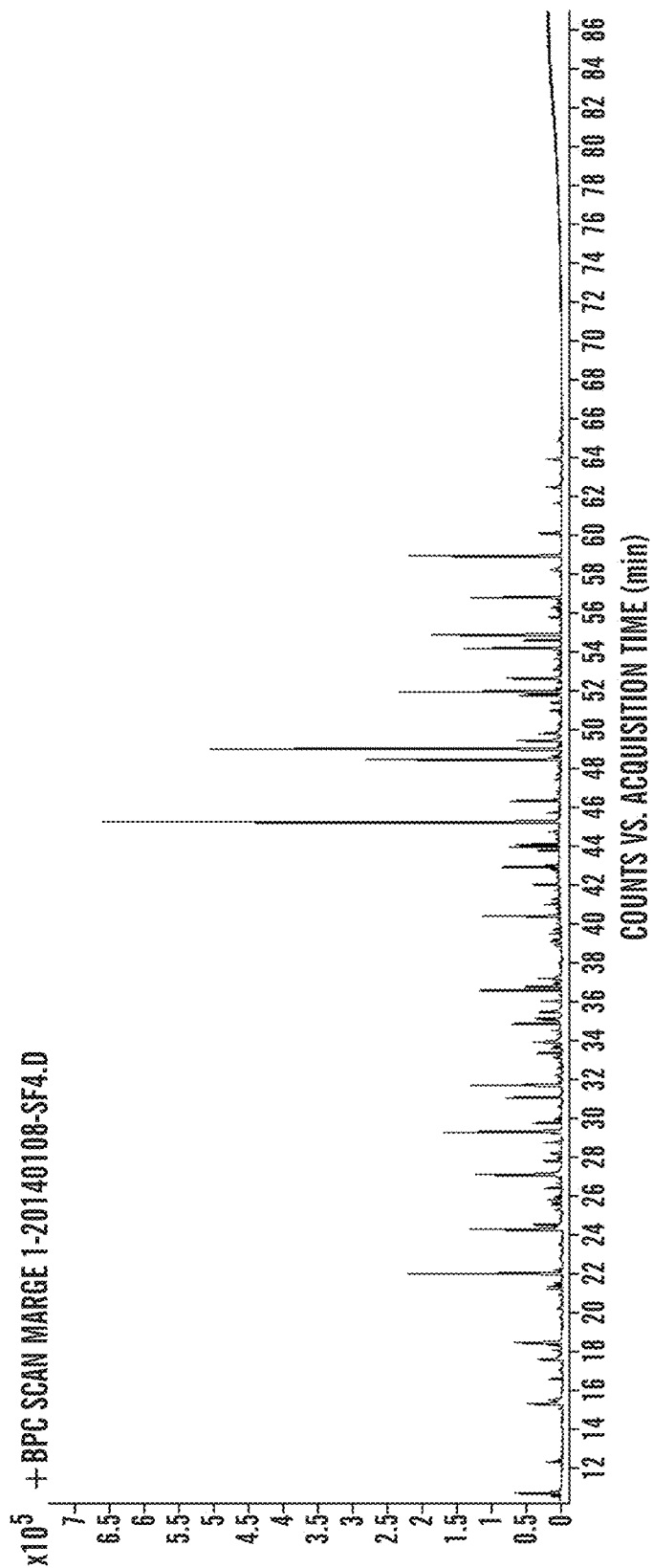
FIG. 16A-D are graphs showing the GC/MS results of stage fraction (SF) 4.
Figure 16B:
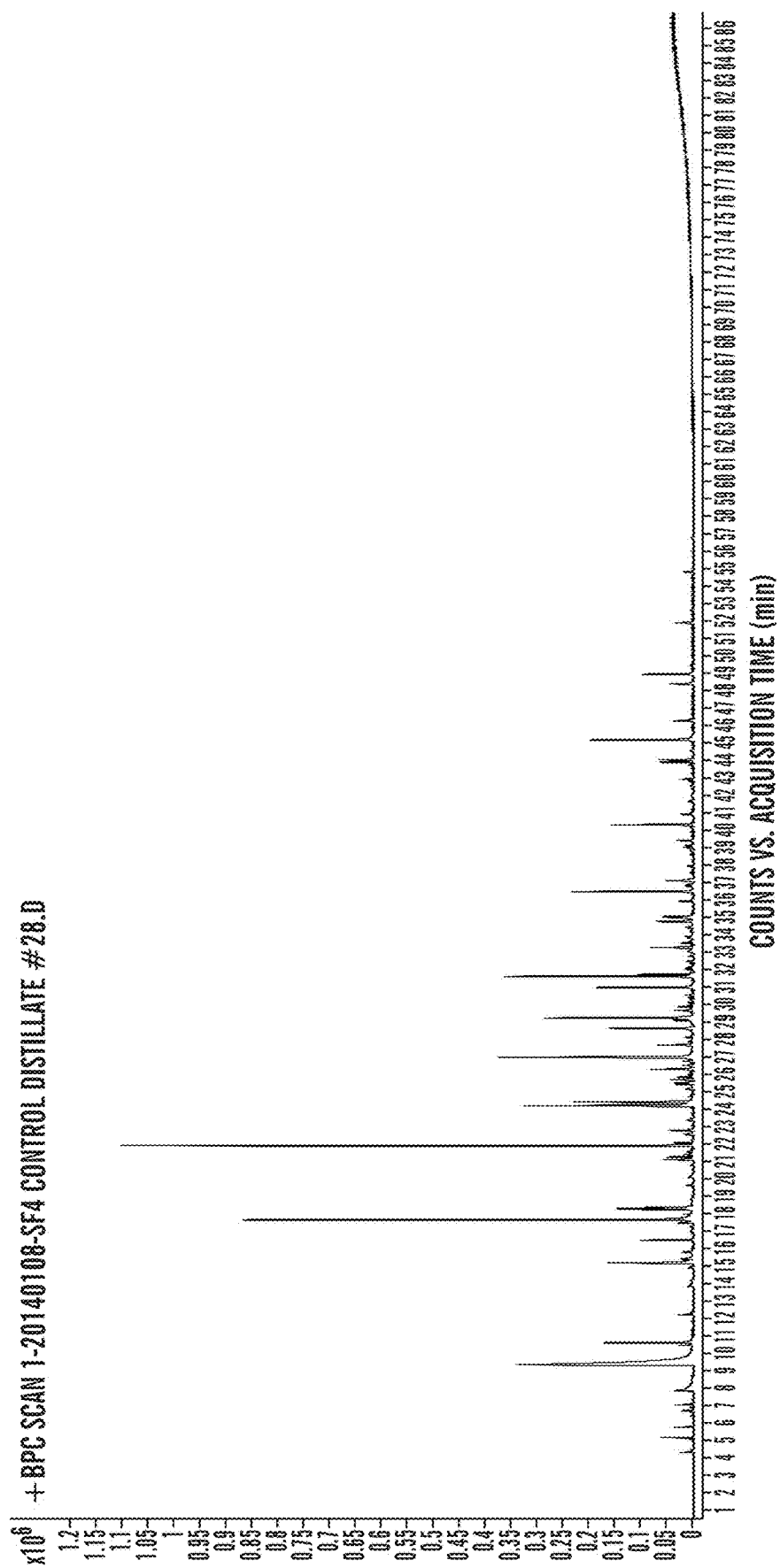
Figure 16C:
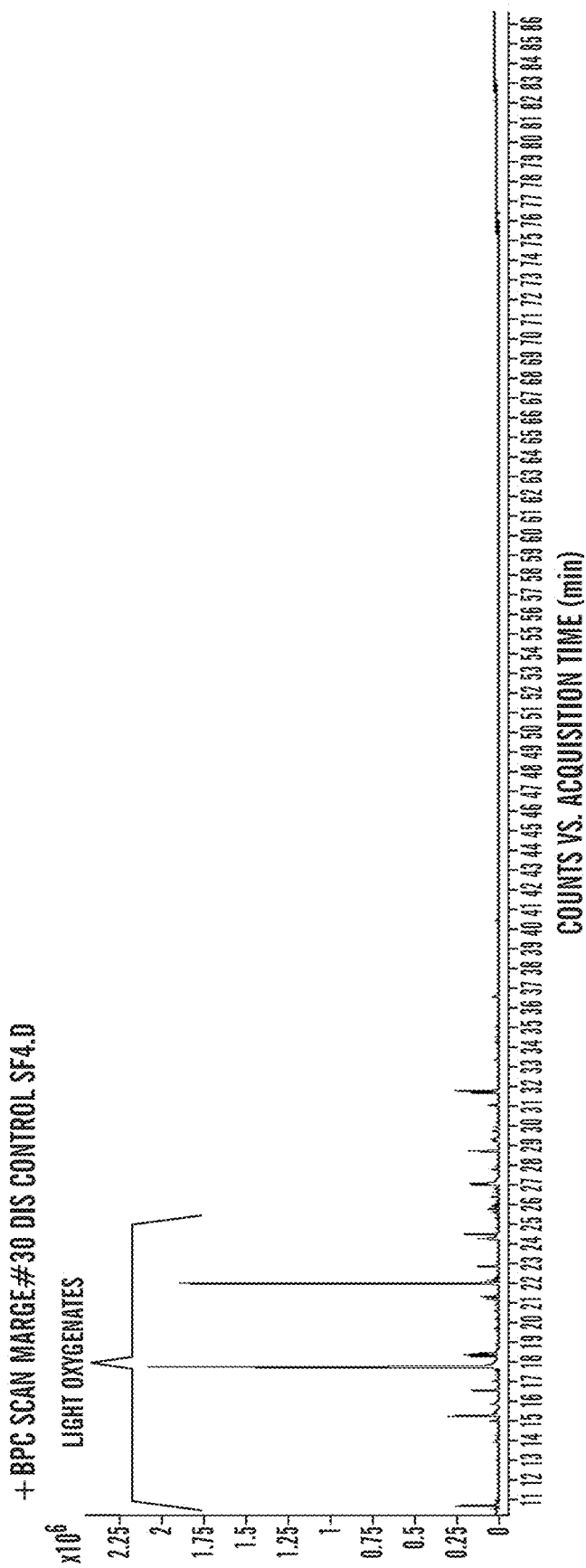
Figure 16D:
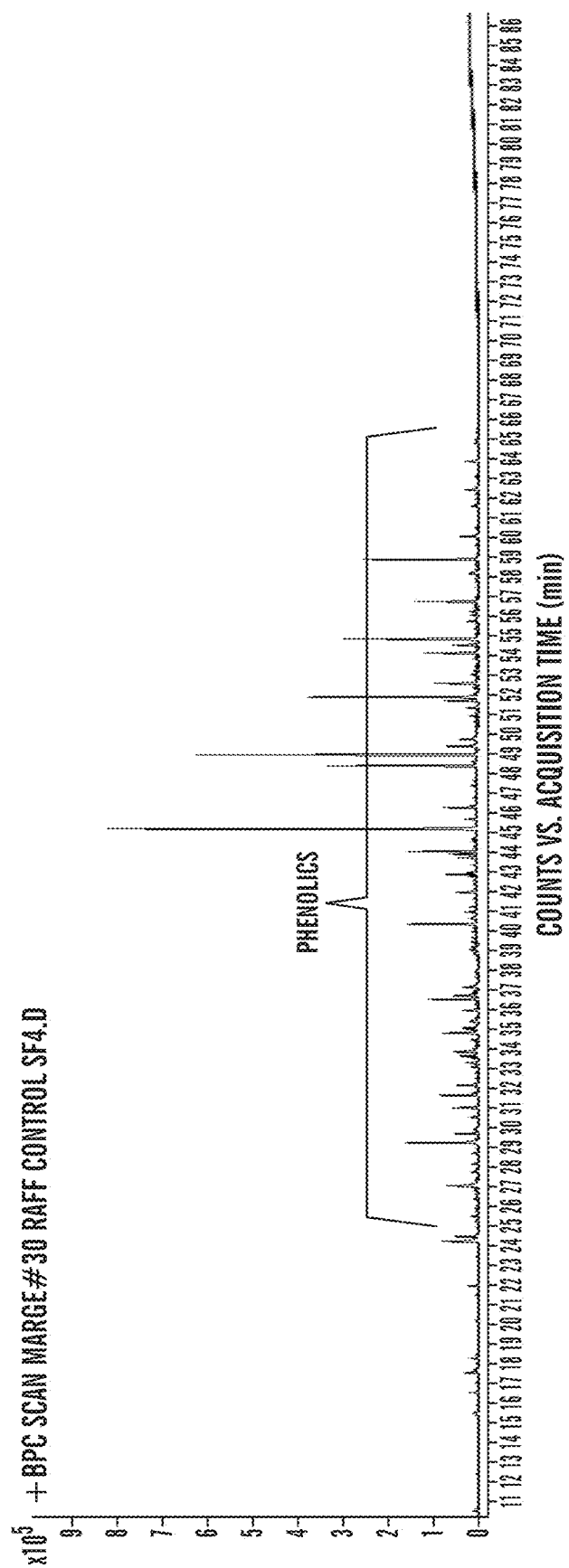

As shown in Table 5, high yields (89.9-99.10 wt %) were obtained for all samples, including the controls which were not hydrogenated. However, these yields do not necessarily reflect upgradable quality oil in the control samples (FIG. 12). Comparing the non-hydrogenated control in FIG. 12 and the hydrogenated bio-oil in FIG. 13, the LTLP-H produced clear upgradable samples through distillation (FIG. 13), whereas some controls produced cloudy samples, suggesting the formation of emulsions. Others showed minimized yields for light oxygenates and phenolics without separation of the two streams. Utilizing LTLP-H, light oxygenates for SF 3 increased with a corresponding decrease in the phenolic raffinate. In addition, separation of the furan and phenolic stream was obtained (Table 5). SF 4 showed the opposite trend: there were observed decreases in the light oxygenates and increases in the raffinate stream. It was determined that vacuum distillation was more effective than simple distillation due to the higher temperatures needed for simple distillation. Successful separation of SF 5 after LTLP-H was easily accomplished utilizing rotary evaporation at 40° C. (FIG. 14).

to separate the light oxygenates from the phenolics for specific end-use. By treating these bio-oil streams with LTLP-H, specific catalysts can be used for upgrading and/or separating streams for specialty chemical separation and industrial use.

Figure 18D:
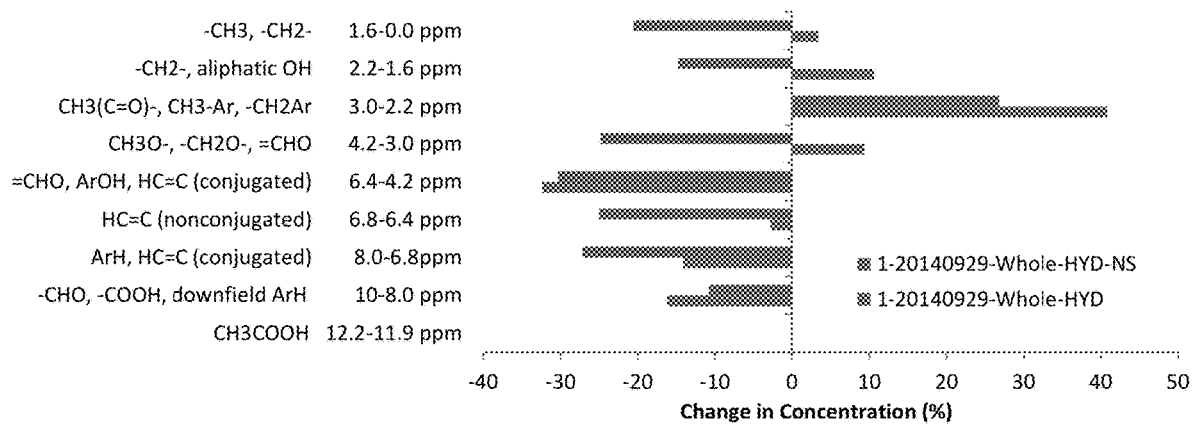
FIG. 18D shows the comparison of normalized peak area changes between the hydrogenated whole bio-oil (shown in FIG. 18B) using methanol as a solvent during the hydrogenation and the hydrogenated whole bio-oil that was hydrogenated without solvent (shown in FIG. 18C).

LTLP-H of the whole bio-oil, without the use of solvent, indicated differences in the $^1$H NMR spectra (FIG. 18). A loss of aliphatics and increases in protons alpha to ketones, aldehydes, and carboxyl groups (3.0-2.2 ppm) were observed (Ingram et al., "Pyrolysis of Wood and Bark in an Auger Reactor: Physical Properties and Chemical Analysis of the Produced Bio-oils" *Energy & Fuels* 22: 614-625 (2007), which is hereby incorporated by reference in its

TABLE 5

Comparison of reaction conditions and yields for SF3, SF4, SF5, and whole bio-oil. Vacuum distillation was used for SF3, SF4, and whole bio-oil. Rotary evaporation was used for the hydrogenated SF5 while simple distillation was used for the SF5 control.

| Sample | LTLP Conditions | Temperature (° C.) | Light Oxygenates (wt %) | Phenolic/Organic Raffinate (wt %) | Yields (wt %) |
|---|---|---|---|---|---|
| SF3 (1:1 methanol:SF 3 dilution rate) | | | | | |
| Control | — | 52.9 | 18.61 | 73.96 | 92.57 |
| Control | — | 50.3 | 19.36 | 74.11 | 93.47 |
| Duplicate Trial #1 | 5% $H_2$, 25° C., 1 bar, 10% Pd/C | 61.6 | 48.07 | 47.78 | 95.85 |
| Duplicate Trial #2 | 5% $H_2$, 25° C., 1 bar, 10% Pd/C | 61.4 | 46.92 | 52.18 | 99.10 |
| SF4 (3:1 methanol:SF4 dilution rate) | | | | | |
| Control | — | 106 | 41.72 | 50.58 | 92.30 |
| Duplicate Trial #1 | 5% $H_2$, 25° C., 1 bar, 10% Pd/C | 57.6 | 23.84 | 70.50 | 94.34 |
| Duplicate Trial #2 | 5% $H_2$, 25° C., 1 bar, 10% Pd/C | 58.5 | 17.58 | 76.10 | 93.68 |
| SF5 (no solvent used) | | | | | |
| Control | — | 111.4 | 98.6 | nothing collected* | 98.6 |
| | 10% $H_2$, 25° C., 1 bar, 10% Pd/C | 40 | 78.4 | 17.1 | 95.5 |
| Whole Bio-Oil (1:1 methanol:whole bio-oil dilution rate) | | | | | |
| Control | — | 190 | 66.9 | 24.1 | 91 |
| Trial #1 | 100% $H_2$, 25° C., 1 bar, 10% Pd/C | 145 | 64.1 | 25.8 | 89.9 |

*Non-hydrogenated SF5 control distillation did not separate furans/light oxygenates/water from the phenolic compounds due to azeotrope formation.

Temperatures used for the vacuum distillation ranged from 46.9-61.6° C. for LTLP-H of SF3 and SF4. The majority of hydrogenated whole bio-oil was distilled between 32-87° C., but the temperature was taken to 145° C. to further investigate possible distillate collection. The non-hydrogenated whole bio-oil control sample did not start condensing until approximately 80° C. and immediately rose to 180-190° C. continuing to condense, suggesting azeotrope formation. After condensing stopped, the temperature fell to below 100° C. Obvious visual differences existed between the non-hydrogenated and hydrogenated whole oil (FIGS. 12 and 13).

Gas chromatography/mass spectrometry (GC/MS) chromatograms for SF3 (FIG. 15), SF4 (FIG. 16), and SF5 (FIG. 17) indicate the separation of the light oxygenates and the phenolics in the hydrogenated samples. These chromatograms clearly indicate the positive effect of LTLP-H's ability entirety). There were also losses of protons on carbon atoms next to aliphatic alcohols or ethers, methoxy groups, or methylene groups that join two aromatic rings at 4.0-3.2 ppm (Oasmaa et al., "Characterization of Hydrotreated Fast Pyrolysis Liquids" *Energy & Fuels* 24: 5264-5272 (2010), which is hereby incorporated by reference in its entirety). Larger decreases in both conjugated and non-conjugated C=C bonds (8.0-6.4 ppm) were apparent (Ingram et al., "Pyrolysis of Wood and Bark in an Auger Reactor: Physical Properties and Chemical Analysis of the Produced Bio-oils" *Energy & Fuels* 22: 614-625 (2007), which is hereby incorporated by reference in its entirety).

Figure 19:
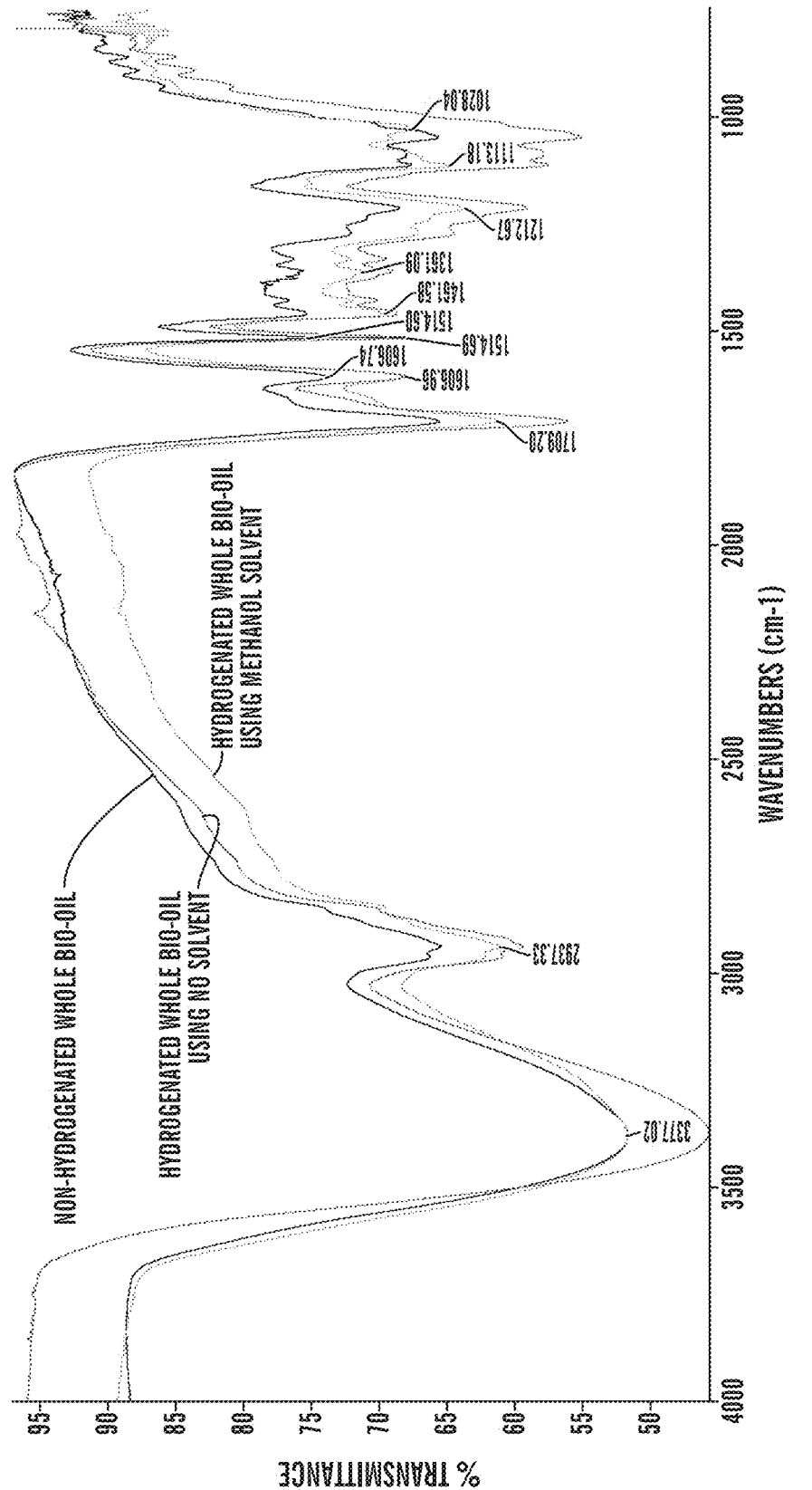
FIG. 19 is a graph comparing FTIR spectra of the non-hydrogenated whole bio-oil, the hydrogenated whole bio-oil using methanol as a solvent during hydrogenation, and the hydrogenated whole bio-oil where no solvent was used during hydrogenation.

FTIR spectra (FIG. 19) indicated a loss of the —OH stretch in alcohols and phenols for both hydrogenated whole bio-oil samples at 3370.1 $cm^{-1}$ as well as losses of the carbonyl (C=O) stretch at 1709.2 $cm^{-1}$, and of the C—O—C stretch in ethers and/or esters (1212.67 $cm^{-1}$).

There were losses in the hydrogenated whole bio-oil in which no solvent was used at 1606.96 cm$^{-1}$ and 1514.6 cm$^{-1}$, which is most likely due to the loss of the benzene stretch (Lambert et al., "Introduction to Organic Spectroscopy" (Prentice Hall, New Jersey, 1987), which is hereby incorporated by reference in its entirety).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method for upgrading a bio-oil fraction comprising:
   providing a bio-oil fraction containing one or more phenolic compounds, wherein the bio-oil fraction has a water content of between 3% and 7% by weight, and wherein the bio-oil fraction is substantially free of sugar;
   providing hydrogen (H$_2$); and
   reacting the bio-oil fraction and hydrogen in the presence of a catalyst at a temperature of 15° C. to 50° C. at about atmospheric pressure to produce a hydrogenated liquid oil at a carbon yield of over 75%, wherein the hydrogenated liquid oil has a lower viscosity than the bio-oil fraction.

2. The method of claim 1, which produces the hydrogenated liquid oil at a carbon yield of over 80%, over 85% or over 90%.

3. The method of claim 1, wherein the viscosity of the hydrogenated liquid oil is at least 45%, at least 50%, at least 55%, at least 60%, at least 65%, at least 70%, at least 75%, or at least 80% lower than the bio-oil fraction.

4. The method of claim 1, wherein the hydrogenated liquid oil contains substantially no coke and/or substantially no carbon gases and/or substantially no polymerized phenolic molecules.

5. The method of claim 1, wherein the hydrogenated liquid oil contains fewer vinyl groups, ether groups, and/or carbonyl groups than the bio-oil fraction.

6. The method of claim 1, wherein the hydrogenated liquid oil contains increased aliphatics, phenolic monomers, and/or alcohols compared to the bio-oil fraction.

7. The method of claim 1, wherein the catalyst comprises Pd, Ru, Ru+Pd, Pt, Raney Ni, Ni, CoMo, or NiMo.

8. The method of claim 7, wherein the catalyst comprises Pd.

9. The method of claim 7, wherein the catalyst is palladium on activated carbon (Pd/C).

10. The method of claim 1, wherein said providing the bio-oil fraction comprises:
    subjecting a biomass to a fast pyrolysis process.

11. The method of claim 1 further comprising:
    reacting the hydrogenated liquid oil with zinc and hydrochloric acid at a temperature of less than 0° C. under conditions effective to produce an upgraded hydrogenated bio-oil product containing fewer carbonyl groups than the hydrogenated liquid.

12. The method of claim 11 further comprising:
    adding one or more fermentation organisms and a sugar source to the hydrogenated liquid oil; and
    incubating the one or more fermentation organisms and the hydrogenated liquid oil at 15° C. to 30° C. for 16 hours to 72 hours to produce an upgraded, hydrogenated bio-oil fermentation product containing fewer carbonyl groups than the hydrogenated liquid.

13. The method of claim 1 further comprising:
    adding one or more fermentation organisms and a sugar source to the hydrogenated liquid oil to form a fermentation mixture; and
    incubating the fermentation mixture at 15° C. to 30° C. for 16 hours to 72 hours to produce an upgraded, hydrogenated bio-oil fermentation product containing fewer carbonyl groups than the hydrogenated liquid.

14. The method of claim 13, wherein the one or more fermentation organisms is/are selected from the group consisting of *Saccharomyces cerevisiae, Schizosaccharomyces pombe*, and *Pichia stipitis*.

15. The method of claim 13, wherein the sugar source is selected from the group consisting of glucose, fructose, sucrose, maltose, maltotriose and other fermentable sugar feed.

16. The method of claim 1, wherein said bio-oil fraction is recovered from one or more condensation stages and/or one or more electrostatic precipitator stages, said bio-oil fraction being selected from the group consisting of stage fraction 1 (SF1), stage fraction 2 (SF2), and combinations thereof.

17. The method of claim 1, wherein the reacting is carried out at temperature of about 25° C.

* * * * *